(12) United States Patent
Chiu et al.

(10) Patent No.: US 11,542,539 B2
(45) Date of Patent: Jan. 3, 2023

(54) NANOPARTICLE TRANSDUCER SENSORS AND METHODS OF USE THEREOF

(71) Applicants: UNIVERSITY OF WASHINGTON, Seattle, WA (US); LAMPROGEN, INC., Seattle, WA (US)

(72) Inventors: Daniel T. Chiu, Seattle, WA (US); Jiangbo Yu, Seattle, WA (US); Changfeng Wu, Changchun (CN); Kai Sun, Changchun (CN)

(73) Assignees: UNIVERSITY OF WASHINGTON, Seattle, WA (US); LAMPROGEN, INC., Seattle, WA (US)

( * ) Notice: Subject to any disclaimer, the term of this patent is extended or adjusted under 35 U.S.C. 154(b) by 618 days.

(21) Appl. No.: 16/307,363

(22) PCT Filed: Jun. 5, 2017

(86) PCT No.: PCT/US2017/035983
§ 371 (c)(1),
(2) Date: Dec. 5, 2018

(87) PCT Pub. No.: WO2017/214047
PCT Pub. Date: Dec. 14, 2017

(65) Prior Publication Data
US 2019/0284601 A1      Sep. 19, 2019

(30) Foreign Application Priority Data
Jun. 6, 2016    (WO) ................ PCT/CN2016/084986

(51) Int. Cl.
*B82Y 15/00*      (2011.01)
*B82Y 30/00*      (2011.01)
(Continued)

(52) U.S. Cl.
CPC .............. *C12Q 1/006* (2013.01); *C09K 11/07* (2013.01); *G01N 21/64* (2013.01); *B82Y 15/00* (2013.01); *B82Y 30/00* (2013.01)

(58) Field of Classification Search
CPC ........ C12Q 1/006; C09K 11/07; G01N 21/64; B82Y 15/00; B82Y 30/00
See application file for complete search history.

(56) References Cited

U.S. PATENT DOCUMENTS

2007/0095664 A1 * 5/2007 Chou .................. C23C 14/0641
                                                            204/192.1
2010/0075361 A1    3/2010 Mattoussi et al.
(Continued)

FOREIGN PATENT DOCUMENTS

| CN | 103616361 A | 3/2014 |
| CN | 105462590 A | 4/2016 |

(Continued)

OTHER PUBLICATIONS

Extended European Search Report, dated Oct. 11, 2019, for European Patent. Application No. 17810793.4. (10 pages).
European Examination Report dated May 15, 2020, issued in European Application No. EP 17810793.4. filed Jun. 5, 2017, 5 pages.
(Continued)

Primary Examiner — Brian J. Sines
(74) Attorney, Agent, or Firm — Hristenson O'Connor Johnson Kindness PLLC

(57) ABSTRACT

The present disclosure provides nanoparticle transducers and methods of use thereof for the detection of analyte concentrations in a fluid. Nanoparticle transducers can comprise a nanoparticle, such as a Pdot, coupled to an enzyme that catalyzes a reaction with the analyte. The nanoparticle transducers further comprise chromophores that emit fluorescence that varies as a function of the concentration of one (Continued)

of the elements of the reaction. The nanoparticle transducer thus changes fluorescence as the analyte concentration changes, transforming analyte concentration values into fluorescence intensities. The measurement of these intensities provides a measurement of the analyte concentration. The nanoparticle transducers are biocompatible, allowing for use in vivo, for the monitoring of analyte blood concentrations such as blood glucose concentrations.

17 Claims, 26 Drawing Sheets

(51) Int. Cl.
    *C12Q 1/00*     (2006.01)
    *C09K 11/07*     (2006.01)
    *G01N 21/64*     (2006.01)

(56) References Cited

U.S. PATENT DOCUMENTS

| | | | |
|---|---|---|---|
| 2010/0113901 A1 | 5/2010 | Zhang et al. | |
| 2012/0282632 A1* | 11/2012 | Chiu | C09K 11/06 525/186 |
| 2013/0266957 A1 | 10/2013 | Chiu et al. | |

FOREIGN PATENT DOCUMENTS

| | | |
|---|---|---|
| EP | 1496126 A1 | 1/2005 |
| EP | 2944605 A1 | 11/2015 |
| JP | 2005-151972 A | 6/2005 |
| JP | 2008-531989 A | 8/2008 |
| JP | 2010-517693 A | 5/2010 |
| JP | 2013-511700 A | 4/2013 |
| JP | 2016-508213 A | 3/2016 |
| JP | 2016-47252 A | 4/2016 |
| WO | 2008/146966 | 12/2008 |
| WO | 2011/057295 A2 | 5/2011 |
| WO | WO-2011057295 A2 | 5/2011 |
| WO | WO-2012054525 A2 | 4/2012 |
| WO | WO-2013101902 A2 | 7/2013 |
| WO | WO-2013116614 A1 | 8/2013 |
| WO | 2013/134401 A2 | 9/2013 |
| WO | WO-2014058903 A2 | 4/2014 |
| WO | 2014/160258 A1 | 10/2014 |
| WO | WO-2015006374 A1 | 1/2015 |
| WO | 2015/042204 A1 | 3/2015 |
| WO | 2015/081126 A1 | 6/2015 |
| WO | WO-2017210841 A1 | 12/2017 |
| WO | WO-2017214047 A1 | 12/2017 |

OTHER PUBLICATIONS

Brown, J.Q., et al. "Encapsulation of Glucose Oxidase and an Oxygen-Quenched Fluorophore in Polyelectrolyte-Coated Calcium Alginate Microspheres as Optical Glucose Sensor Systems," Biosensors and Bioelectronics, vol. 21, No. 1, pp. 212-216, Jul. 15, 2005.
Brown, et al. Encapsulation of glucose oxidase and an oxygen-quenched fluorophore in polyelectrolyte-coated calcium alginate microspheres as optical glucose sensor systems. Biosens Bioelectron. Jul. 15, 2005;21(1):212-6.
International search report with written opinion dated Mar. 2, 2017 for PCT/CN2016/084986.
International search report with written opinion dated Oct. 6, 2017 for PCT/US17/35983.
Pu, et al. Semiconducting Polymer Nanoprobe for In Vivo Imaging of Reactive Oxygen and Nitrogen Species. Angew.Chem.Int.Ed., vol. 39, No. 52, Aug. 13, 2013, pp. 10325-10329.
Second Examination Report dated Aug. 20, 2021, in corresponding Australian Patent Application No. 2017278240, 13 pages.
Grant, P.S. et al., "Nanostructured fluorescent particles for glucose sensing," Proceedings of SPIE, vol. 4624, Optical Diagnostics and Sensing of Biological Fluids and Glucose and Cholesterol Monitoring II, May 23, 2002, pp. 47-54.
Brown, J.Q et al., "Glucose micro- and nano-sensors based on nanoassembled enzyme/polymer/dye composites," Proceedings of SPIE, vol. 5325, Optical Diagnostics and Sensing IV, Jun. 18, 2004, pp. 21-30.
Brown, J.Q et al., "Core-Referenced Ratiometric Fluorescent Potassium Ion Sensors Using Self-Assembled Ultrathin Films on Europium Nanoparticles," IEEE Sensors Journal, vol. 5, Dec. 6, 2005, pp. 1197-1205.
Communication Pursuant to Article 94(3) EPC (Office Action) dated Jul. 8, 2021, in corresponding European Patent Application No. 17810793.4, 4 pages.
First Examination Report dated May 14, 2021, in corresponding Australian Patent Application No. 2017278240, 3 pages.
Notice of Reasons for Rejection (Office Action) dated Jun. 3, 2021, in corresponding Japanese Patent Application No. 2019-516090, with English translation, 11 pages.
Notice of Reasons for Refusal dated Jan. 31, 2022, issued in corresponding JP Application Mo. 2019-516090, filed Jun. 5, 2017, 3 pages.
Second Office Action dated Sep. 5, 2022, issued in the corresponding Chinese Application No. 2017800481319, filed on Jun. 5, 2017, and its English translation thereof.

* cited by examiner

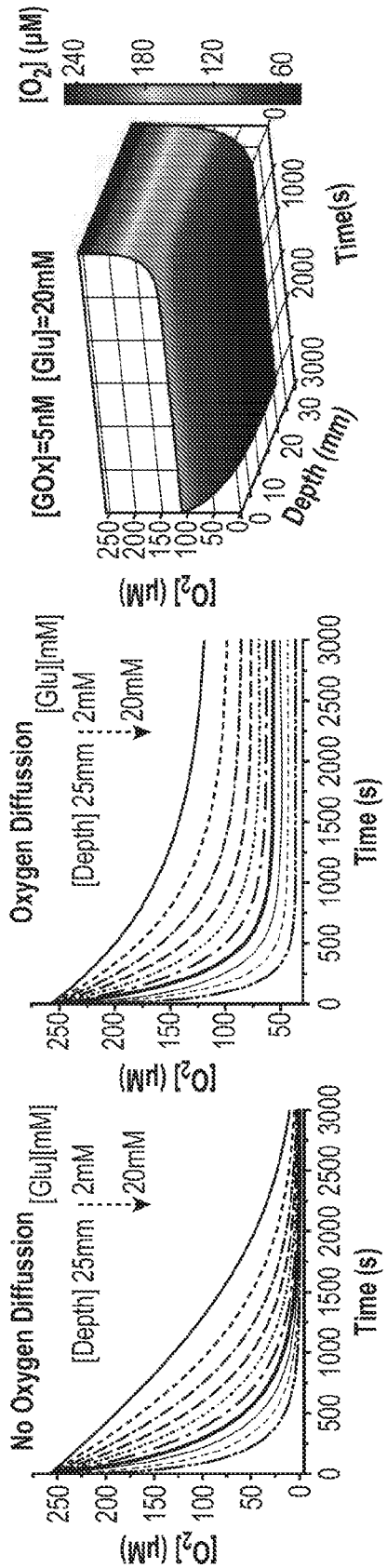
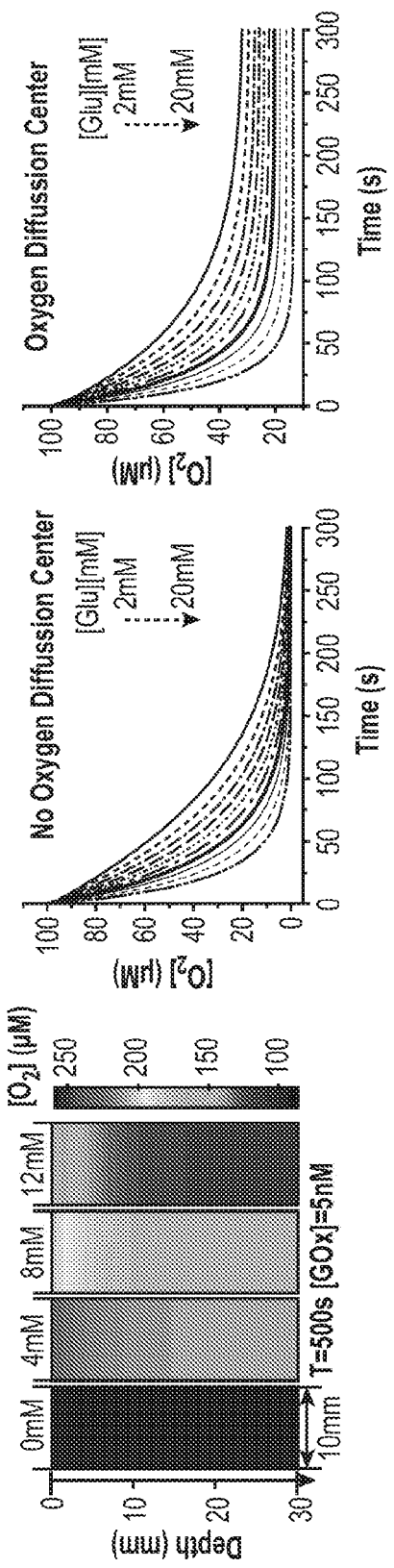
FIG. 1A  FIG. 1B  FIG. 1C
FIG. 1D  FIG. 1E  FIG. 1F

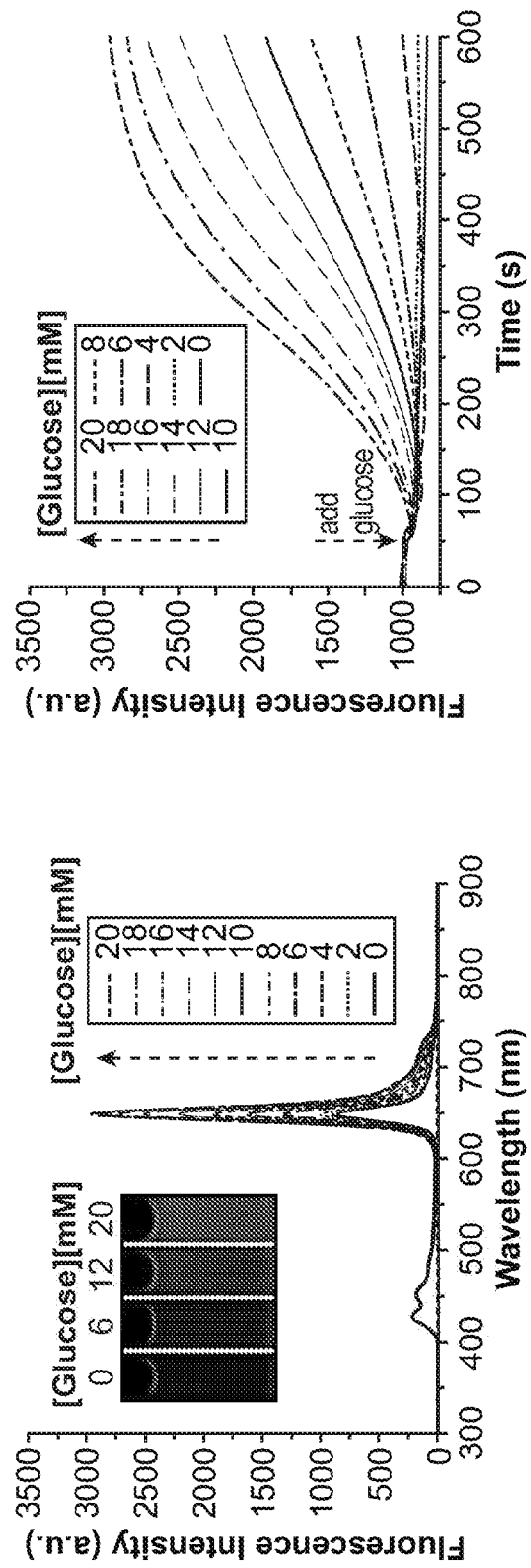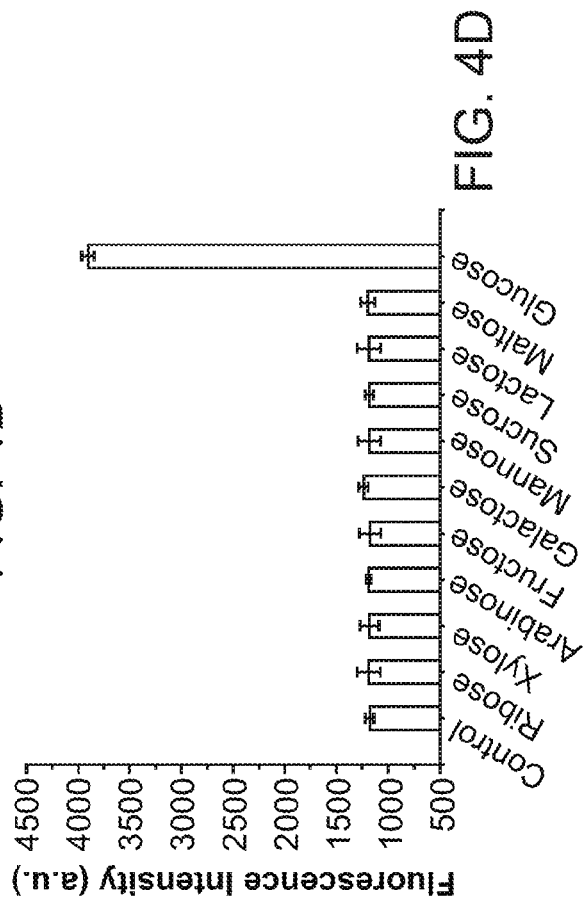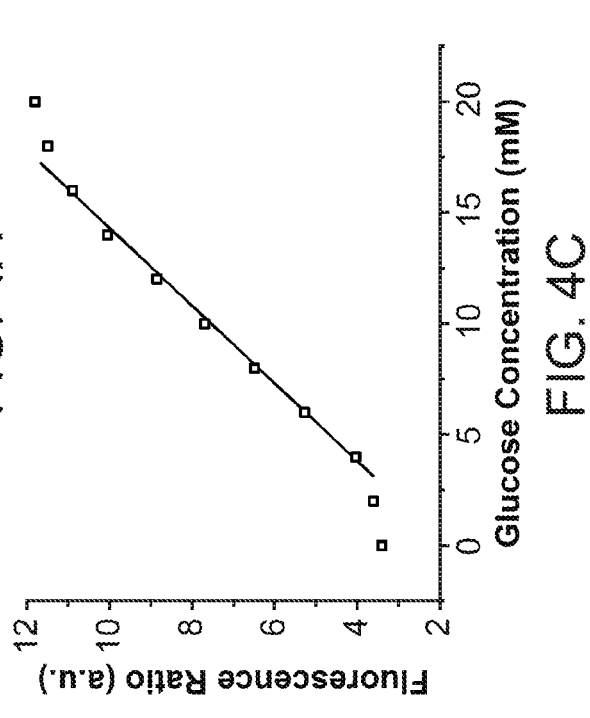

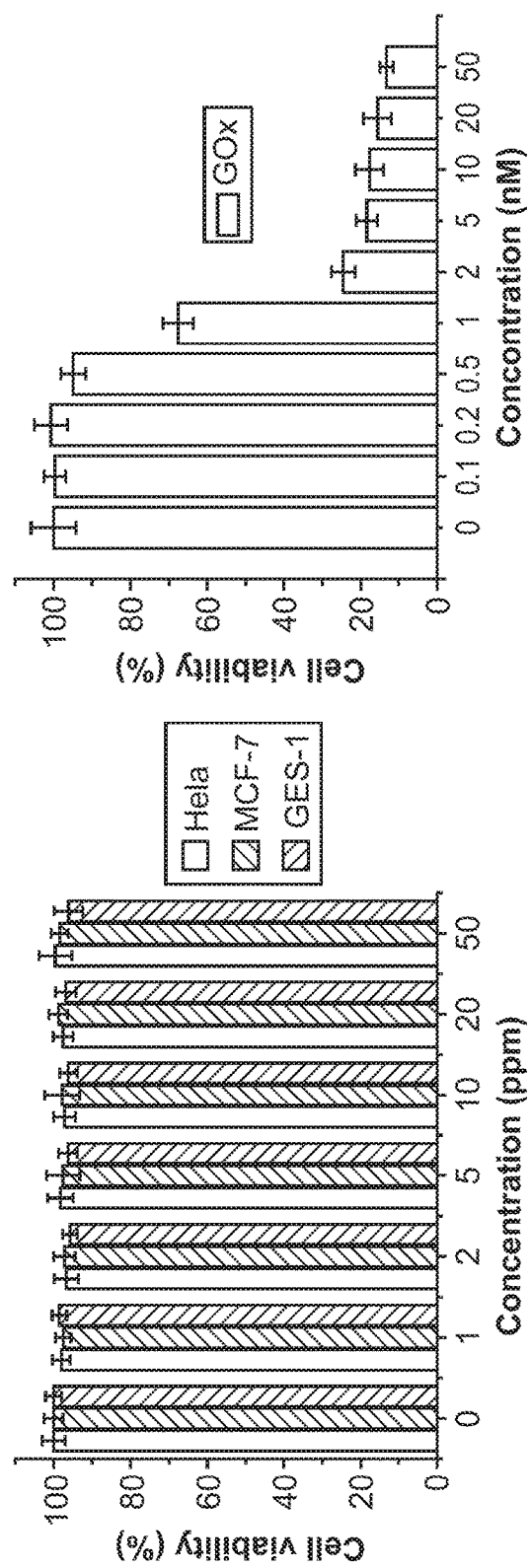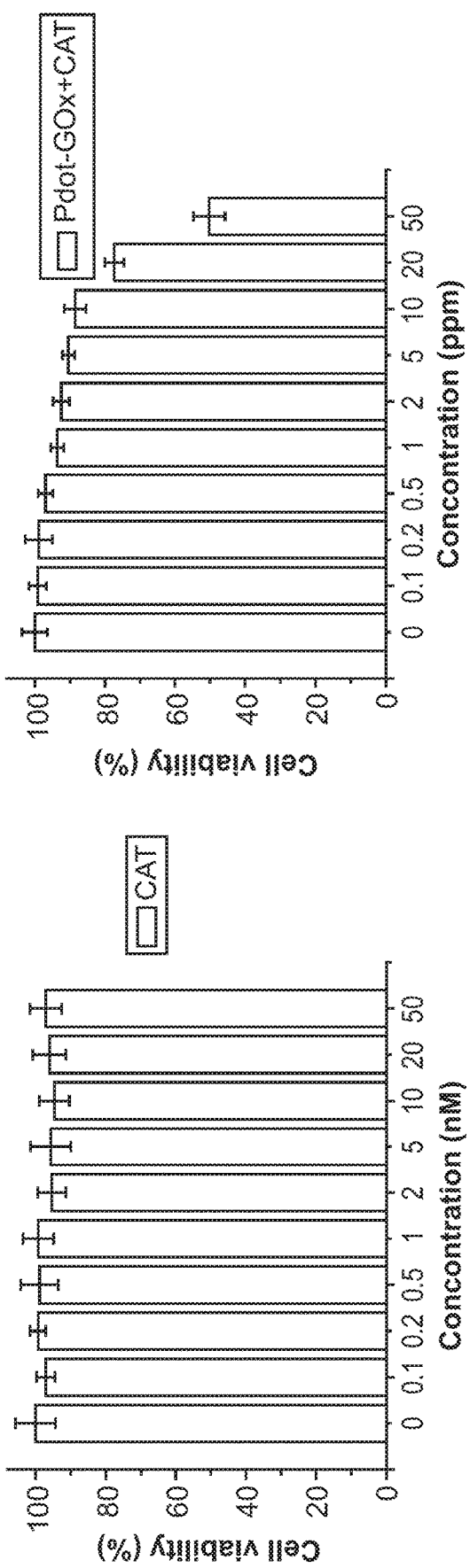

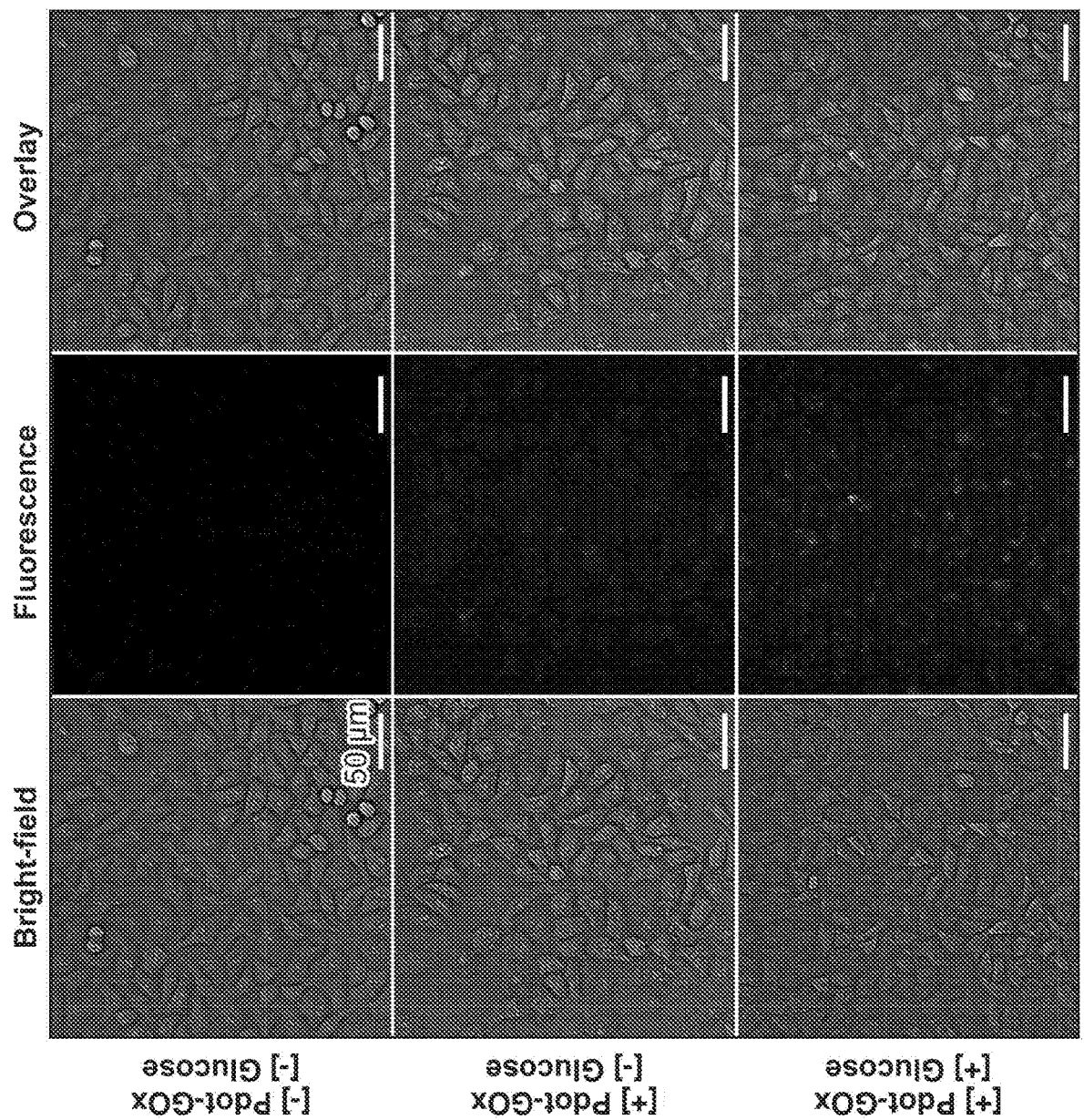

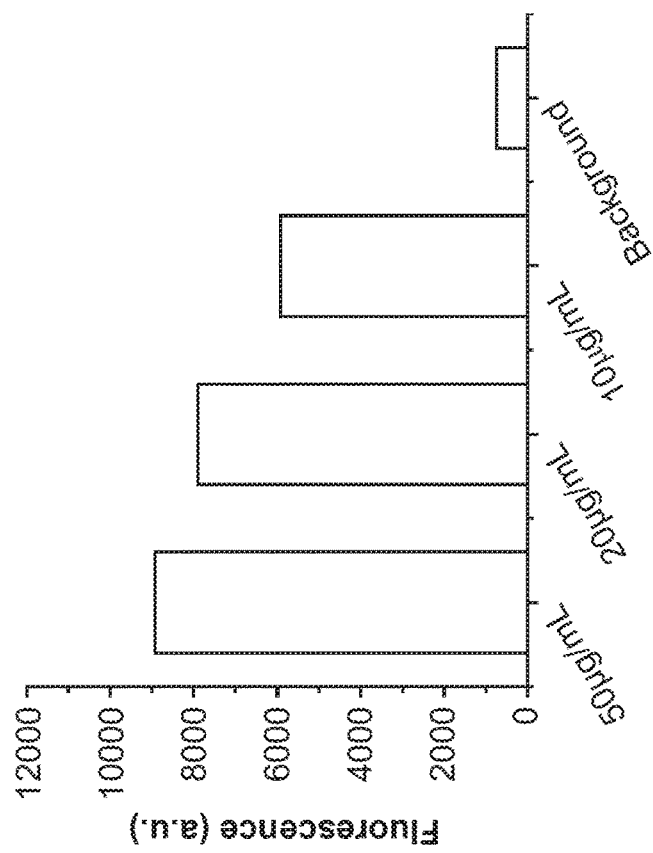
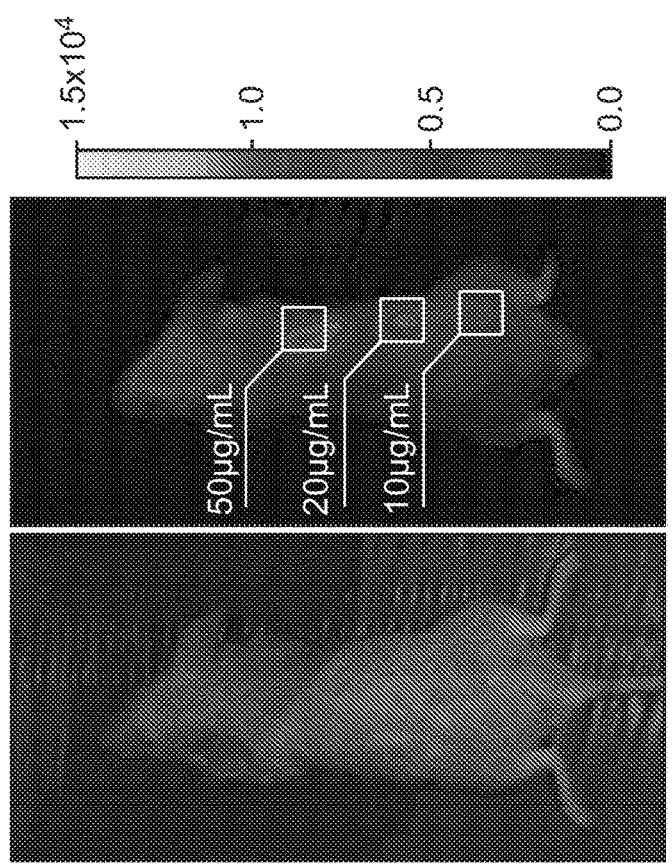
FIG. 8B
FIG. 8A

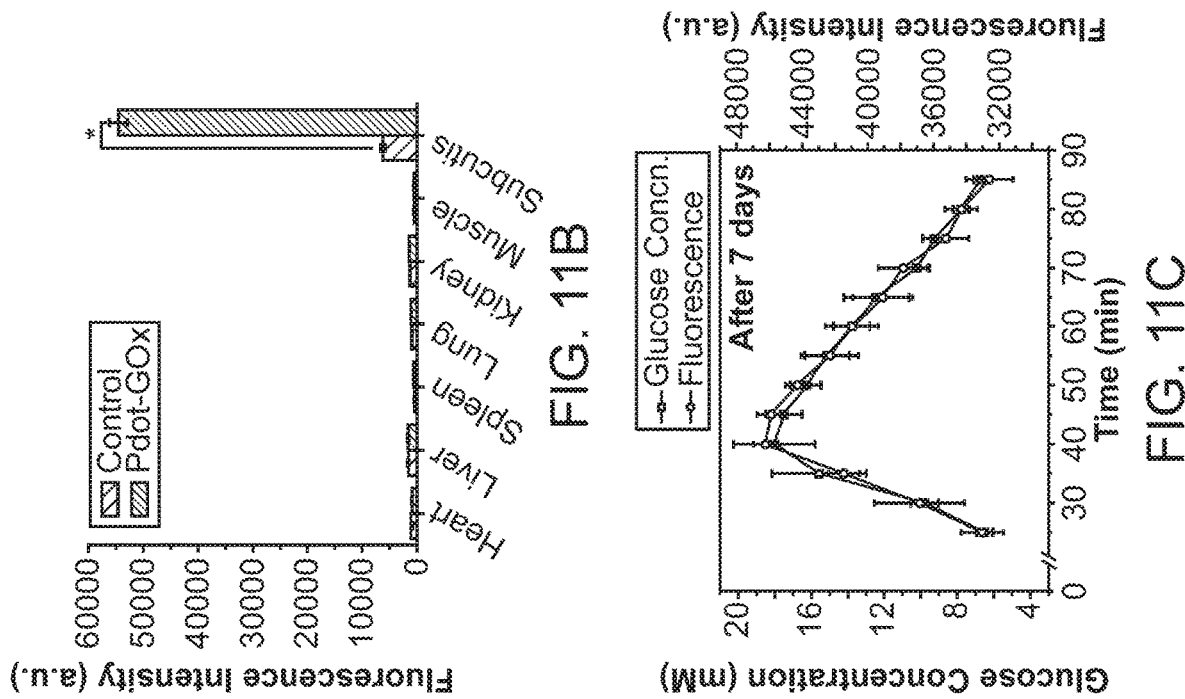
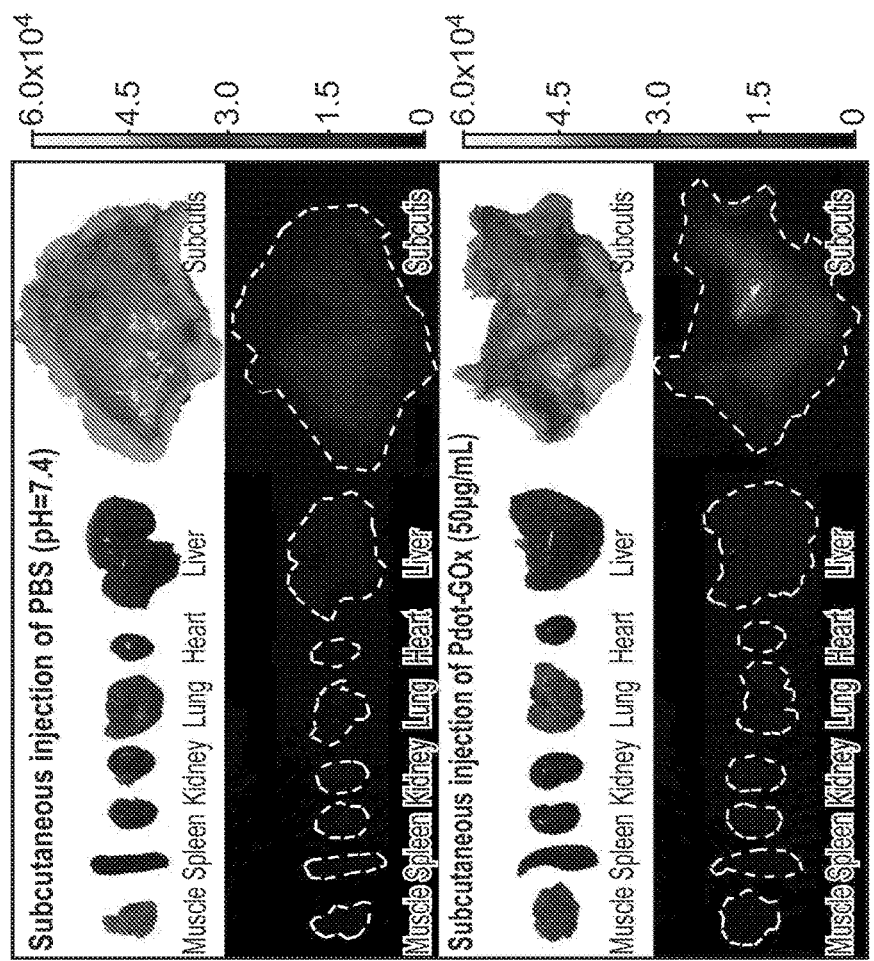
FIG. 11A
FIG. 11B
FIG. 11C

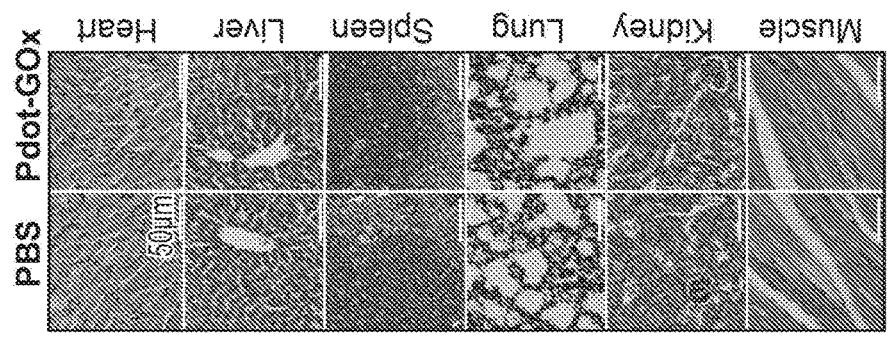
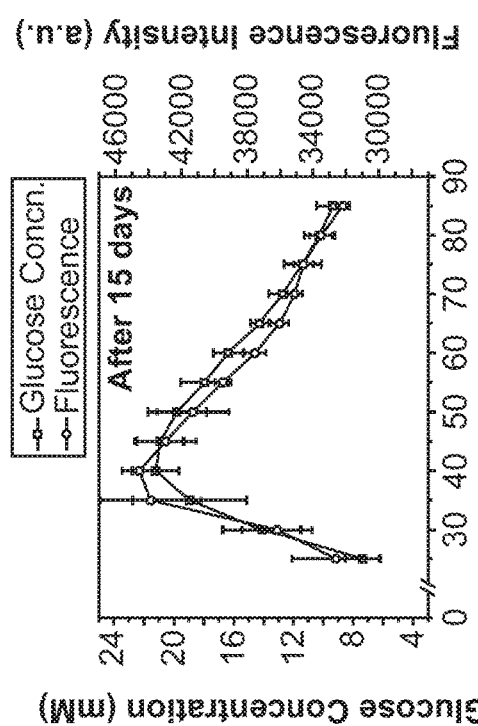
FIG. 11D
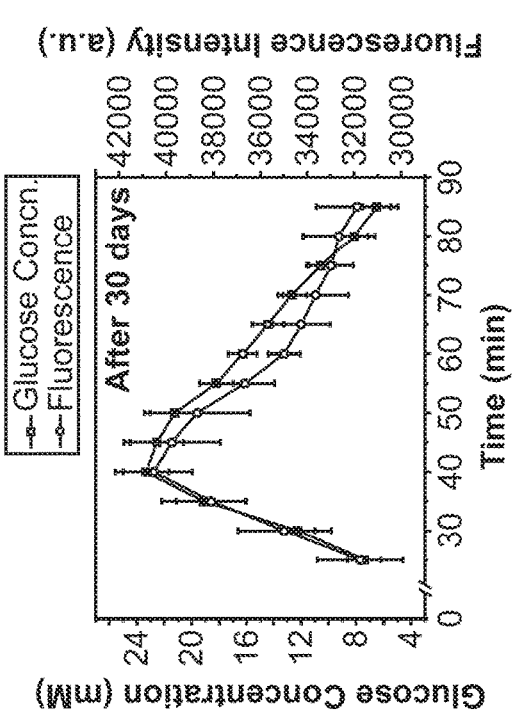
FIG. 11E
FIG. 11F

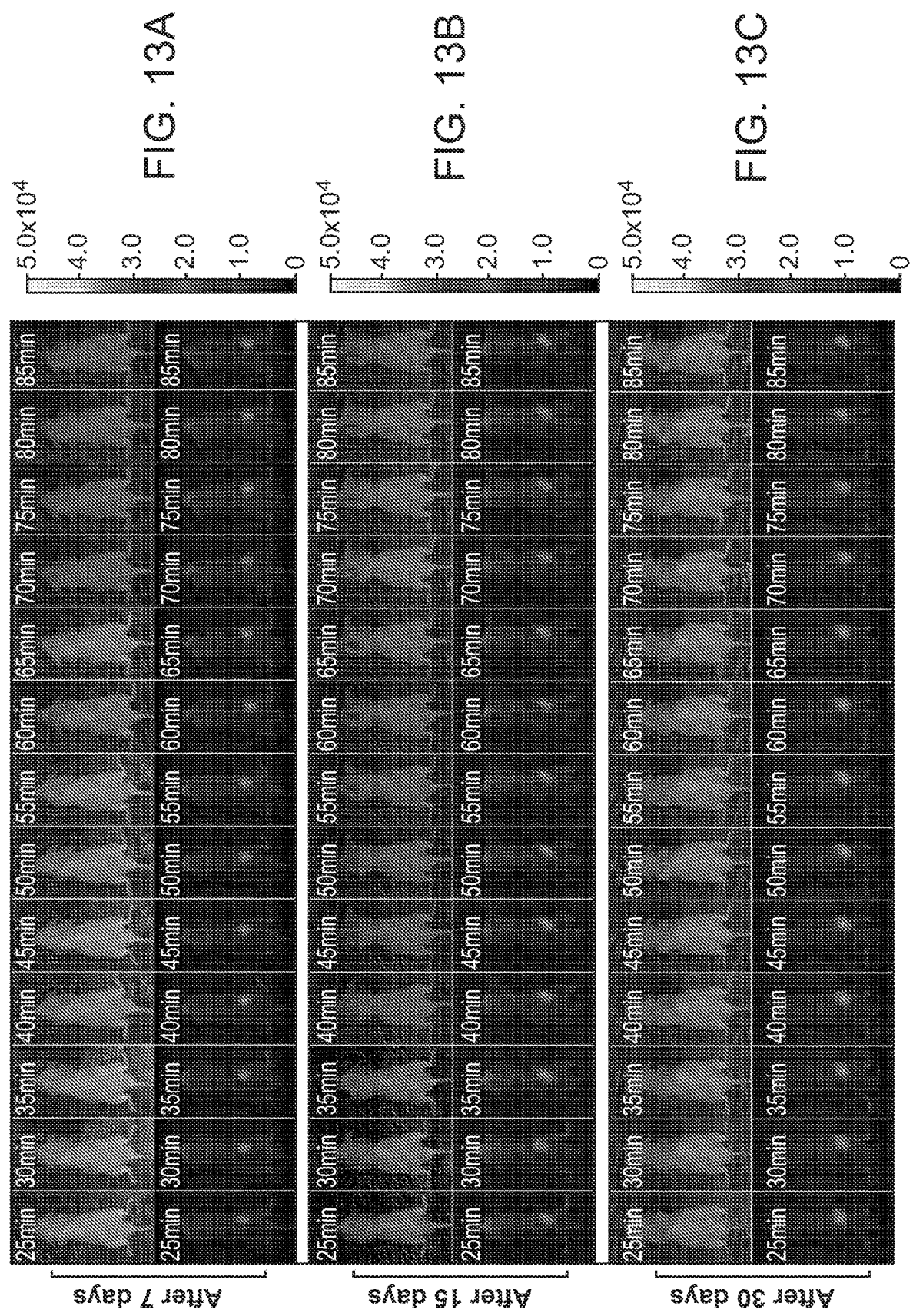

NANOPARTICLE TRANSDUCER SENSORS AND METHODS OF USE THEREOF

CROSS REFERENCE

This application is a U.S. National Phase Application under 35 U.S.C. § 371 of International Application No. PCT/US2017/035983, filed Jun. 5, 2017, which claims the benefit of International Patent Application No. PCT/CN2016/084986, filed Jun. 6, 2016, the contents of each of which are incorporated by reference in their entirety.

BACKGROUND

Measurement of the concentration of fluid constituents is important in medicine, biomedical research, and biotechnology. It is desirable, for example, to monitor the concentrations of various molecules in the blood of a patient, including small molecules. Indeed, small molecules play highly important roles in all aspects of life science because they are extensively involved in various cellular processes such as cell signaling, enzyme activity, and molecular transport. Advances in biology and medicine have led to identification of a vast number of small molecules implicated in human disease. In drug discovery, small molecules constitute a large yet fast-growing library of active drugs. Small molecules are also extensively used as research tools to probe biological function and assess emerging therapeutic agents.

The treatment of chronic diseases, such as diabetes, can require continual monitoring of one or more blood constituents, such as glucose, the concentrations of which can be dangerous when excessively high or low. Rapid and precise measurement of blood contents allows for the detection of undesirable variations in those contents as well as more efficient and responsive treatment of the underlying condition.

However, specific and sensitive detection of small molecules in a living system is highly challenging. Many prior methods of monitoring blood concentration require the removal of blood from the patient for external analysis, resulting in poor response speeds dependent on patient compliance, or the implantation of devices with poor biocompatibility or poor precision and sensitivity to blood concentration changes. Electrochemical transducers, for example, encounter intractable problems such as impaired responses and unpredictable signal drift, requiring the implanted electrodes of such transducers to be replaced frequently. Optical techniques, such as Raman techniques, have also been applied. However, Raman signals from small molecules tend to be weak and may easily be masked by intense overlapping from dominant biological species, although some unique Raman tags can generate signal in typical Raman-silent region of a cell. Therefore, it is highly challenging for in vivo real-time detection of intact small molecules such as amino acids, sugars, lipids, neurotransmitters, metabolites, and drug molecules.

Still greater problems arise in detection of large molecules such as proteins or nucleic acid chains, which require still greater measurement specificity due to their great number. In vivo, real time detection of such fluid constituents has heretofore proven generally impractical.

Thus, there is a need to provide improved sensors and methods for monitoring concentrations of fluid constituents with a high response rate, specificity, and sensitivity. The present disclosure addresses this need and more.

SUMMARY

The present disclosure provides transducer sensors and methods of using those sensors to monitor fluid constituent concentrations.

In various aspects, the present disclosure provides a nanoparticle transducer for particle-specific concentration measurements. The nanoparticle transducer comprises a nanoparticle comprising a chromophore and an enzyme. The enzyme is coupled to the nanoparticle. The enzyme is configured to catalyze a reaction. The reaction comprises a plurality of reaction elements, including one or more reactants and one or more products. The chromophore emits fluorescence in an amount determined by a concentration of a reaction element of the plurality of reaction elements.

Semiconducting Polymer dots (Pdots) have been developed as a new class of fluorescent nanoparticles. Compared to organic dyes and fluorescent proteins, Pdots can possess orders of magnitude greater brightness and are more resistant to photobleaching. When compared to quantum dots, for example, Pdots can be an order of magnitude brighter. Moreover, the dimensions of Pdots can be tuned from several to tens of nanometers without affecting their spectral properties. Pdots with small sizes are desirable in situations where labeling with large nanoparticles may perturb the native behavior of the tagged biomolecules. The small Pdots may also be useful in crowded cellular or intercellular spaces where they can better penetrate and distribute themselves. Various schemes have been developed to control the surface properties and bioconjugation of Pdots, which have provided use of Pdots for cell-surface and subcellular labeling. In addition, Pdot-based ratiometric sensors have been developed, including ones for pH, temperature, small molecules such as oxygen and hydrogen peroxide, and ions such as iron and copper.

In some aspects, the present disclosure provides a Pdot transducer for measurement of glucose concentrations. The Pdot transducer comprises a Pdot including a chromophore that emits fluorescence that is determined by a concentration of oxygen. Glucose oxidase is coupled to the Pdot. The glucose oxidase is configured to catalyze a reaction involving reaction elements. The reaction elements comprise glucose and oxygen as reactants. The chromophore fluoresces at a first fluorescence wavelength and a second fluorescence wavelength; the amount of fluorescence at the first fluorescence wavelength varies as a function of the oxygen concentration. The Pdot transducer thus comprises a fluorescence ratio equal to the ratio of the amount of fluorescence at the first fluorescence wavelength to the amount of fluorescence at the second fluorescence wavelength, and the fluorescence ratio is determined by the oxygen concentration. The oxygen concentration is affected by the reaction with glucose catalyzed by the enzyme; accordingly, the fluorescence ratio varies as a function of the glucose concentration, thereby providing a measurement of glucose concentration.

In various aspects, the present disclosure provides a method of determining the concentration of an analyte in a fluid. The method comprises contacting the fluid with a nanoparticle transducer as described herein and measuring fluorescence of the nanoparticle transducer. The method further comprises determining the concentration of the analyte in the fluid based on the measured fluorescence.

In various aspects, an apparatus for measuring the concentration of a target reactant in the blood is provided. The apparatus comprises a plurality of fluorescent nanoparticle transducers. The apparatus further comprises an optical sensor coupled to a processor and memory. The memory comprises instructions that, when executed, cause the processor to be configured to use the optical sensor to measure fluorescence emitted by the plurality of fluorescent nanoparticle transducers. The fluorescent nanoparticle transducers can be placed in a subdermal location in contact with fluid from a subject's blood. The optical sensor can be adapted to detect fluorescence transmitted through skin by the plurality of fluorescent nanoparticle transducers when the sensor is facing the skin.

In various aspects, the present disclosure provides a method of measuring a concentration of an analyte in a fluid. A Pdot is provided within the fluid. The Pdot comprises a chromophore, and the chromophore emits fluorescence in an amount determined by a concentration of a fluid component. The analyte causes a reaction in the fluid, and the reaction changes the concentration of the fluid component. The fluorescence emitted by the chromophore is measured, a concentration of the analyte in the fluid based on the measured fluorescence.

In various aspects, an artificial pancreas is provided comprising a glucose sensor employing a nanoparticle transducer, providing for a feedback loop to trigger dispensing of insulin for the maintenance of blood glucose concentrations within a predetermined range. In some aspects, the artificial pancreas is an implantable device, while in some aspects the artificial pancreas is configured for transdermal optical sensing of glucose concentrations and for injection of insulin. The artificial pancreas comprises a glucose-sensitive nanoparticle transducer, an illumination source, and a detector adapted to detect fluorescence at the nanoparticle emission wavelengths. The device further comprises a processor to determine blood glucose concentrations from the measured fluorescence and to regulate the dispensation of insulin from a storage chamber via an insulin pump to the patient. The detector, processor, and pump provide a feedback loop to maintain levels of blood glucose within a predetermined concentration range, which may optionally be user-adjustable. In some aspects, the device also comprises memory that stores a log of measured glucose levels as a function of time. In some aspects, the device comprises a transmitter to allow wireless communication with a mobile device and/or over a computer network. In some aspects, the nanoparticle transducer, the optical sensor, and the processor are integrated together, and placed in a subdermal location to detect fluorescence from the plurality of nanoparticle transducers in contact with fluid from a subject's blood. In some aspects, the integrated device comprising the nanoparticle transducer, the detector, and the processor in a subdermal location can have wireless communication through the skin with a mobile device and/or over a computer network.

The present disclosure provides sensitive detection and in vivo dynamic monitoring of analytes using optically bright transducers based on nanoparticles, such as semiconductor polymer dots (Pdots). Fluorescent Pdots are highly bright and versatile nanoparticle platforms for biological imaging and sensing applications. In certain aspects, oxygen-responsive Pdots are conjugated with oxygen-consuming enzyme on the surface to sensitively detect analytes in the form of small molecule substrates in biological environments. In certain aspects, the analyte is glucose. Analytical modeling and simulation of particular glucose-sensitive transducers disclosed herein based on enzymatic reaction rate constants and Fick's law of oxygen diffusion indicate that the small molecule at different concentrations can be well distinguished in typical tissue oxygen concentrations. Experimental results are also described, demonstrating intracellular glucose detection and long-term in vivo dynamic monitoring of blood glucose in mouse models. In consideration of a large library of oxygen-consuming enzymes, as well as other enzymes known to consume or generate suitable fluid components for which suitably sensitive fluorescent chromophores can be used, this approach can be generalized for in vivo detection of a wide range of small molecules, including amino acids, transmitters (e.g., neurotransmitters), metabolites, and pharmaceutical drugs, for example.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A through FIG. 1H illustrate simulated $O_2$ depletion kinetics and distribution profiles for an exemplary nanoparticle transducer for detection of glucose using an $O_2$-modulated signal from reactions catalyzed with glucose oxidase. FIG. 1A and FIG. 1B illustrate glucose induced $O_2$ depletion kinetics in a closed and an open cuvette, respectively. FIG. 1C illustrates a 3-D plot of temporal and spatial oxygen distribution for a system with 5 nM GOx and 20 mM glucose along the Z-axis of an open cuvette configuration. FIG. 1D illustrates oxygen distribution profiles in an open cuvette with different glucose concentrations at a time point of 500 seconds. FIG. 1E illustrates $O_2$ depletion kinetics in a closed tissue oxygen environment. FIG. 1F illustrates $O_2$ depletion kinetics in tissue with oxygen diffusion. FIG. 1G illustrates 2-D mapping of a circular configuration with oxygen diffusion at the time point of 20 seconds. FIG. 1H illustrates sensitivity of oxygen depletion for glucose determination with and without oxygen diffusion at the time point of 20 seconds.

FIG. 2A is a schematic illustration of the formation of Pdot-GOx bioconjugates for in vivo glucose monitoring. FIG. 2B illustrates hydrodynamic diameters of bare Pdots and Pdot-GOx. FIG. 2C illustrates zeta potentials of carboxyl Pdots and Pdot-GOx. FIG. 2D illustrates representative TEM images of carboxyl Pdots (left) and Pdot-GOx (right).

FIG. 3A illustrates the colloidal stability of the Pdot-GOx transducer over 30 days. FIG. 3B shows UV-vis absorption and photoluminescence spectra of the Pdot-GOx sensor.

FIG. 3C illustrates spectral overlap between fluorescence emission of polyfluorene nanoparticles (PDHF) and absorption of phosphorescent dye (PtOEP). FIG. 3D illustrates emission spectra of the undoped PDHF Pdots and PtOEP-doped Pdots with an excitation wavelength of 380 nm.

FIG. 4A through FIG. 4D illustrate spectroscopic properties of a Pdot-GOx nanoparticle transducer: FIG. 4A shows emission spectra of Pdot-GOx transducer at different glucose concentrations. FIG. 4B shows a ratiometric calibration plot ($I_{648}/I_{428}$) of the Pdot-GOx transducer as a function of glucose concentration. FIG. 4C illustrates response curves of the Pdot-GOx to glucose in aqueous suspensions. FIG. 4D illustrates the selectivity of the Pdot-GOx transducer for glucose over potential interfering carbohydrates.

FIG. 5A illustrates emission spectra of Pdots densely coated with GOx at various glucose concentrations. FIG. 5B shows a ratiometric calibration plot ($I_{648}/I_{428}$) of Pdot-GOx in the low analytical range.

FIG. 6A through FIG. 6D illustrate cell viability of HeLa cells treated with various materials including Pdot-GOx transducers. FIG. 6A through FIG. 6C show 24-hour cell viability for cells treated with varying concentrations of Pdot-GOx transducers, GOx, and catalase, respectively. FIG. 6D shows cells treated with both Pdot-GOx transducers and catalase in a ratio of about 1:6.

FIG. 7A through FIG. 7C illustrate intracellular glucose sensing in HeLa cells. FIG. 7A shows HeLa cells without Pdot-GOx incubation as a control group; FIG. 7B shows cells incubated with Pdot-GOx nanoparticles for 24 hours in a sugar-free medium; and FIG. 7C shows cells incubated with Pdot-GOx for 24 hours and supplemented with glucose for 4 hours.

FIG. 8A illustrates fluorescent imaging of a mouse subcutaneously with Pdot-GOx transducers. FIG. 8A illustrates fluorescent imaging of a mouse with three injection sites of Pdot-GOx transducers at different concentrations. FIG. 8B shows fluorescent intensity of the three different sites injected with Pdot-GOx.

FIG. 10A shows in vivo fluorescence imaging of varying glucose concentrations in a live mouse with injected Pdot-GOx. FIG. 10B shows in vivo fluorescence imaging of Pdot-GOx in a live mouse of a control group without administrations of glucose and insulin. FIG. 10C shows fluorescence intensities of an injected Pdot-GOx transducer in live mice and the glucose concentrations measured from blood samples from snipped tails. FIG. 10D shows fluorescence response of Pdot-GOx to blood glucose concentration in the control group without administrations of glucose and insulin.

FIG. 11A through FIG. 11F illustrate long-term glucose monitoring and in vivo distribution. FIG. 11A shows fluorescence images of excised organs and skin tissue of the mice subcutaneously injected with Pdot-GOx transducers (bottom) or sterilized, phosphate-buffered saline (top). FIG. 11B shows a quantification of the fluorescence intensity of Pdot-GOx distributed in organs and tissue harvested from the injected and control mice (*$P<0.05$). FIG. 11C through FIG. 11E show fluorescence intensity of the injected Pdot-GOx responsive to blood glucose concentration for 7 days, 15 days, and 30 days, respectively, after subcutaneous administration. FIG. 11F illustrates hematoxylin and eosin staining of organ sections excised from the mouse with the Pdot-GOx injection (right) and the control group with PBS injection (left).

FIG. 13A through FIG. 13C show fluorescence imaging of a live mouse at 7 days (FIG. 13A), 15 days (FIG. 13B), and 30 days (FIG. 13C) after injection with nanoparticle transducers.

FIG. 14A shows pictures of a mouse subcutaneously injected with Pdot-GOx under UV light (385 nm).

FIG. 15A shows emission spectra for a plurality of glucose concentrations. FIG. 15B shows a calibration plot of said transducers detecting glucose over a range of concentrations from 0 to about 20 mM, showing a ratiometric response curve throughout the range.

FIG. 16A shows emission spectra for a plurality of glucose concentrations. FIG. 16B shows a calibration plot of said transducers detecting glucose over a range of concentrations from 0 to about 20 mM, showing a ratiometric response curve.

FIG. 17A shows emission spectra for a plurality of glucose concentrations. FIG. 17B shows a calibration plot of said transducers detecting glucose over a range of concentrations from 0 to about 20 mM, showing a ratiometric response curve.

FIG. 18A shows emission spectra for a plurality of ascorbic acid concentrations. FIG. 18B shows a calibration plot of said transducers detecting ascorbic acid over a range of concentrations from about 2 to about 20 mM, showing a ratiometric response curve throughout the range.

FIG. 19A illustrates fluorescence intensities of the injected nanoparticle sensors in live mice with the administration of different concentrations of ascorbic acid. FIG. 19B shows in vivo fluorescence imaging of varying ascorbic acid concentrations in a live mouse with injected Pdot sensors.

FIG. 20A shows the kinetic change of fluorescence emission spectra of injected Pdots in a live mouse to blood concentration of ascorbic acid, under excitation at 385 nm. FIG. 20B shows fluorescence intensity response as a function of time to blood concentration of ascorbic acid after intravenous administration thereof.

DETAILED DESCRIPTION

Figures 1G, 1H:
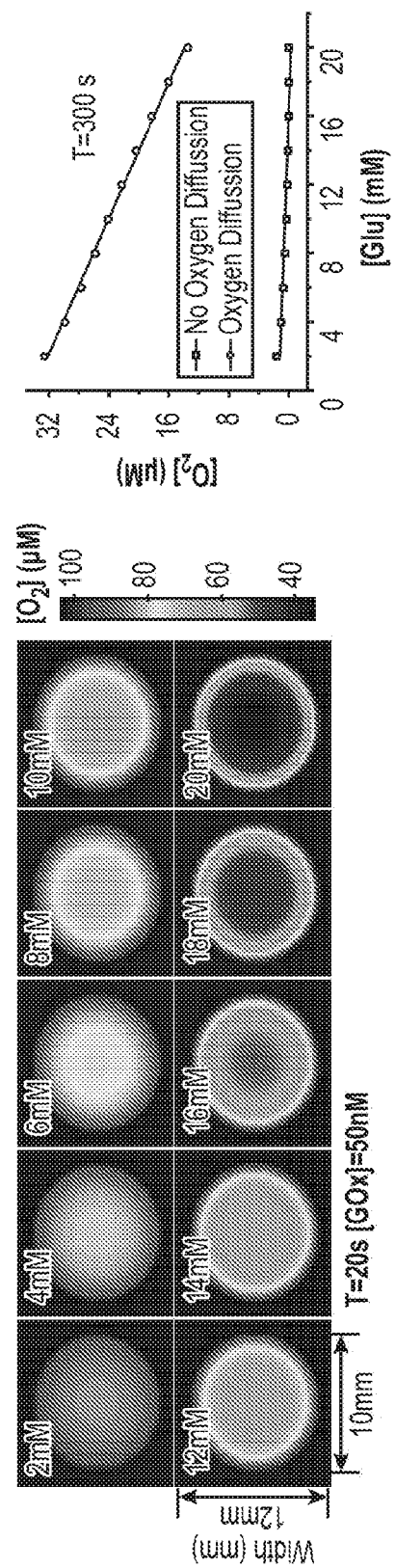

The present disclosure relates generally to apparatus, compositions, systems, and methods for monitoring the concentration of analytes in fluids using nanoparticle transducers. In many aspects, the analyte is a molecule in the fluid. In many aspects, the fluid is blood; for example, the compositions, systems, and methods disclosed herein are useful for monitoring the concentration of one or more selected molecules in the blood of a subject. In many aspects, the fluid is tears; for example, the compositions, systems, and methods disclosed herein are useful for monitoring the concentration of one or more selected molecules in the tear of a subject. In many aspects, the fluid is sweat; for example, the compositions, systems, and methods disclosed herein are useful for monitoring the concentration of one or more selected molecules in the sweat of a subject. In many aspects, the fluid is saliva; for example, the compositions, systems, and methods disclosed herein are useful for monitoring the concentration of one or more selected molecules in the saliva of a subject. In many aspects, the fluid is lymph fluid; for example, the compositions, systems, and methods disclosed herein are useful for monitoring the concentration of one or more selected molecules in the lymph fluids of a subject. In many aspects, the fluid is spinal fluid; for example, the compositions, systems, and methods disclosed herein are useful for monitoring the concentration of one or more selected molecules in the spinal fluid of a subject. In many aspects, the fluid is urine; for example, the compositions, systems, and methods disclosed herein are useful for monitoring the concentration of one or more selected molecules in the urine of a subject.

As used herein, the term "polymer dot" or "Pdot" refers to a particle structure including one or more semiconducting polymers collapsed to form a stable sub-micron sized particle, e.g., a nanoparticle. In some aspects, the polymer dots are highly fluorescent nanoparticles with emissions tunable, e.g., from the visible to the near IR region. The polymer dots can include chromophoric polymers that can, e.g., absorb light and then emit light by fluorescence. In some embodiments, the polymer dots include at least one condensed polymer, e.g., a semiconducting polymer. For polymer dots having more than one condensed polymer (e.g., more than one semiconducting polymer), the condensed polymers can be the same or different types of polymers. For example, a Pdot can comprise both semiconducting polymers and non-semiconducting polymers.

A nanoparticle transducer to monitor a selected analyte may be assembled from an appropriate choice of an enzyme, a nanoparticle, and a chromophore. The enzyme can be chosen as an enzyme that catalyzes a reaction involving the analyte, such that the concentration of the analyte can affect the rate of the reaction. The reaction can involve a plurality of reaction elements, including reactants and products. The enzyme can be selected such that each reactant of its catalyzed reaction is present in the fluid to be analyzed. The chromophore can be chosen such that fluorescence of the chromophore is determined by the concentration of a reactant or product of the reaction catalyzed by the enzyme. The nanoparticle can be chosen to allow both the enzyme and the chromophore to be incorporated into or conjugated with the nanoparticle. For example, the nanoparticle can be a Pdot, allowing the enzyme to be covalently bonded to the Pdot and the chromophore to be incorporated into and/or covalently bonded to the Pdot. In some cases, the chromophore can comprise all or substantially all of the nanoparticle; for example, a Pdot may be made entirely or substantially entirely of one or more chromophores, in some cases.

In many aspects, the enzyme, chromophore and nanoparticle can be selected from a set of potential enzymes, chromophores, and nanoparticles to create a nanoparticle transducer to detect a given analyte as follows: From a set of enzymes, select those that catalyze a reaction wherein the analyte is a reactant. For each such reaction, identify the other reaction elements whose concentrations will change as a result of the reaction taking place—for example, each time the reaction takes place, reactant concentrations fall and product concentrations rise (for a reversible reaction, the reverse of the reaction causes the opposite effect). From those reaction elements, for each enzyme, identify a corresponding chromophore from the set of chromophores that has its amount of fluorescence change in response to changes in concentration of one of the reaction products. If no chromophore matches, eliminate the enzyme. From those enzyme/chromophore pairs remaining, select one such pair and choose a nanoparticle, such as a Pdot, to which each can be coupled and/or incorporated, thereby choosing elements to construct a nanoparticle transducer. A second chromophore that emits at a different wavelength and does not change its intensity in response to any reaction elements can be selected from the list of chromophores to serve as a control chromophore. Alternatively, if the originally selected chromophore emits fluorescence both at a wavelength that changes intensity in response to reactant or product concentration and at a different wavelength that does not change intensity, then that single chromophore can serve as its own control.

In many aspects, the nanoparticle transducers described herein comprise an enzyme catalyzing a reaction involving an analyte. The reaction has reaction elements including reactants and products, one of which is the analyte. The nanoparticle comprises a chromophore that emits fluorescence at one or more wavelengths in response to illumination with a light beam. The amount of fluorescence at at least one of the wavelengths depends on the concentration of a molecule of the reactants or products other than the analyte. The enzyme and the chromophore of the nanoparticle are in proximity; accordingly, as the reaction catalyzed by the enzyme consumes reactants and produces products, the respective concentrations of said reactants and products changes, with reactant concentrations decreasing and product concentrations increasing. The presence of the analyte at elevated concentration causes the reaction to proceed more quickly than at low concentration, so the presence of the analyte results in relatively high product concentrations and relatively low reactant concentrations. Because the amount of fluorescence of the chromophore depends on one of the reactants or products, the amount of fluorescence from the chromophore affects the amount of fluorescence of the chromophore by changing the concentrations of the other reaction elements as the reaction takes place. Accordingly, the enzyme and the chromophore of the nanoparticle, together, act as a transducer, transforming variations in analyte concentration to variations in fluorescence. In some aspects, the fluorescence intensity of one wavelength emission of the transducer is used to determine the analyte concentrations. In some aspects, the fluorescence intensity ratio at two wavelength emissions of the transducer is used to determine the analyte concentrations. This fluorescence can easily be measured in a wavelength-selective manner to determine the analyte's concentration from a signal of an optical sensor.

In some aspects, the nanoparticle comprises a semiconducting polymer that emits fluorescence at one or more wavelengths in response to illumination with a light beam. The amount of fluorescence at least one of the wavelengths depends on the concentration of a molecule of the reactants or products other than the analyte. In some cases, the nanoparticle comprises a semiconducting polymer and a dye that emits fluorescence at one or more wavelengths. The dye can be physically doped or chemically attached to the semiconducting polymer to form nanoparticles. The semiconducting polymer can have energy transfer to the dye to enhance or amplify the fluorescence intensity of the dye.

In many aspects, the fluid described herein is fluid within the body of a subject, such as blood, sweat, tears, lymph fluid, spinal fluid, urine, saliva, or other fluids within body tissues or secreted by body tissues. The subject can be an animal, and in many aspects, the subject is a human.

Various aspects of the present disclosure provide chromophores having characteristics that are advantageous for efficient and accurate measurement of analyte concentrations using the nanoparticle transducers provided herein. Examples of such characteristics include but are not limited to: (1) high brightness so the transducer signal can be easily detected and recovered; (2) high sensitivity to a reaction element of the reaction catalyzed by the enzyme; (3) high absorption cross-section so the nanoparticle transducer fluorescence can be easily induced without requiring intense energy application; (4) good stability (e.g., thermostability) so the nanoparticle transducers can remain active for long time periods in vivo; (5) wavelengths capable of being detected and differentiated, including transdermally in some cases; and/or (6) good fatigue resistance for to decrease degradation when used for continuous analyte monitoring. In certain aspects, the chromophores of the nanoparticle transducers described in the present disclosure include some or all of these characteristics.

For instance, the present disclosure provides in some aspects nanoparticle transducers exhibiting signal fluorescent emission intensity at a peak emission wavelength that varies as a function of the concentration of a fluid constituent. The nanoparticle transducer can also comprise a chromophore with a different, control emission intensity at the peak emission wavelength that does not substantially vary in response to the concentration of the fluid constituent. In certain aspects, the peak emission wavelength is within a range from about 200 nanometers to about 300 nanometers, about 250 nanometers to about 350 nanometers, about 300 nanometers to about 400 nanometers, about 350 nanometers to about 450 nanometers, about 400 nanometers to about 500 nanometers, about 450 nanometers to about 550 nanometers, about 500 nanometers to about 600 nanometers, about 550 nanometers to about 650 nanometers, about 600 nanometers to about 700 nanometers, about 650 nanometers to about 750 nanometers, about 700 nanometers to about 800 nanometers, about 750 nanometers to about 850 nanometers, about 800 nanometers to about 900 nanometers, about 850 nanometers to about 950 nanometers, about 900 nanometers to about 1000 nanometers, about 950 nanometers to about 1050 nanometers, about 1000 nanometers to about 1100 nanometers, about 1150 nanometers to about 1250 nanometers, or about 1200 nanometers to about 1300 nanometers.

As another example, some aspects of the present disclosure provide nanoparticle transducers exhibiting sufficient stability for long term in vivo analyte concentration monitoring, e.g., the nanoparticle transducers are capable of being stably detecting analyte concentration for an extended period of time without substantial degradation. In various aspects, stability of the nanoparticle transducers is advantageous in ensuring that said transducers can be used in vivo for long time periods without need for replacement. In some aspects, a population of nanoparticle transducers is considered to be "stable" if at least 50%, at least 60%, at least 70%, at least 75%, at least 80%, at least 85%, at least 90%, at least 95%, at least 99%, at least 99.5% or at least 99.95% of the nanoparticle transducers in the population retain the ability to modulate fluorescence in response to analyte concentration variation for the specified time period. In some aspects, a nanoparticle transducer is considered to be "stable" if the emission intensity of the nanoparticle transducer retains the ability to measure analyte concentration variation for the specified time period. In some aspects, a nanoparticle transducers is considered to be "stable" if the intensity ratio of two emission peaks retain the ability to measure analyte concentration variation for the specified time period, even though the absolute emission intensity can be significantly decreased. In some aspects, a nanoparticle transducer is considered to be stable if the time constant (e.g., time to decay to 1/e of the fluorescence signal strength) is at least about 3 hours, about 6 hours, about 12 hours, about 24 hours, about 1 day, about 2 days, about 4 days, about 10 days, about 20 days, about 30 days, about 1 month, about 2 months, about 4 months, about 6 months, about 1 year, or more. In some aspects, the nanoparticle transducers maintain sufficient signal intensity that analyte detection can be reliably performed throughout the specified time period.

In some aspects of the present disclosure, the chromophore emission spectrum is selected or designed to exhibit narrow band emission properties at the peak emission wavelength so as to reduce or minimize overlap with other emission sources. For example, in certain aspects, the chromophore has a peak emission bandwidth (e.g., full width at half maximum (FWHM) of the emission peak) of no more than about 5 nanometers, about 10 nanometers, about 15 nanometers, about 20 nanometers, about 25 nanometers, about 30 nanometers, about 35 nanometers, about 40 nanometers, about 45 nanometers, about 50 nanometers, about 60 nanometers, about 70 nanometers, about 80 nanometers, about 90 nanometers, or about 100 nanometers.

Chromophore Compositions

Various types of chromophores are suitable for use with the methods and systems of the present disclosure, including but not limited to dyes, stains, proteins, polymers, beads, particles, or combinations thereof. In some aspects, the nanoparticle transducer includes one or more chromophores (e.g., fluorophores). The chromophores described herein can be used to produce nanoparticle transducers according to various mechanisms. In some aspects, the nanoparticle comprises a semiconducting polymer that emits fluorescence at one or more wavelengths in response to illumination with a light beam. The amount of fluorescence of the semiconducting polymer can depend on the concentration of a molecule of the reactants or products. In some aspects, the nanoparticle comprises a semiconducting polymer and a dye that emits fluorescence at one or more wavelengths. The amount of fluorescence of the dye depends on the concentration of a molecule of the reactants or products. The dye can be physically doped or chemically attached to the semiconducting polymer for forming nanoparticles. The chromophoric polymer can have energy transfer to the dye to enhance or amplify the fluorescence intensity of the dye.

In some aspects, a nanoparticle transducer includes at least one chromophoric, semiconducting polymer particle (also known as "polymer dot" or "Pdot") comprising one or more polymers (e.g., semiconducting polymers, non-semiconducting polymers, or a combination thereof) that have been collapsed into a stable sub-micron-sized particle. Semiconducting polymer particles are advantageous in certain aspects compared to other types of chromophores for several reasons: (1) they are extremely bright, up to 30 times brighter than quantum dots, and exceptionally photostable; (2) they have fast photon emission rates, often with sub-nanosecond lifetimes so they are well-suited for fast optical detection; (3) they possess good biocompatibility and are not composed of cytotoxic heavy metals like quantum dots; (4) they exhibit amplified energy transfer so their fluorescence emission can be well-modulated, e.g., by photochromic molecules via energy transfer.

Various structures and compositions of chromophoric polymer particles are applicable to the aspects presented herein. The chromophoric polymer particles provided herein are made up of a single polymer or, alternatively, comprise blends of polymers. In certain aspects, the one or more polymers are collapsed, precipitated, and/or condensed to form a polymer matrix. In some aspects, the properties of the chromophoric polymer particle are dependent on the structure and/or properties of the constituent polymer(s). Therefore, the polymer backbone (main chain), side chains, terminal units, and substituted groups are varied in certain aspects to obtain specific properties. In some aspects, the optical properties of the chromophoric polymer particle are tuned by varying the structures of the polymer backbone (main chain).

In some aspects, the chromophoric polymer particles provided herein include one or more chromophores, also referred to herein as chromophoric units. In certain aspects, a chromophore absorbs certain wavelengths of light, e.g., from the UV region to the near infrared region, and may be or may not be emissive. In some aspects, a chromophoric unit includes, but is not limited to, a unit of structures with delocalized pi-electrons, a unit of small organic dye molecules, and/or a unit of metal complexes. In various aspects, the chromophore is part of the polymer matrix or is incorporated into the polymer matrix, e.g., by blending, cross-linking, and the like. In some aspects, the chromophoric polymer is a semiconducting polymer.

In certain aspects, the chromophoric polymer particles of the present disclosure include one or more chromophoric polymers. In some aspects, a chromophoric polymer includes at least a portion which absorbs certain wavelengths of light, e.g., ranging from UV to near infrared spectra. Chromophoric polymers according to the present disclosure may be or may not be emissive. In some aspects, a chromophoric polymer includes one or more chromophoric units. Examples of chromophoric polymers include but are not limited to polymers comprising units of structures with delocalized pi-electrons (e.g., semiconducting polymers), polymers comprising units of small organic dye molecules, polymers comprising units of metal complexes, and polymers comprising units of any combinations thereof. In some aspects, the chromophoric unit is incorporated into the polymer backbone. In some aspects, the chromophoric unit is covalently attached to the side chain, or the terminal unit of the polymer. Chromophoric polymers are made using standard synthesis methods generally well known in the art, in certain aspects.

Various types of chromophoric polymer particles are suitable for use as a platform for the optical marking approaches of the present disclosure. Chromophoric polymer particles can adopt a variety of configurations, including but not limited to a monolithic polymer particle having a uniform, homogenous composition or a polymer particle having a distinct core and cap structure. The chromophoric polymer particles provided herein can be formed by any method known in the art, including, without limitation, methods relying on precipitation, methods relying on the formation of emulsions (e.g., mini or micro emulsion), and methods relying on condensation. Examples of chromophoric polymer particles suitable for use with the techniques described herein can be found in, for example, PCT application numbers PCT/US2010/056079, PCT/US2012/071767, PCT/US2011/056768, PCT/US2013/024300, and PCT/US2013/063917 and in U.S. Patent Publication No. 2013/0266957, each of which is incorporated herein by reference.

In some aspects, the chromophoric polymer particle is a nanoparticle. In some aspects, the sizes of the nanoparticles provided herein are defined in terms of a "critical dimension," which refers to the smallest dimension of the nanoparticle. Some nanoparticles are roughly spherical in shape, which results in the critical dimension being the diameter of the spherical particle. In some aspects, certain nanoparticles, such as nanospheres and nanocubes, are completely nanoscopic in size. In some aspects, not every dimension of a nanoparticle is at the nanoscale. For example, a nanocylinder can have a diameter on the nano-scale but a length on the micro-scale. A wide variety of nanoparticle shapes are applicable to the aspects described herein, including but not limited to a sphere, a cylinder, an ellipsoid, a polyhedron, a prism, a rod, a wire, or combinations thereof. The shape of the nanoparticle contributes to the optical properties in certain aspects, as will be appreciated by those of skill in the art (e.g., nano-rods may have different optical properties than nano-spheres).

In some aspects, the typical size of a chromophoric polymer particle is fewer than 100 nanometers. In certain aspects, a colloidal polymer nanoparticle is composed of a lyophobic polymer interior. Optionally, polyelectrolytes can also be formed into nanoparticles. In certain aspects, the chromophoric polymer particle comprises at least one chromophoric polymer that has been formed into a stable particle. The particle size can vary from 5 nanometers to 500 nanometers, for example. In some aspects, the critical dimension (e.g., diameter) of the particle is less than 1,000 nanometers, less than 700 nanometers, less than 500 nanometers, less than 400 nanometers, less than 300 nanometers, less than 200 nanometers, less than 100 nanometers, less than 50 nanometers, less than 40 nanometers. In some aspects, the critical dimension of the particle is less than 30 nanometers, less than 20 nanometers, or less than 10 nanometers.

In some aspects, the chromophoric polymer particles described herein include a polymer matrix formed from one or more chromophoric polymers. Any suitable number and combination of chromophoric polymer types can be incorporated in the chromophoric polymer particles described herein, such as one or more chromophoric polymers, two or more chromophoric polymers, three or more chromophoric polymers, four or more chromophoric polymers, five or more chromophoric polymers, six or more chromophoric polymers, seven or more chromophoric polymers, eight or more chromophoric polymers, nine or more chromophoric polymers, ten or more chromophoric polymers, fifty or more chromophoric polymers, or one hundred or more chromophoric polymers. The mass concentration of the chromophoric polymers relative to the entire chromophoric polymer particle mass can be varied from 1% to 99%, 10% and 99%, 20% and 99%, 30% and 99%, 40% and 99%, or 50% and 99%.

Various types and compositions of chromophoric polymers are applicable for use in accordance with aspects of the present disclosure. The chromophoric polymer can be a homopolymer or a heteropolymer. In various aspects, the chromophoric polymer is a semiconducting polymer, a non-semiconducting polymer, or a combination thereof. For example, a number of semiconducting polymers are suitable for use in chromophoric polymer particles according to the present disclosure. Examples of semiconducting polymers include but are not limited to: polyfluorene-based polymers, including but not limited to poly(9,9-dihexylfluorenyl-2,7-diyl) (PDHF)-based and poly(9,9-dioctylfluorenyl-2,7-diyl) (PFO)-based; fluorene-based copolymers, including but not limited to, poly[{9,9-dioctyl-2,7-divinylene-fluorenylene}-alt-co-{2-methoxy-5-(2-ethylhexyloxy)-1,4-phenylene}] (PFPV)-based, poly[(9,9-dioctylfluorenyl-2,7-diyl)-co-(1,4-benzo-{2,1,3}-thiadiazole)] (PFBT)-based, poly[(9,9-dioctylfluorenyl-2,7-diyl)-co-(4,7-Di-2-thienyl-2,1,3-benzothiadiazole)] (PFTBT)-based, and poly[(9,9-dioctylfluorenyl-2,7-diyl)-co-(4,7-Di-2-thienyl-2,1,3-benzothiadiazole)] (PF-0.1TBT)-based; phenylene vinylene polymers, including but not limited to, poly[2-methoxy-5-(2-ethylhexyloxy)-1,4-phenylenevinylene] (MEH-PPV)-based and poly[2-methoxy-5-(2-ethylhexyloxy)-1,4-(1-cyanovinylene-1,4-phenylene)] (CN-PPV)-based semiconducting polymers; phenylene ethynylene-based polymers, including but not limited to, poly(2,5-di(3',7'-dimethyloctyl)phenylene-1,4-ethynylene (PPE)-based semiconducting polymers; BODIPY based semiconducting polymer; squaraine based semiconducting polymer; or a combination thereof.

A wide variety of chromophoric polymer structures are suitable for use in accordance with various aspects of the present disclosure. In some aspects, the chromophoric polymer is a linear polymer. In other aspects, the chromophoric polymer is a branched polymer. In certain aspects, the chromophoric polymer is a dendrimer. In certain aspects, the chromophoric polymer is a brush polymer. In certain aspects, the chromophoric polymer is a star polymer.

In some aspects, the chromophoric polymer particles described herein contain a polystyrene-based, comb-like polymer. Non-limiting examples of polystyrene based comb-like polymers include polystyrene graft acrylic acid, polystyrene graft ethylene oxide, polystyrene graft butyl alcohol, and the like. In some aspects, chromophoric polymer particles described herein contain poly(methyl methacrylate) based comb-like polymers. Non-limiting examples of poly(methyl methacrylate) based comb-like polymers include, poly(methyl methacrylate) graft acrylic acid, poly(methyl methacrylate) graft ethylene oxide, and the like. In some aspects, chromophoric polymer particles described herein contain a comb-like polymer comprising carboxyl, amine, thiol, ester, succinimidyl ester, azide, alkyne, cyclooctyne, or phosphine groups.

In some aspects, the chromophoric polymer particles described herein contain a polymer functionalized on the terminal monomeric unit, for example with a carboxyl, amine, thiol, ester, succinimidyl ester, azide, alkyne, cyclooctyne, phosphine, or similar functional group. Examples of such polymers include but are not limited to poly(meth)acrylate polymers, polyacrylamide polymers, polyisobutylene, polydiene, polyphenylene, polyethylene, poly(ethylene glycol), polylactide, polystyrene, polysiloxane, poly(vinyl pyridine), poly(vinylpyrrolidone), polyurethane, a block copolymer thereof, a random or alternating copolymer thereof, and the like.

In some aspects, the chromophoric polymer particles described herein contain a copolymer having one or more functionalized monomeric units, for example an amphiphilic polymer, including but not limited to: poly((meth)acrylic acid)-based copolymers such as: poly(acrylic acid-b-acrylamide), poly(acrylic acid-b-methyl methacrylate), poly(acrylic acid-b-N-isopropylacrylamide), poly(n-butylacrylate-b-acrylic acid), poly(sodium acrylate-b-methyl methacrylate), poly(methacrylic acid-b-neopentyl methacrylate), poly(methyl methacrylate-b-acrylic acid), poly(methyl methacrylate-b-methacrylic acid), poly(methyl methacrylate-b-N,N-dimethyl acrylamide), poly(methyl methacrylate-b-sodium acrylate), poly(methyl methacrylate-b-sodium methacrylate), poly(neopentyl methacrylate-b-methacrylic acid), poly(t-butyl methacrylate-b-ethylene oxide), poly(2-acrylamido-2-methylpropanesulfonic acid-b-acrylic acid); polydiene-based copolymers such as: poly(butadiene(1,2 addition)-b-ethylene oxide), poly(butadiene(1,2 addition)-b-methylacrylic acid, poly(butadiene(1,4 addition)-b-acrylic acid), poly(butadiene(1,4 addition)-b-ethylene oxide, poly(butadiene(1,4 addition)-b-sodium acrylate), poly(butadiene(1,4 addition)-b-N-methyl 4-vinyl pyridinium iodide), poly(isoprene-b-ethylene oxide), poly(isoprene-b-ethylene oxide), and poly(isoprene-b-N-methyl 2-vinyl pyridinium iodide); poly(ethylene oxide)-based copolymers such as: poly(ethylene oxide-b-acrylic acid), poly(ethylene oxide-b-acrylamide), poly(ethylene oxide-b-butylene oxide), poly(ethylene oxide-b-c-caprolactone), poly(ethylene oxide-b-lactide), poly(ethylene oxide-b-lactide), poly(ethylene oxide-b-methacrylic acid), poly(ethylene oxide-b-methyl acrylate), poly(ethylene oxide-b-N-isopropylacrylamide), poly(ethylene oxide-b-methyl methacrylate), poly(ethylene oxide-b-nitrobenzyl methacrylate), poly(ethylene oxide-b-N,N-dimethylaminoethylmethacrylate), poly(ethylene oxide-b-propylene oxide), poly(ethylene oxide-b-t-butyl acrylate), poly(ethylene oxide b t butyl methacrylate), poly(ethylene oxide-b-tetrahydrofurfuryl methacrylate), poly(ethylene oxide-b-2-ethyl oxazoline), poly(ethylene oxide-b-2-hydroxyethyl methacrylate), poly(ethylene oxide-b-2-methyl oxazoline); polyisobutylene-based copolymers such as poly(isobutylene-b-acrylic acid), poly(isobutylene-b-ethylene oxide), poly(isobutylene-b-methacrylic acid); polystyrene based copolymers such as poly(styrene-b-acrylamide), poly(styrene-b-acrylic acid), poly(styrene-b-cesium acrylate), poly(styrene-b-ethylene oxide), poly(styrene-b-ethylene oxide) acid cleavable at the block junction, poly(styrene-b-methacrylic acid), poly(4-styrenesulfonic acid-b-ethylene oxide), poly(styrenesulfonic acid-b-methylbutylene), poly(styrene-b-N,N-dimethylacrylamide), poly(styrene-b-N-isopropyl acrylamide), poly(styrene-b-N-methyl 2-vinyl pyridinium iodide), poly(styrene-b-N-methyl-4-vinyl pyridinium iodide), poly(styrene-b-propylacrylic acid), poly(styrene-b-sodium acrylate) poly(styrene-b-sodium methacrylate), polyp-chloromethyl styrene-b-acrylamide), poly(styrene-co-p-chloromethyl styrene-b-acrylamide), poly(styrene-co-p-chloromethyl styrene-b-acrylic acid), poly(styrene-b-methylbutylene-co-isoprene sulfonate); polysiloxane-based copolymers such as poly(dimethylsiloxane-b-acrylic acid), poly(dimethylsiloxane-b-ethylene oxide), poly(dimethylsiloxane-b-methacrylic acid); poly(ferrocenyldimethylsilane) based copolymers such as poly(ferrocenyldimethylsilane-b-ethylene oxide); poly(2-vinyl naphthalene)-based copolymers such as poly(2-vinyl naphthalene-b-acrylic acid), poly (vinyl pyridine and N-methyl vinyl pyridinium iodide)-based copolymers such as poly(2-vinyl pyridine-b-ethylene oxide), poly (2-vinyl pyridine-b-methyl acrylic acid), poly(N-methyl 2-vinyl pyridinium iodide-b-ethylene oxide), poly(N-methyl 4-vinyl pyridinium iodide-b-methyl methacrylate), poly(4-vinyl pyridine-b-ethylene oxide) PEO end functional OH; and poly(vinyl pyrrolidone)-based copolymers such as poly (vinyl pyrrolidone-b-D/L-lactide); and the like.

In some aspects of the present disclosure, the chromophoric polymer particles provided herein include the polymer CN-PPV, also known as poly[2-methoxy-5-(2-ethylhexyloxy)-1,4-(1-cyanovinylene-1,4-phenylene)], which is a bright, compact, and orange-emitting semiconducting polymer particle. In certain aspects, CN-PPV has superior fluorescence properties, such as a large absorption cross-section, high quantum yield, and a fast emission rate. In some aspects, the chromophoric polymer particle comprises a polymer that consists essentially of CN-PPV. In some aspects, the particle includes CN-PPV and at least one other material. For example, the CN-PPV can be mixed with a copolymer or other material that provides an additional functionality.

In some aspects, the chromophoric polymer particles of the present disclosure include a semiconducting copolymer having at least two different chromophoric units. For example, a conjugated copolymer can contain both fluorene and benzothiazole chromophoric units present at a given ratio. Typical chromophoric units used to synthesize semiconducting copolymers include, but are not limited to fluorene unit, phenylene vinylene unit, phenylene unit, phenylene ethynylene unit, benzothiazole unit, thiophene unit, carbazole fluorene unit, boron-dipyrromethene unit, and derivatives thereof. The different chromophoric units can be segregated, as in a block copolymer, or intermingled. In some aspects, a chromophoric copolymer is represented by writing the identity of the major chromophoric species. For example, PFBT is a chromophoric polymer containing fluorene and benzothiazole units at a certain ratio. In some cases, a dash is used to indicate the percentage of the minor chromophoric species and then the identity of the minor chromophoric species. For example, PF-0.1 BT is a chromophoric copolymer containing 90% polyfluorene (PF) and 10% benzothiazole (BT).

In certain aspects, the chromophoric polymer particle includes a blend of semiconducting polymers. The blends can include any combination of homopolymers, copolymers, and oligomers. Polymer blends used to form chromophoric polymer particles may be selected in order to tune the properties of the resulting polymer particles, for example, to achieve a desired excitation or emission spectra for the polymer particle.

In various aspects of the present disclosure, semiconducting chromophoric polymer particles offer improved detection sensitivity in part because they exhibit higher quantum yields than other fluorescent reporters. In some aspects, the quantum yield of the chromophoric polymer particle used is more than 5%, more than 10%, more than 20%, more than 30%, more than 40%, more than 50%, more than 60%, more than 70%, more than 80%, or more than 90%. In various aspects, semiconducting chromophoric polymer particles offer improved detection sensitivity in part because they exhibit large absorption cross sections. In various aspects, semiconducting chromophoric polymer particles offer improved detection sensitivity in part because they exhibit faster emission rates than other fluorescent reporters. In certain aspects, the emission rate of the chromophoric polymer particle used is between about 100 picoseconds and about 50 nanoseconds.

In some aspects, the chromophoric polymer particle herein include polymers bearing units of small organic dye molecules, metal complexes, photochromic dye, and any combinations thereof, for example, optically inactive polymers such as polystyrene covalently linked or grafted with small organic dye, metal complexes, photochromic dyes, or any combination thereof. In some aspects, the chromophoric polymer particles comprise semiconducting polymers covalently linked with small organic dye molecules, metal complexes, photochromic dyes, or any combinations thereof as emissive units. Such emissive units can tune the emission color, increase the quantum yield, and improve the photostability of the chromophoric polymer particle. In some aspects, the small organic dyes, or metal complexes have sensing functions, and therefore add additional functionalities to the chromophoric polymer particle, such as protein sensing capability.

In some aspects, the nanoparticle transducer includes one or more chromophores (e.g., fluorophores). The chromophore emits fluorescence that depends on a fluid constituent. In some aspects, the fluid constituent is a reaction element of a reaction catalyzed by an enzyme of the nanoparticle transducer, the reaction involving an analyte. In some cases, the fluid constituent is a product of the reaction; in some cases the fluid constituent is a reactant of the reaction. In some aspects, the reaction rate varies as a function of the analyte concentration, thereby changing the concentration of the fluid constituent and causing the transducer fluorescence to vary accordingly.

In some aspects, the chromophore comprises a dye. In some aspects the dye is sensitive to one or more fluid constituents. In some aspects, the dye is sensitive to oxygen. Examples of oxygen-sensitive dyes that can be used with the nanoparticle transducers disclosed herein include Pt(II)- and Pd(II)-porphyrins, phosphorescent Ru (II) complexes, and Ir (III) complexes. Examples of the oxygen-sensitive dyes include, but not limited to Pt(II) octaethylporphine (PtOEP), Pt(II) meso-tetra(pentafluorophenyl) porphine (PtTFPP), Pt(II) octaethylporphine ketone (PtOEPK), Pd(II) octaethylporphine (PdOEP), and Pd(II) meso-tetra(pentafluorophenyl) porphine (PdTFPP). Pd(II)-meso-tetra-(4-carboxyphenyl)porphyrin (PdTPCPP), Pd(II)-meso-tetra-(4-carboxyphenyl)tetrabenzoporphyrindendrimer (PdTCPTBP), Pt(II)-coproporphyrin (PtCP), Pt(II)-meso-tetrabenzoporphyrin butyl octaester (PtTBP), Pt(II)-coproporphyrin-ketone (PtCPK), cyclometalated Ir(III) 1-chloro-bridged dimer coumarin complex (Ir(III)(Cx)2 (acac)), and [Ru(bpy)2(2-(4-carboxyphenyl)imidazo-[4,5-f] [1,10]phenanthroline)H2)]2+([Ru(bpy)2(picH2)]2+).

In some aspects, the chromophore comprises a dye that is sensitive to ions, pH, and temperature. Examples of dye to construct the nanoparticle transducer include sodium-sensitive dye, potassium-sensitive dye, calcium-sensitive dye, magnesium-sensitive dye, iron-sensitive dye, zinc-sensitive, copper-sensitive dye, manganese-sensitive dye, pH-sensitive dye, temperature-sensitive dye. Nanoparticles comprising chromophores sensitive to ions, pH, and temperature include those described in PCT/US2010/056079, for example.

In some aspects, the chromophore comprises a semiconducting chromophoric polymer that is sensitive to one or more fluid constituents. The semiconducting polymer can be designed and synthesized to have fluorescence that is sensitive to one or more fluid constituents. In some aspects, the semiconducting chromophoric polymer is sensitive to oxygen. Examples of the strategies to synthesize oxygen-sensitive semiconducting chromophoric polymers include incorporation of oxygen-sensitive unit into semiconducting polymer backbone or attachment of oxygen-sensitive unit to the side chains of the semiconducting polymer. Examples of semiconducting chromophoric polymers to which an for oxygen-sensitive unit can be attached include poly(9,9-dihexylfluorene) (PDHF)-based, poly(9,9-dioctylfluorene) (PFO)-based, poly {[9,9-di-(3-(3-methyloxetan-3-yl) methoxy) hexylfluorenyl-2,7-diyl-co-[9,9-dioctylfluorenyl-2,7-diyl]} (do-PFO)-based, poly[{9,9-dioctyl-2,7-divinylene-fluorenylene}-alt-co-{2-methoxy-5-(2-ethylhexyloxy)-1,4-phenylene}] (PFPV)-based, poly[(9,9-dioctylfluorenyl-2,7-diyl)-co-(1,4-benzo-{2,1,3}-thiadiazole)] (PFBT)-based, poly[(9,9-dioctylfluorenyl-2,7-diyl)-co-(4,7-Di-2-thienyl-2,1,3-benzothiadiazole)] (PFTBT)-based, phenylene vinylene polymers, including but not limited to, poly[2-methoxy-5-(2-ethylhexyloxy)-1,4-phenylenevinylene] (MEH-PPV)-based, poly[2-methoxy-5-(2-ethylhexyloxy)-1,4-(1-cyanovinylene-1,4-phenylene)] (CN-PPV)-based, poly(2,5-di(3',7'-dimethyloctyl)phenylene-1,4-ethynylene (PPE)-based, BODIPY based, and squaraine-based semiconducting polymer.

In some aspects, the chromophore emits fluorescence that depends on the concentration of hydrogen peroxide ($H_2O_2$). The hydrogen peroxide can be a product reaction element. In some aspects, the nanoparticle comprises a chromophoric polymer that emits fluorescence that depends on the concentration of hydrogen peroxide. In some aspects, the nanoparticle comprises a chromophoric polymer and a dye that emits fluorescence at one or more wavelengths. The amount of fluorescence of the dye can depend on the concentration of hydrogen peroxide. The dye can be physically doped or chemically attached to the chromophoric polymer for forming nanoparticles, for example. The chromophoric polymer can have energy transfer between the chromophoric polymer and the dye to enhance or amplify the fluorescence intensity of the dye. Examples of hydrogen peroxide sensitive dyes that can be used with the nanoparticle transducers disclosed herein include Coumarin derivatives, Fluorescein derivatives, Rhodamine derivatives, Cyanine derivatives, Boron-dipyrromethene (BODIPY) derivatives.

In some aspects the chromophore comprises a dye and a semiconducting chromophoric polymer, and the dye and the semiconducting polymer interact to produce enhanced fluorescence. In some aspects, the semiconducting polymer is not sensitive to the fluid constituents; fluorescence from such a polymer can provide a stable internal standard, thereby acting as a control for signals of variable fluorescence at other wavelengths. The semiconducting chromophoric polymer can have energy transfer to the dye to amplify and enhance the fluorescence of the dye. Examples of semiconducting chromophoric polymer that can be used with the nanoparticle transducers disclosed herein include poly(9,9-dihexylfluorene) (PDHF)-based, poly(9,9-dioctylfluorene) (PFO)-based, and poly {[9,9-di-(3-(3-methyl-oxetan-3-yl)methoxy) hexylfluorenyl-2,7-diyl-co-[9,9-dioctylfluorenyl-2,7-diyl]} (do-PFO)-based, poly[{9,9-dioctyl-2,7-divinylene-fluorenylene}-alt-co-{2-methoxy-5-(2-ethylhexyloxy)-1,4-phenylene}] (PFPV)-based, poly[(9,9-dioctylfluorenyl-2,7-diyl)-co-(1,4-benzo-{2,1,3}-thiadiazole)] (PFBT)-based, poly[(9,9-dioctylfluorenyl-2,7-diyl)-co-(4,7-Di-2-thienyl-2,1,3-benzothiadiazole)] (PFTBT)-based, phenylene vinylene polymers, including but not limited to, poly[2-methoxy-5-(2-ethylhexyloxy)-1,4-phenylenevinylene] (MEH-PPV)-based, poly[2-methoxy-5-(2-ethylhexyloxy)-1,4-(1-cyanovinylene-1,4-phenylene)] (CN-PPV)-based, poly(2,5-di(3',7'-dimethyloctyl)phenylene-1,4-ethynylene (PPE)-based, BODIPY based, and squaraine-based semiconducting polymer semiconducting. In some aspects the dye is sensitive to one or more fluid constituents. In some aspects, the dye is sensitive to oxygen. Examples of oxygen-sensitive dyes that can be used with the nanoparticle transducers disclosed herein include Pt(II)- and Pd(II)-porphyrins, phosphorescent Ru (II) complexes, and Ir (III) complexes. Other examples of the oxygen-sensitive dyes include, but not limited to Pt(II) octaethylporphine (PtOEP), Pt(II) meso-tetra(pentafluorophenyl) porphine (PtTFPP), Pt(II) octaethylporphine ketone (PtOEPK), Pd(II) octaethylporphine (PdOEP), and Pd(II) meso-tetra(pentafluorophenyl) porphine (PdTFPP). Pd(II)-meso-tetra-(4-carboxyphenyl)porphyrin (PdTPCPP), Pd(II)-meso-tetra-(4-carboxyphenyl)tetrabenzoporphyrindendrimer (PdTCPTBP), Pt(II)-coproporphyrin (PtCP), Pt(II)-meso-tetrabenzoporphyrin butyl octaester (PtTBP), Pt(II)-co-proporphyrin-ketone (PtCPK), cyclometalatedIr(III) 1-chloro-bridged dimer coumarin complex (Ir(III)(Cx)2 (acac)), and [Ru(bpy)2(2-(4-carboxyphenyl)imidazo-[4,5-f] [1,10]phenanthroline)H2)]2+([Ru(bpy)2(picH2)]2+). The dye can be physically blended or chemically attached to the semiconducting chromophoric polymer to form the nanoparticle transducer.

In some aspects the chromophore comprises a plurality of dyes. A first dye is sensitive to one or more fluid constituents, and a second dye can interact with the sensitive dye to produce enhanced fluorescence. In some aspects, at least one dye is not sensitive to the fluid constituents, thus provide a stable fluorescence as an internal standard. The plurality of dyes can emit fluorescence at different wavelengths, allowing independent measurement of each dye's fluorescence. The sensitive and non-sensitive dyes can interact with each other to amplify and enhance the fluorescence of the dye that is sensitive to the one or more fluid constituents.

In some aspects, the chromophoric polymer particle comprises a semiconducting polymer physically mixed or chemically cross-linked with other chromophoric polymers, such as inactive polymers covalently linked or grafted with small organic dye, metal complexes, photochromic dyes, or any combination thereof, to have additional functionalities such as protein sensing.

In some aspects, the chromophoric polymer particle includes semiconducting polymers physically mixed or chemically cross-linked with other components such as fluorescent dyes, inorganic luminescent materials, magnetic materials, metal materials, and the like in order to tune emission color, improve quantum yield and/or photostability, and/or provide additional functionalities such as magnetic functions, plasmon resonance functions, and the like.

The optical properties, such as absorption wavelength, for a given chromophoric polymer particle can be tuned by modifying its composition and/or structure. Semiconducting polymers have been developed with absorption wavelengths ranging from UV to infrared, including the entire visible spectrum. In some aspects, chromophoric polymer particles having a peak absorption wavelength between about 200 nanometers and about 300 nanometers, about 250 nanometers and about 350 nanometers, about 300 nanometers and about 400 nanometers, about 350 nanometers and about 450 nanometers, between about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, or about 900 nanometers and about 1000 nanometers, are used.

Semiconducting polymers have been developed with emission wavelengths ranging from UV to infrared, including the entire visible spectrum. In some aspects, chromophoric polymer particles having a peak emission wavelength between about 200 nanometers and about 300 nanometers, about 250 nanometers and about 350 nanometers, about 300 nanometers and about 400 nanometers, about 350 nanometers and about 450 nanometers, about 400 nanometers and about 500 nanometers, about 450 nanometers and about 550 nanometers, about 500 nanometers and about 600 nanometers, about 550 nanometers and about 650 nanometers, about 600 nanometers and about 700 nanometers, about 650 nanometers and about 750 nanometers, about 700 nanometers and about 800 nanometers, about 750 nanometers and about 850 nanometers, about 800 nanometers and about 900 nanometers, about 850 nanometers and about 950 nanometers, about 900 nanometers and about 1000 nanometers, about 950 nanometers and about 1050 nanometers, about 1000 nanometers and about 1100 nanometers, about 1150 nanometers and about 1250 nanometers, or about 1200 nanometers and about 1300 nanometers, are used.

In some aspects, the present disclosure provides chromophoric polymer particles with narrow-band emissions. Narrow-band emissions are advantageous for certain applications, including but not limited to resolution of multiple fluorescence signals. The emission wavelength of the polymer particles can vary from ultraviolet to near infrared region. In some aspects, the FWHM of the emission band is less than about 100 nanometers, about 70 nanometers, about 65 nanometers, about 60 nanometers, about 55 nanometers, about 50 nanometers, about 45 nanometers, about 40 nanometers, about 35 nanometers, about 30 nanometers, about 25 nanometers, about 20 nanometers, or about 10 nanometers. In some aspects, the FWHM of the polymer particles described herein can range between about 5 nanometers to about 100 nanometers, from about 10 nanometers to about 70 nanometers, from about 20 nanometers to about 60 nanometers, or from about 30 nanometers to about 50 nanometers.

In some aspects, the variety of chromophoric polymer particles of the present disclosure include polymers that have a narrow band emissive unit (e.g., a narrow band monomer and/or a narrow band unit). For example, the present disclosure can include a homopolymer or heteropolymer including a narrow band monomer, such as BODIPY and/or BODIPY derivative monomer, a squaraine and/or squaraine derivative monomer, a metal complex and/or metal complex derivative monomer, a porphyrin and/or porphyrin derivative monomer, a metalloporphyrin and/or metalloporphyrin derivative monomer, a phthalocyanine and/or phthalocynanine derivative monomer, a lanthanide complex and/or lanthanide complex derivative monomer, a perylene and/or perylene derivative monomer, a cyanine and/or cyanine derivative monomer, a rhodamine and/or rhodamine derivative monomer, a coumarin and/or coumarin derivative monomer, and/or a xanthene and/or xanthene derivative monomer. In certain aspects, a narrow band unit is, e.g., a narrow band monomer or a fluorescent nanoparticle embedded in or attached to the polymer particle. The fluorescent nanoparticle can be, e.g., a quantum dot. Optionally, a narrow band unit includes a polymer or fluorescent dye molecule that gives a narrow emission in a polymer particle of the present disclosure.

In some aspects of the present disclosure, the apparatus, compositions, systems, and methods provided herein utilize one or more chromophores (e.g., dyes or semiconducting chromophoric polymers) that are capable of generating fluorescent light at one or more wavelengths, for example, in response to incident radiation such as UV, visible, far red, near infrared, or other light. In some cases, amount of fluorescence from the chromophore at a given wavelength varies as a function of the local concentration of a fluid constituent (a signal chromophore); in other aspects, amount of fluorescence from the chromophore does not vary in response to said local concentration (a control chromophore). In certain aspects, nanoparticles as provided herein can incorporate both a signal and a control chromophore, emitting fluorescence at a signal wavelength and a control wavelength, respectively. Although various aspects herein are described in the context of nanoparticles having one or two different emission wavelengths, it shall be understood that the approaches presented herein are also applicable to nanoparticles that emit more than two wavelengths. For example, nanoparticles can be provided that emit at two signal wavelengths and one or two control wavelengths, which can be used for multiple analyte measurement signals. A plurality of different nanoparticles with different signal/control wavelength pairs, each responsive to a distinct analyte (or optionally to the same analyte, e.g., for redundant signaling), may be provided.

In certain aspects, the chromophores generating fluorescence at the signal wavelength exhibit different optical characteristics (e.g., emission spectrum, absorbance spectrum, peak emission wavelength(s), peak excitation wavelength(s), emission intensities, emission lifetimes, emission rates) when in different concentrations of a fluid constituent. For instance, chromophore may exhibit increased (or decreased) fluorescence in response to increased concentration of a fluid constituent such as a molecule. In some aspects, the variation of the fluorescence can be ratiometric as a function of the concentration of a fluid constituent. The molecule can be oxygen, for example, which can be a reactant or a product of a reaction involving an analyte to be measured and catalyzed by an enzyme. The enzyme can be coupled to a nanoparticle comprising the chromophore, such that reactions catalyzed by the enzyme change the local concentration of the molecule, thereby changing the fluorescence of the chromophore in response to changes in concentration of the analyte. In some aspects, such changes can be ratiometric. Fluorescence can be generated at a control wavelength, such that a fluorescence ratio of control to signal can serve as a signal of analyte concentration, eliminating or reducing certain sources of noise and uncertainty in fluorescence intensity measurements, for example.

Enzyme Compositions

In certain aspects disclosed herein, small molecule detection is provided is based on the integration of a nanoparticle oxygen transducer with an oxygen-consuming enzyme that catalyzes the small molecule oxidation reactions. In some cases, the nanoparticle transducer can be directly mixed with the enzyme for measurements. In some cases, covalent conjugation is provided to link the nanoparticle to the enzyme, yielding a compact probe that can be used for intracellular sensing. Upon formation of the enzyme corona on the nanoparticle surface, the nanoparticle-enzyme bioconjugate behaves as a nanoreactor that depletes its internal oxygen reservoir in the presence of the small molecule analyte to which the enzyme is sensitive. Small molecule concentrations are thus monitored by the optical signal of the oxygen transducer as oxygen is depleted. The performance of this sensing scheme is dependent factors including: (1) whether the presence of the analyte can induce distinct changes in oxygen distribution profile; (2) whether the oxygen transducer is able to transform the oxygen change to optical signal. In addition, the in vivo detection is also closely related with the issues such as local microvascular perfusion, availability of tissue oxygen, and enzyme activity. In the following section, glucose is provided as an example by which the effectiveness of the nanoparticle transducers described herein in sensing analyte concentrations may be illustrated with both theoretical analysis and experimental evidence, for both in vitro and in vivo applications. Based on the examples described herein, nanoparticle transducers may be fabricated to produce fluorescent signals for detection of a wide variety of analytes, including small molecules, large molecules, and other fluid constituents, through the selection of an appropriately-reactive enzyme and corresponding chromophores sensitive to a reaction element of the reaction catalyzed thereby.

In many aspects, the nanoparticle transducers provided herein comprise an enzyme, and the enzyme catalyzes a reaction. The reaction involves the analyte to be measured, and produces products and consumes reactants, collectively referred to as reaction elements. In many aspects, the reaction elements include a fluid constituent, and a concentration of the fluid constituent is changed by the reaction. For example, the fluid constituent can be a reaction product and the reaction can increase the concentration of the fluid constituent. Alternatively, the fluid constituent can be a reactant and reaction can decrease its concentration. In some aspects, the fluid constituent is oxygen, and the oxygen is a reactant. In some aspects, the oxygen-consuming enzyme and analyte, respectively, comprise one or more of the following pairs: glucose oxidase and glucose; ascorbate oxidase and ascorbic acid; glutamate oxidase and glutamate; dopamine beta-hydroxylase and dopamine; cholesterol oxidase and cholesterol; and alcohol oxidase and alcohol, lactate oxidase and lactate, and xanthine oxidase and xanthine, monoamine oxidase and monoamine, NADPH oxidase and NADPH, L-gulonolactone oxidase and L-gulonolactone, lysyl oxidase and lysine, laccases and their various substrates such as phenols, and cytochrome P450 oxidase and its various substrates including drugs. In some cases, the oxygen-consuming enzyme is amine oxidase and the analyte is an amino acid. In some cases, the oxygen-consuming enzyme is a cytochrome P450 and the analyte is a drug that reacts with oxygen when catalyzed by the cytochrome P450. In some cases, the oxygen-consuming enzyme is the NADPH oxidase (nicotinamide adenine dinucleotide phosphate-oxidase) and the analyte is NADPH. In some cases, the oxygen-consuming enzyme is Xanthine oxidase and the analyte is Xanthine. In some cases, the oxygen-consuming enzyme is gulonolactone oxidase and the analyte is gulonolactone.

In some aspects, the fluid constituent is other than oxygen; for example, the fluid constituent can be an ion, the enzyme can catalyze a reaction that changes ionic concentration, and the chromophore can produce fluorescence modulated by said ionic concentration; the fluid constituent can be an acid or base, the enzyme can catalyze a reaction that changes pH, and the chromophore can produce fluorescence modulated by said pH; or the fluid constituent can be heat energy, the enzyme can catalyze a reaction that changes temperature, and the chromophore can produce fluorescence modulated by said temperature. In some aspects, the fluid constituent can be hydrogen peroxide, the enzyme can catalyze a reaction that changes hydrogen peroxide concentration, and the chromophore can produce fluorescence modulated by said hydrogen peroxide concentration. For example, hydrogen peroxide can be a product of the reaction.

In some aspects, a plurality of enzymes are coupled to the nanoparticle transducer to catalyze a respective plurality of reactions. The plurality of reactions form a reaction chain, where one or more products of one reaction are reactants of another reaction. For example, an enzyme cascade may be provided by the plurality of enzymes, with each enzyme performing a step of the cascade. At least one of the plurality of reactions involves the analyte as a reactant, and at least one of the reactions has the fluid constituent as a reaction element for modulation of the chromophore emission intensity.

Device Components

In some aspects, the systems described herein include a computer comprising one or more processors and a memory device with executable instructions stored thereon. In some aspects, the computer is used to perform the methods described herein. In various aspects, a computer can be used to implement any of the systems or methods illustrated and described above. In some aspects, a computer includes a processor that communicates with a number of peripheral subsystems via a bus subsystem. These peripheral subsystems can include a storage subsystem, comprising a memory subsystem and a file storage subsystem, user interface input devices, user interface output devices, and a network interface subsystem.

In some aspects, a bus subsystem provides a mechanism for enabling the various components and subsystems of the computer to communicate with each other as intended. The bus subsystem can include a single bus or multiple busses.

In some aspects, a network interface subsystem provides an interface to other computers and networks. The network interface subsystem can serve as an interface for receiving data from and transmitting data to other systems from a computer. For example, a network interface subsystem can enable a computer to connect to the Internet and facilitate communications using the Internet.

In some aspects, the computer includes user interface input devices such as a keyboard, pointing devices such as a mouse, trackball, touchpad, or graphics tablet, a scanner, a barcode scanner, a touch screen incorporated into the display, audio input devices such as voice recognition systems, microphones, and other types of input devices. In general, use of the term "input device" is intended to include all possible types of devices and mechanisms for inputting information to a computer.

In some aspects, the computer includes user interface output devices such as a display subsystem, a printer, a fax machine, or non-visual displays such as audio output devices, etc. The display subsystem can be a flat-panel device such as a liquid crystal display (LCD) or a projection device for example. In general, use of the term "output device" is intended to include all possible types of devices and mechanisms for outputting information from a computer.

In some aspects, the computer includes a storage subsystem that provides a computer-readable storage medium for storing the basic programming and data constructs. In some aspects, the storage subsystem stores software (programs, code modules, instructions) that when executed by a processor provides the functionality of the methods and systems described herein. These software modules or instructions can be executed by one or more processors. A storage subsystem can also provide a repository for storing data used in accordance with the present disclosure. The storage subsystem can include a memory subsystem and a file/disk storage subsystem.

In some aspects, the computer includes a memory subsystem that can include a number of memories including a main random access memory (RAM) for storage of instructions and data during program execution and a read only memory (ROM) in which fixed instructions are stored. A file storage subsystem provides a non-transitory persistent (non-volatile) storage for program and data files, and can include a hard disk drive, a USB stick, a solid state drive, an optical drive, removable media cartridges, and other like storage media.

The computer can be of various types including a smart phone, tablet computer, personal computer, a portable computer, a workstation, a network computer, a mainframe, a kiosk, a server or any other data processing system. Due to the ever-changing nature of computers and networks, the description of computer contained herein is intended only as a specific example for purposes of illustrating the aspect of the computer. Many other configurations having more or fewer components than the system described herein are possible.

Further Aspects of the Invention

In various aspects, a nanoparticle transducer for analyte concentration measurements is provided. The nanoparticle transducer comprises a nanoparticle comprising a chromophore, and an enzyme is coupled to the nanoparticle. The enzyme catalyzes a reaction comprising a plurality of reaction elements. The reaction elements comprise one or more reactants including the analyte and one or more products. The chromophore emits fluorescence in an amount determined by a concentration of a reaction element of the plurality of reaction elements. The emission of fluorescence can be induced by appropriate light illumination, such as ultraviolet, visible, far red, near infrared, or other light.

In some aspects, one of the reaction elements is oxygen, and the amount of fluorescence emitted from the chromophore is determined by a concentration of the oxygen. In some cases, the enzyme comprises glucose oxidase. The one or more reactants can comprise glucose and oxygen and the one or more products comprise hydrogen peroxide and D-glucono-1,5-lactone.

In some aspects, the nanoparticle transducer further comprises catalase.

In some aspects, the amount of fluorescence emitted from the chromophore is determined by a concentration of a reactant; in some aspects, the amount of fluorescence emitted from the chromophore is determined by a concentration of a product.

In some aspects, the nanoparticle comprises a Pdot. The enzyme can be covalently bonded to the nanoparticle.

In some aspects, the chromophore comprises a semiconducting polymer. In some aspects, chromophore comprises a dye. The dye can be contained within the nanoparticle. The chromophore can comprise a semiconducting polymer and a dye, and the dye and the semiconducting polymer interact to produce enhanced fluorescence. In some cases, the chromophore comprises a blend of two or more semiconducting polymers.

In some aspects, the fluorescence emitted from the chromophore comprises a signal fluorescence wavelength and a control fluorescence wavelength. The fluorescence emitted from the chromophore can comprise a fluorescence ratio equal to the ratio of the amount of fluorescence emitted at the signal wavelength to the amount of fluorescence emitted at the control fluorescence wavelength. The signal fluorescence ratio can be determined by the concentration of the reaction element of the plurality of reaction elements. In many cases, the fluorescence ratio varies ratiometrically with the concentration of the analyte. In some cases, the signal-wavelength fluorescence grows substantially linearly with analyte concentration while the control-wavelength fluorescence remains substantially constant.

In various aspects, the analyte is glucose and the range of analyte concentrations is within the range of between 0 and about 20 mM of glucose. In some cases, the range of analyte concentrations is within the range of about 3 mM glucose to about 15 mM glucose.

In some aspects, nanoparticle contains at least 20 percent chromophore by weight. For example, the nanoparticle can contain at least 50 percent chromophore by weight, or at least 90 percent chromophore by weight. In some cases, the nanoparticle comprises about 100 percent chromophore by weight.

In some aspects, the nanoparticle comprises a second chromophore for fluorescent detection of a second analyte and a second enzyme coupled to the nanoparticle. The second enzyme catalyzes a second reaction comprising a second plurality of reaction elements. The second plurality of reaction elements comprises a second one or more reactants including the second analyte and a second one or more products. An amount of fluorescence emitted from the second chromophore is determined by a concentration of a second reaction element of the second plurality of reaction elements. The fluorescence of the second chromophore comprises a wavelength different from the fluorescence of the other chromophore.

In some aspects, the nanoparticle transducer comprises a second nanoparticle comprising a second chromophore and a second enzyme coupled to the nanoparticle and configured to catalyze a second reaction comprising a second plurality of reaction elements. The second plurality of reaction elements comprises a second one or more reactants including the second analyte and a second one or more products. An amount of fluorescence emitted from the second chromophore is determined by a concentration of a second reaction element of the second plurality of reaction elements.

In some cases, the enzyme is selected from the group consisting of ascorbate oxidase, glutamate oxidase, dopamine beta-hydroxylase, cholesterol oxidase, alcohol oxidase, amine oxidase, and cytochrome P450. In some cases, the analyte is selected from the group consisting of ascorbic acid, glutamate, dopamine, cholesterol, alcohol. In some cases, the analyte can be an amino acid, a drug, a protein, a nucleic acid molecule, or a transmitter molecule. In some cases, the analyte can be a carbohydrate, a lipid, or a metabolite. In some cases the analyte is a sugar.

In some aspects, the analyte concentration is a blood concentration. In some aspects, the analyte concentration is a concentration in lymph, saliva, tears, interstitial fluid, spinal fluid, or urine.

In some aspects, the nanoparticle transducer comprises a plurality of enzymes, and the plurality of enzymes catalyze a respective plurality of reactions each comprising a respective plurality of reaction elements. The analyte is a reactant of one of the plurality of reactions, and the fluorescence emitted from the chromophore is determined by a concentration of a reaction element of at least one of the reactions. In some cases, one or more of the products of one enzyme's reaction are reactants of another enzyme's reaction, thereby forming an enzyme reaction chain. Analyte concentrations can thus affect the fluorescence of the chromophore through participation in the enzyme reaction chain.

In some cases, the critical dimension of the nanoparticle transducer is less than about 1000 nm, less than 700 nm, less than about 500 nm, or less than about 100 nm. In some cases, the critical dimension of the nanoparticle transducer in the range of about 15 nm to about 45 nm.

In various aspects, an apparatus for measuring the concentration of an analyte in a biological fluid is provided. The apparatus comprises a plurality of fluorescent nanoparticle transducers as provided according to the aspects disclosed herein. The apparatus further comprises an optical sensor coupled to a processor and memory and an illumination source configured to illuminate the plurality of fluorescent nanoparticles with light so as to induce fluorescence therefrom. The memory comprises instructions that, when executed, cause the processor to use the optical sensor to measure fluorescence emitted by the plurality of fluorescent nanoparticle transducers.

In some aspects, the biological fluid is blood, lymph, saliva, tears, interstitial fluid, spinal fluid, or urine.

In some aspects, the plurality of fluorescent nanoparticle transducers are adapted to be located under the skin of a patient, and the optical sensor is adapted to detect fluorescence transmitted through the skin by the plurality of fluorescent nanoparticle transducers when facing the skin. In some cases, the optical sensor is configured to detect an amount of signal fluorescence at the signal fluorescence wavelength and an amount of control fluorescence at the control fluorescence wavelength, and the memory comprises instructions to cause the processor to determine a measured fluorescence ratio based on said measured amounts of signal and control fluorescence. In some cases, the memory comprises instructions to cause the processor to determine the concentration of the analyte based on the measured fluorescence ratio.

In various aspects, a contact lens for the detection of glucose concentrations is provided. The contact lens comprises a permeable, transparent membrane wearable over the eye, and the lens contains a plurality of nanoparticle transducers according to the aspects disclosed herein. The nanoparticle transducers are configured to produce fluorescence in response to illumination by a scanner, and the amount of fluorescence provides a signal detectable by the scanner for determination of concentration of glucose in fluids on the surface of the eye. The membrane of the lens can be shaped to correct the vision of a person when worn.

In various aspects, a device for measuring glucose concentrations from the sweat of a subject is provided. The device comprises a plurality of fluorescent nanoparticle transducers according to the aspects disclosed herein, and positioned by the device to contact the skin of the subject when worn. The device further comprises an illumination source configured to illuminate the plurality of fluorescent nanoparticles with light so as to induce fluorescence therefrom and an optical sensor disposed in the device, and oriented to detect fluorescence from the plurality of fluorescent nanoparticle transducers. A processor is coupled to the optical sensor. The processor is configured to determine, based on fluorescence detected by the optical sensor, a concentration of glucose in the sweat. The processor can further be configured to determine a concentration of glucose in the blood based on the concentration of glucose in the sweat.

In various aspects, a method of determining analyte concentration in a fluid is provided. The fluid is contacted with a nanoparticle transducer according to the aspects disclosed herein. The fluorescence of the nanoparticle transducer is measured, and the concentration of the analyte in the fluid is determined based on the measured fluorescence. In some cases, the method comprises illuminating the nanoparticle transducers with light, thereby inducing fluorescence.

In some aspects, the determining comprises comparing the measured fluorescence to a calibration curve for the nanoparticle transducer to determine the analyte concentration in the fluid. In some aspects, the measuring comprises measuring a plurality of fluorescence wavelengths and the determining is based on a ratio of the measured wavelengths. In some cases, the fluid is blood, sweat, or tears.

In some aspects, a method of measuring a concentration of an analyte in a fluid is provided. The analyte causes a reaction in the fluid, and the reaction changes the concentration of a fluid component. The fluid is contacted with a Pdot that comprises a chromophore, and the chromophore emits fluorescence in an amount determined by a concentration of the fluid component. The fluorescence is emitted by the chromophore, and a concentration of the analyte in the fluid is determined based on the fluorescence.

In some aspects, the fluorescence emitted from the chromophore comprises a fluorescence ratio equal to the ratio of an amount of fluorescence emitted at a signal fluorescence wavelength to an amount of fluorescence emitted at a control fluorescence wavelength, and the fluorescence ratio is determined by the concentration of the fluid component. In some cases, the determining of the concentration comprises measuring fluorescence at the signal and control fluorescence wavelengths, determining a measured fluorescence ratio based on said measuring, and determining a concentration of the analyte based on the measured fluorescence ratio.

In some aspects, the analyte is ascorbic acid and the fluid component is oxygen. In some cases, the determined concentration is between 1 mM and 20 mM of ascorbic acid. In some aspects, the fluid is blood, sweat, or tears.

The specific dimensions of any of the apparatuses, devices, systems, and components thereof, of the present disclosure can be readily varied depending upon the intended application, as will be apparent to those of skill in the art in view of the disclosure herein. Moreover, it is understood that the examples and aspects described herein are for illustrative purposes only and that various modifications or changes in light thereof may be suggested to persons skilled in the art and are included within the spirit and purview of this application and scope of the appended claims. Numerous different combinations of aspects described herein are possible, and such combinations are considered part of the present disclosure.

As used herein A and/or B encompasses one or more of A or B, and combinations thereof such as A and B. As used herein, where the disclosure describes aspects as comprising one or more elements, also disclosed are aspects consisting of said elements.

All features discussed in connection with any aspect or aspect herein can be readily adapted for use in other aspects and aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

Unless otherwise specified, the presently described methods and processes can be performed in any order. For example, a method describing steps (a), (b), and (c) can be performed with step (a) first, followed by step (b), and then step (c). Or, the method can be performed in a different order such as, for example, with step (b) first followed by step (c) and then step (a). Furthermore, those steps can be performed simultaneously or separately unless otherwise specified with particularity.

The particulars shown herein are by way of example and for purposes of illustrative discussion of the preferred aspects of the present disclosure only and are presented in the cause of providing what is believed to be the most useful and readily understood description of the principles and conceptual aspects of various aspects of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

While preferred aspects of the present disclosure have been shown and described herein, it is to be understood that the disclosure is not limited to the particular aspects of the disclosure described, as variations of the particular aspects can be made and still fall within the scope of the appended claims. It is also to be understood that the terminology employed is for the purpose of describing particular aspects of the disclosure, and is not intended to be limiting. Instead, the scope of the present disclosure is established by the appended claims.

Where a range of values is provided, it is understood that each intervening value, to the tenth of the unit of the lower limit unless the context clearly dictates otherwise, between the upper and lower limit of that range, and any other stated or intervening value in that stated range, is encompassed within the disclosure provided herein. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure provided herein.

All features discussed in connection with an aspect or aspect herein can be readily adapted for use in other aspects and aspects herein. The use of different terms or reference numerals for similar features in different aspects does not necessarily imply differences other than those expressly set forth. Accordingly, the present disclosure is intended to be described solely by reference to the appended claims, and not limited to the aspects disclosed herein.

EXAMPLES

The following examples are included to further describe some aspects of the present disclosure, and should not be used to limit the scope of the invention.

Example 1

Operating Principles of Nanoparticle Transducers for Analyte Concentration Measurements In one example, the spatial and temporal changes of oxygen concentration in typical sample configurations are simulated by a model that takes into account the glucose enzymatic reactions of glucose oxidase and oxygen diffusion. FIG. 1A through FIG. 1H illustrate simulated $O_2$ depletion kinetics and distribution profiles for an exemplary nanoparticle transducer for detection of glucose using an $O_2$-modulated signal from reactions catalyzed with glucose oxidase. A typical cuvette (1 cm×1 cm×3 cm) containing glucose oxidase (GOx) is used to model the oxygen consumption induced by glucose. Briefly, in a closed system (without oxygen diffusion), the oxygen consumption kinetics in the presence of GOx and glucose can be expressed as $$a([O_2]-[O_2]_0)+b(\ln[O_2]-\ln[O_2]_0=-(t-t_0))$$

Where $[O_2]_0$ corresponds to $[O_2]$ in air-saturated solution at $t_0$ time just before the reactions start. Parameters a and b can be calculated from the GOx concentration, enzymatic reaction rate constants for a given glucose concentration. This expression will be valid when glucose is present in excess over oxygen, which is generally true because the physiological glucose concentration (typically in ~mM range) is much higher than the oxygen concentrations in air-saturated solution (~250 µM) and tissues (<100 µM). Based on the above equation, the kinetic change of oxygen concentration in a closed cuvette containing GOx (5 nM) and glucose at variable concentrations are shown in FIG. 1A. As can be seen, the initial oxygen concentration (~250 µM, air-saturated solution) is decreased as enzyme reaction occurs, and the discrepancies induced by different glucose concentrations were distinguished thereafter. The oxygen was finally depleted to similar equilibrium levels due to limited availability of oxygen in the solution (closed system without oxygen supply and diffusion) for the solutions with different the glucose contents.

Oxygen diffusion is relevant to glucose determination in an open cuvette configuration and subcutaneous tissues. To simplify the simulation, the Z-axis of the cuvette was discretized into a series of thin layers, modeling oxygen as only diffusing from the top opening. The temporal oxygen concentration in each layer was simulated by the combined effect of oxygen consumption and diffusion governed by Fick's law. Equilibria were finally established between oxygen consumption and diffusion, yielding flat concentration curves after a substantial reaction time, as shown in FIG. 1B. FIG. 1C illustrates a 3-D plot of temporal and spatial oxygen distribution for a system with 5 nM GOx and 20 mM glucose along the Z-axis of an open cuvette configuration, as well as the temporal evolution in each layer dependent on the enzymatic reaction time. At the time point of 500 seconds, the glucose concentrations were well distinguished by the oxygen mappings, particularly in the bottom portion of the cuvettes. FIG. 1D illustrates oxygen distribution profiles in an open cuvette with different glucose concentrations at a time point of 500 seconds. This result indicates glucose concentration in a biological fluid, by the aid of oxygen transducer, can be effectively and efficiently measured with open cuvette configuration in a fluorometer.

Further simulation is provided of the oxygen mapping for a spherical sample in subcutaneous tissue, where the tissue oxygen concentration (<100 µM) is much less than that in the air-saturated solution (~250 To meet the requirement for in vivo real-time glucose monitoring, GOx concentrations of 50 nM were provided to achieve rapid response time. As expected, the temporal oxygen changes at the center of the sample yielded short response times as compared to those in low GOx concentration. FIG. 1E illustrates these $O_2$ depletion kinetics in a closed tissue oxygen environment. Oxygen was allowed to diffuse from the circular edge to the interior, resembling a thin layer of 3D spherical object in actual implantation. FIG. 1F illustrates $O_2$ depletion kinetics in tissue with oxygen diffusion, showing temporal evolution in the presence of oxygen diffusion indicated the glucose enzymatic reactions, leading to distinct oxygen distribution curves in a relatively short time. FIG. 1G illustrates 2-D mapping of a circular configuration with oxygen diffusion at the time point of 20 seconds. As further indicated by the 2D mapping, the oxygen profiles were clearly distinguished for different glucose levels, indicating subcutaneous glucose measurement by oxygen transducer is highly feasible. It is worth noting that oxygen diffusion to some extent yielded much high sensitivity in glucose determination as compared the cases without oxygen diffusion. This difference is shown in FIG. 1H, which illustrates sensitivity of oxygen depletion for glucose determination with and without oxygen diffusion at the time point of 20 seconds. To adjust the oxygen or glucose diffusion in practical experiments, a number of strategies can be employed, such as embodiment of the transducer in porous gels or other matrix with different encapsulation layers.

Example 2

Production of Nanoparticle Transducers for Analyte Concentration Measurements

In this example, nanoparticle transducers were produced and characterized in an exemplary system for detection of glucose. Aqueous dispersion of semiconductor polymer dots was performed using a reprecipitation method. In a typical preparation, the semiconducting polymer PDHF, functional polymer PSMA and phosphorescent dye PtOEP were dissolved in anhydrous tetrahydrofuran (THF) by stirring overnight under inert atmosphere to make a 1 mg/mL stock solution, respectively. The three solutions were diluted and mixed in THF to produce a solution mixture with a PDHF concentration of 100 µg/mL, a PtOEP concentration of 10 µg/mL and a PSMA concentration of 10 µg/mL. A 2 mL quantity of the solution mixture was added quickly to 10 mL of Milli-Q water in a bath sonicator while sonicating the mixture followed by an additional 100 seconds of sonication. The THF was removed by nitrogen stripping, and the solution concentrated to 5 mL on a 90° C. hotplate followed by filtration through a 0.2 micron filter. During nanoparticle formation, the maleic anhydride units of PSMA molecules were hydrolyzed in the aqueous environment, generating carboxyl groups on Pdots. The phosphorescent dye molecules were encapsulated inside Pdots because of their hydrophobic nature. The Pdot dispersions were clear and stable for months without signs of aggregation.

The fluctuations of oxygen concentration induced by glucose can be transformed into an optical signal by using an oxygen responsive transducer. FIG. 2A through FIG. 2D illustrate preparation and characterization of a nanoparticle transducer comprising a Pdot-GOx assembly. The Pdot transducer comprises a fluorescent semiconductor polymer [poly(9,9-dihexylfluorenyl-2,7-diyl), PDHF] doped with a chromophore comprising an oxygen-sensitive phosphorescent dye (platinum (II) octaethylporphine, PtOEP). In this design, the conjugated polymer PDHF served as the light-harvester that transferred energy to the PtOEP dye, resulting in bright phosphorescence highly sensitive to the oxygen concentration.

Figure 2A:
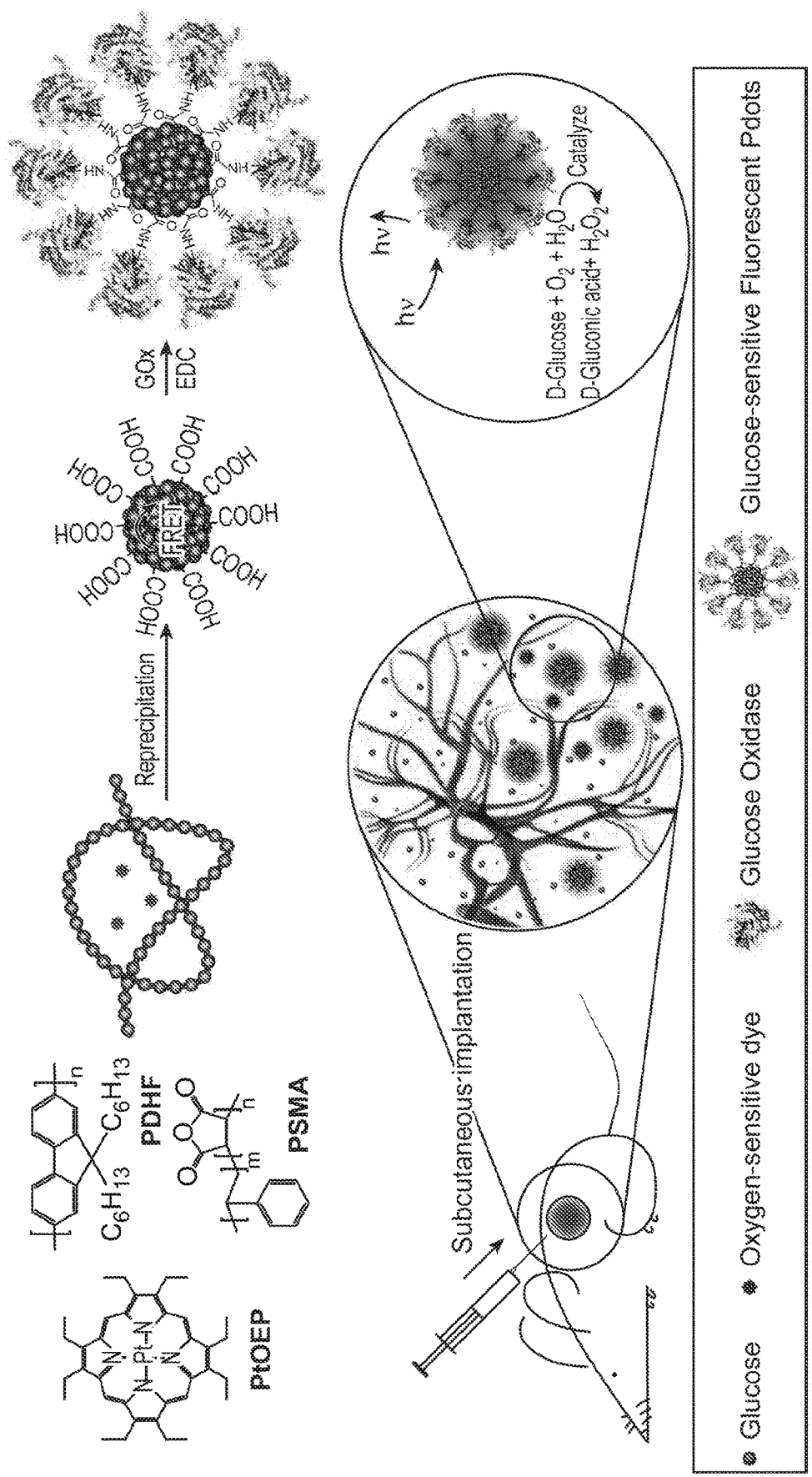
FIG. 2A through FIG. 2D illustrate preparation and characterization of a nanoparticle transducer comprising a Pdot-GOx assembly.

FIG. 2A is a schematic illustration of the formation of Pdot-GOx bioconjugates for in vivo glucose monitoring. As shown in FIG. 2A, oxygen-sensitive Pdots were functionalized with surface carboxyl groups. They were coated with GOx using the EDC-catalyzed reaction between the carboxyl groups of Pdots and the amine groups in the enzyme. Bioconjugation was performed by utilizing the EDC-catalyzed reaction between carboxyl groups on Pdots surface and amine groups on the GOx enzyme. In this bioconjugation reaction, 80 µL of concentrated HEPES buffer (1 M, pH 6.5) were added to 4 mL of functionalized Pdots solution (50 µg/mL in MilliQ water), resulting in a Pdot solution in 20 mM HEPES buffer with a pH of 6.5. Then, 100 µL of glucose oxidase (10 µM in 20 mM pH=6.5 HEPES) was added to the solution and mixed well on a vortex. 80 µL of freshly-prepared EDC solution (5 mg/mL in MilliQ water) was added to the solution, and the above mixture was left on a rotary shaker for 4 hours at room temperature. Finally, the resulting Pdot bioconjugates were separated from free biomolecules by gel filtration using Sephacryl HR-300 gel media. The ratio of GOx to Pdots can be varied to produce Pdot-GOx sensors of different dynamic range.

Figure 2B:
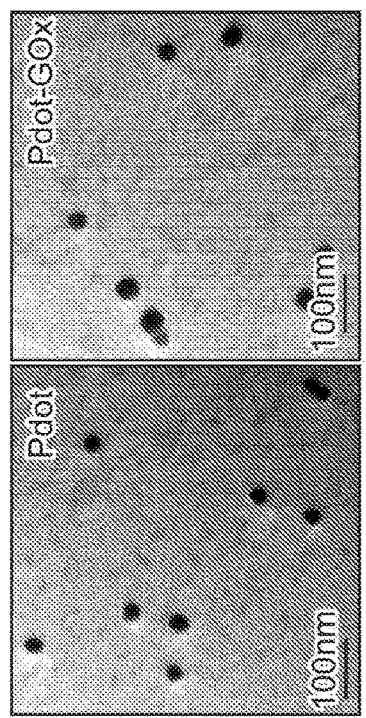
Figure 2C:
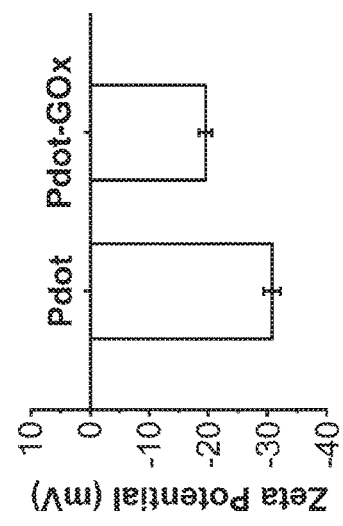
Figure 2D:
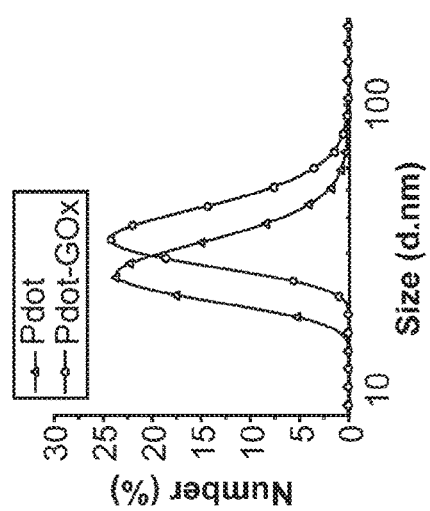

Dynamic light scattering measurements indicated the hydrodynamic diameter of the Pdots increased from 24 nm to 32 nm after bioconjugation, as illustrated in FIG. 2B, while the surface zeta potential of Pdot-GOx changed from −31 mV to −20 mV, as shown in FIG. 2C. Both the particle size and surface potential measurements confirmed the successful conjugation and presence of GOx on the particle surface. Transmission electron microscopy (TEM) showed that the Pdot-GOx nanoparticles were spherical and monodispersed. FIG. 2D illustrates representative TEM images of carboxyl Pdots (left) and Pdot-GOx (right).

Figure 3B:
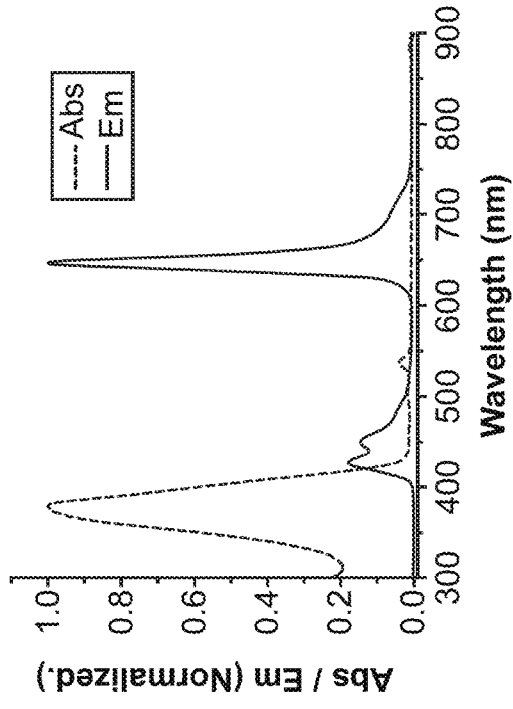
FIG. 3A through FIG. 3D illustrate further properties of nanoparticle transducers such as Pdot transducers.
Figure 3D:
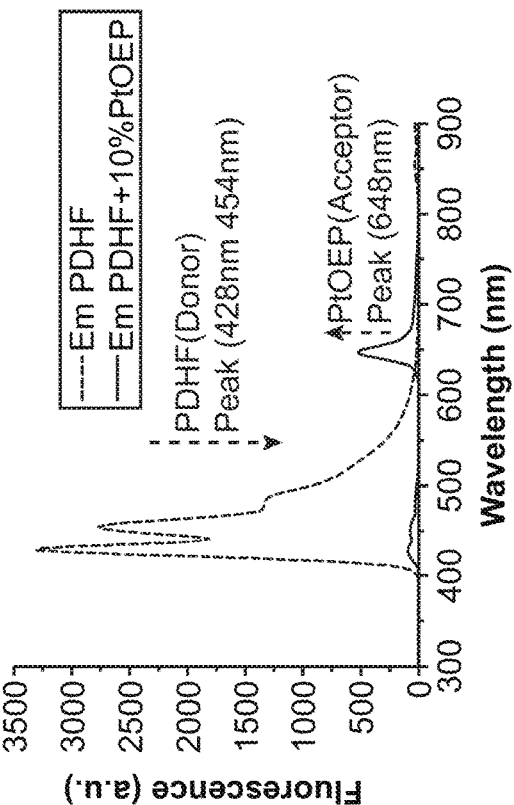
Figure 3A:
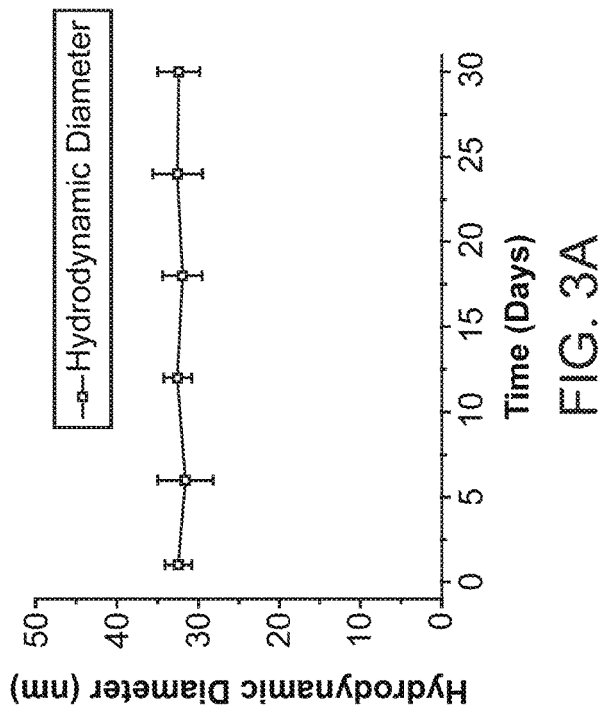

The Pdot-GOx bioconjugates also exhibited great colloidal stability in phosphate-buffered saline (PBS) solution for more than 30 days. FIG. 3A illustrates the colloidal stability of the Pdot-GOx transducer over 30 days. For the purpose of glucose monitoring in vivo, the Pdot-GOx conjugates possessed unparalleled brightness and high sensitivity that permitted facile detection of signals from even small amounts of implanted sensor material. The Pdot transducer also meets the biocompatibility requirements for implantable sensors while providing sufficient luminescence signal for long-term transdermal detection.

Figure 3C:
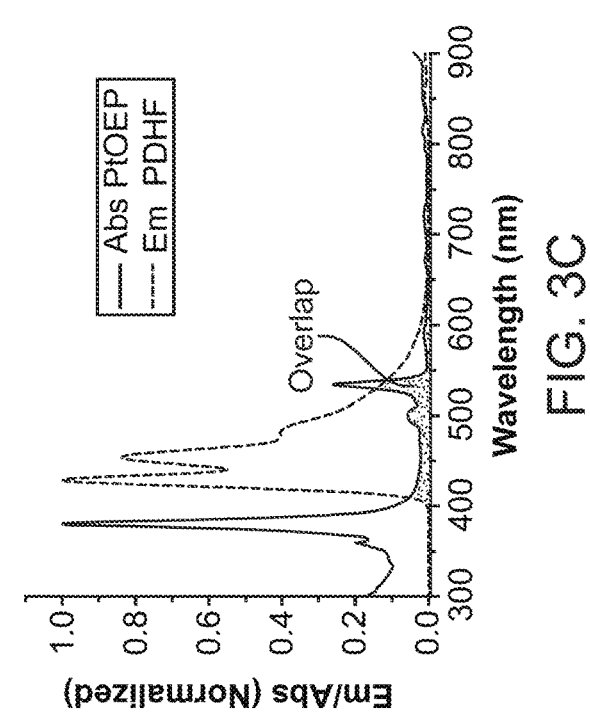

Fluorescence spectroscopy indicated high sensitivity, great selectivity, and tunable dynamic range of the Pdot-GOx assembly for glucose detection in biological fluid. The Pdot transducer exhibited a dominant absorption at 380 nm from PDHF and a major phosphorescence peak at 648 nm from PtOEP. FIG. 3B shows UV-vis absorption and photoluminescence spectra of the Pdot-GOx sensor. The red emission was well separated from the UV excitation, a great advantage for monitoring the emission signal by the naked eye. FIG. 3C illustrates spectral overlap between fluorescence emission of PDHF and absorption of phosphorescent dye PtOEP. This overlap provides energy transfer between the chromophores, allowing UV light absorbed by a PDHF donor to pump a PtOEP acceptor. FIG. 3D illustrates emission spectra of the undoped PDHF Pdots and PtOEP-doped Pdots with an excitation wavelength of 380 nm. Blue fluorescence of the PDHF polymer was significantly quenched because of the efficient Förster resonance energy transfer that occurs from PDHF donor to PtOEP acceptor.

Example 3

Characterization of Nanoparticle Transducers

In this example, spectroscopic and physical properties of a Pdot-GOx nanoparticle transducers were measured. The particle size and morphology of the Pdots were characterized by dynamic light scattering (DLS) and transmission electron microscopy (TEM). Dynamic light scattering was performed using a 1 cm disposable polystyrene cuvette at 25° C. with a Malvern Nano ZS instrument. Zeta potential measurements were conducted on the same Malvern Nano ZS instrument. Samples for TEM measurements were prepared by drop casting the Pdots dispersion onto copper grids. The samples were allowed to dry at room temperature, and then the TEM images were obtained using a Hitachi H-600 microscope operated at 120 kV. UV-vis absorption spectra were recorded with a Schimadzu UV-2550 scanning spectrophotometer using 1 cm glass cuvette. Fluorescence spectra were obtained using a Hitachi F-4500 fluorescence spectrophotometer. Fluorescence spectra of Pdot-GOx at different glucose concentrations were measured 10 minutes after adding glucose to the cuvette with an excitation wavelength of 380 nm. The intensity ratio of red emission to blue emission ($I_{648}/I_{428}$) was calculated to plot the sensitivity curve.

FIG. 4A shows emission spectra of Pdot-GOx transducer at different glucose concentrations. The curves vary from 0 to 20 mM glucose in steps of 2; at the 648 nm peak, the curves are arranged in intensity order from lowest to highest concentration, with 20 mM being the most intense. The Pdot-GOx bioconjugates showed bright red phosphorescence that was sensitive to glucose concentration, while the weak blue fluorescence remained constant. The constant blue fluorescence and the sensitive red phosphorescence lent themselves to ratiometric sensing, which is useful for applications such as the quantitative determination of cellular and tissue glucose levels. FIG. 4B shows a ratiometric calibration plot ($I_{648}/I_{428}$) of the Pdot-GOx transducer as a function of glucose concentration. As indicated in FIG. 4B, the ratio of emission at 648 nm to emission at 428 nm showed a linear relationship with the glucose concentration in the physiologically relevant range of blood glucose, from about 4 mM to about 18 mM. By defining the sensitivity as the slope of the linear part of the curve, the Pdot-GOx sensor showed an intensity change of 20% per mM which placed it among the most sensitive fluorescent glucose sensors. In addition, the dynamic range of the Pdot-GOx assembly can be tuned by varying the molar ratio of GOx to Pdot in the bioconjugation reaction.

FIG. 4C illustrates response curves of the Pdot-GOx to glucose in aqueous suspensions. The Pdot-GOx platform in aqueous environment exhibited a fast glucose response within a few minutes. The sensor response was measured by a general fluorometer after addition of glucose to the Pdot-GOx solution in a cuvette. The response time of the sensor was measured using a 1 cm glass cuvette at 25° C. in HEPES buffer (pH=6.5) with a fluorescence spectrophotometer (Hitachi F-4500, Japan) equipped with a xenon lamp. All response curves were acquired with an excitation wavelength of 380 nm. The fluorescence intensity of Pdot-GOx (10 μg/mL) at 648 nm as a function of time was recorded by adding 30 μL of glucose solution to 3 mL of Pdot-GOx suspensions. Noting that it takes time for glucose to diffuse to the excitation volume, the emission intensity at 648 nm increased to a constant value and plateaued within 10 minutes, indicating a fast response of the sensor in a few minutes. For evaluating the selectivity of Pdot-GOx sensors, fluorescence spectra of Pdot-GOx were measured 10 min after addition of various carbohydrate species (10 mM) with an excitation at 380 nm. The response time was primarily determined by the glucose diffusion and enzymatic reactions.

The Pdot-GOx sensor shows great selectivity against potential interfering substrates, such as different carbohydrate derivatives, because of the specific catalytic reactions of the GOx enzyme. FIG. 4D illustrates the selectivity of the Pdot-GOx transducer for glucose over potential interfering carbohydrates. The high selectivity provides great advantages for in vivo glucose monitoring as compared to, for example, glucose sensing dyes based on boronic acid recognition. Moreover, the operational stability was evaluated by reversible measurements, in which glucose was added to the Pdot-GOx solution for measurement and removed by desalting columns after each cycle. The sensor's response remained unchanged for more than 10 repetitive measurements. The fast and reversible response enabled continuous glucose measurement, allowing for straightforward incorporation into glucose sensors. After 2-month storage at 25° C. and 4° C., the sensor retained more than 95% of its initial response. These results indicated great operational and storage stability of the Pdot-GOx bioconjugates.

Example 4

Nanoparticle Transducers Sensitive to Low Analyte Concentration

Figure 5B:
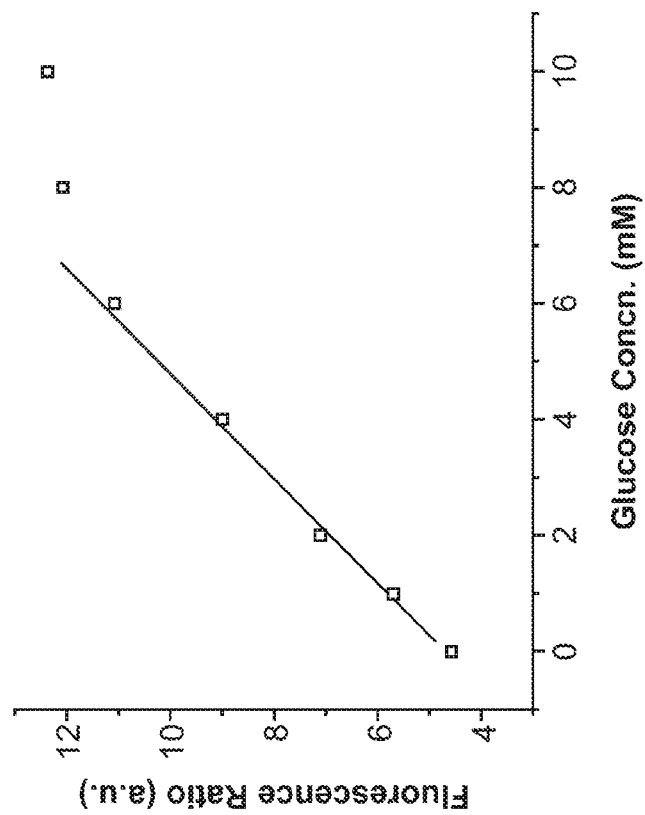
FIG. 5A and FIG. 5B illustrate the use of nanoparticles densely coated with enzymes for sensing at low concentrations.
Figure 5A:
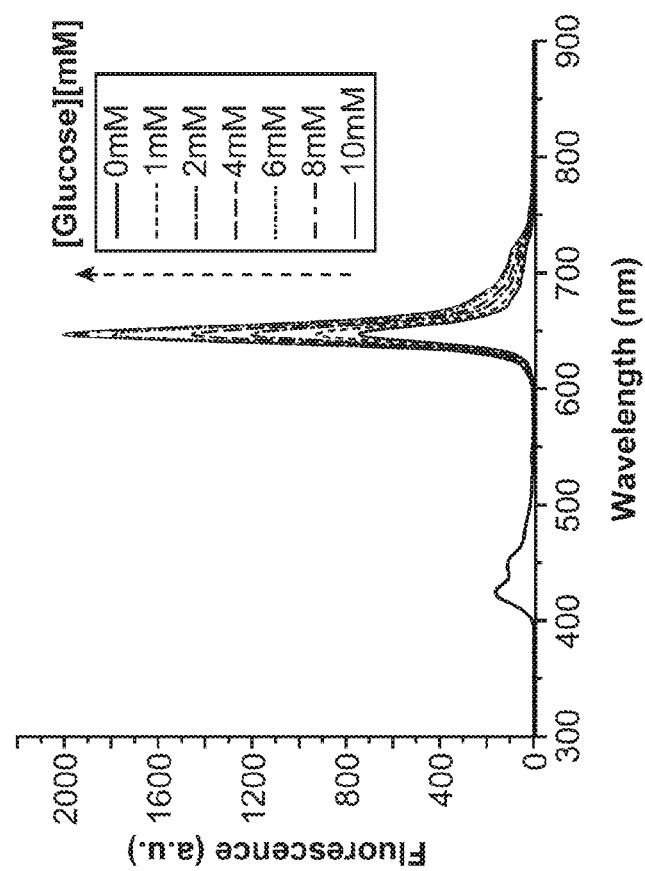

In this example, nanoparticle transducers with selected sensitivity are described—in particular, nanoparticle transducers are provided with analyte sensitivity at a low analytical range. FIG. 5A and FIG. 5B illustrate the use of nanoparticles densely coated with enzymes for sensing at low concentrations. FIG. 5A illustrates emission spectra of Pdots densely coated with GOx at various glucose concentrations, while FIG. 5B shows a ratiometric calibration plot ($I_{648}/I_{428}$) of Pdot-GOx in the low analytical range. As shown in FIG. 5A and FIG. 5B, the Pdots densely coated with GOx show a high sensitivity (25% per mM) in a relatively low analytical range (1-4 mM), which can be useful for glucose monitoring in hypoglycemia.

Example 5

Nanoparticle Transducer Biocompatibility

In this example, experiments are described confirming the biocompatibility for cell lines of the nanoparticle transducers described herein. Biocompatibility is an important factor that determines whether nanoparticle transducers, such as Pdot-GOx nanoparticles for example, can be used as implantable sensor for in vivo glucose monitoring. The cytotoxicity of Pdot-GOx nanoparticles was evaluated using cell viability assays in HeLa cells. The HeLa cell line was used for cellular toxicity studies and intracellular glucose imaging. The cell culture used Dulbecco's modified Eagle's Medium (DMEM) (Life Technologies Gibco, USA) with phenol red supplemented with 10% Fetal Bovine Serum (FBS), 50 U/mL penicillin, and 50 μg/mL streptomycin. The cells were maintained in T75 cell culture flask (NEST, Wuxi China) in an air/$CO_2$ (95:5) atmosphere at 37° C. within an incubator (Thermo scientific, USA). The cells were pre-cultured prior to experiments until confluence was reached.

For cytotoxicity studies, the cells were seeded in 96 well plates (7000 cells in 100 μL per well) for 24 h, and then Pdots, GOx, CAT(catalase), and Pdot-GOx(+CAT) (different final concentrations) were added to the cell culture medium, respectively. Cells were incubated with the various materials for 24 h, followed by the addition of MTT (20 μL, 5 mg/mL, BioSharp, Hefei China) for 3 h. The media was removed and DMSO (150 µL) (Sigma-Aldrich, Shanghai China) was added into each well and gently shaken for 10 min at room temperature to dissolve all formed precipitate. The absorbance at 490 nm was measured by using a microplate reader (BioTek Cytation3, USA). Cell viability was expressed by the ratio of the absorbance of cells incubated with Pdot-GOx solution to that of cells incubated with culture medium only.

FIG. 6A through FIG. 6D illustrate cell viability of HeLa cells treated with various materials including Pdot-GOx transducers. FIG. 6A, FIG. 6B, and FIG. 6C show 24-hour cell viability for cells treated with varying concentrations of Pdot-GOx transducers, GOx, and catalase, respectively. FIG. 6A also illustrates 24-hr cell viability of MCF-7 and GES-1 cells that were subjected to the same protocol as the HeLa cells, and showing no dependence of viability on cell line. As indicated by FIG. 6B, GOx alone induced cell death due to the hydrogen peroxide generation. However, in presence of catalase, the Pdot-GOx nanoparticles (<10 µg/mL) are biocompatible to the cells after 24-hour incubation, as shown in FIG. 6D. In this concentration range, the Pdot-GOx sensor was able to enter into the cells via endocytosis. HeLa cells were incubated with Pdot-GOx nanoparticles for 12 hours in sugar-free culture medium.

For intracellular glucose sensing, $1.5 \times 10^4$ Hela cells were plated onto 22 mm glass-bottom culture dishes coated with poly-L-lysine (NEST, Wuxi China), and allowed to grow overnight (37° C., 5% $CO_2$) in Dulbecco modified Eagle medium (DMEM). Then, the cells were cultured in sugar-free DMEM containing Pdot-GOx (10 µg/mL) and catalase (CAT, 250 kDa, Sigma-Aldrich, Shanghai China) (300 nM) for 12 hours. Glucose was further supplemented to the cell culture (25 mM) for 4-hour incubation. The cells were then washed three times with warm PBS buffer before viewing on fluorescence microscope.

Fluorescence images were acquired on an inverted fluorescence microscope (Olympus IX71, Japan) with a 0.45 NA LUCPLFLN 20× objective. The excitation light was generated from a Mercury lamp, filtered by a band pass filter (Semrock FF01-377/50-25, Rochester, N.Y. USA). Fluorescence signal was filtered by a band pass filter (Semrock FF01-655/40-25, Rochester, N.Y. USA), and imaged on an Andor iXon3 frame transfer EMCCD (Andor, UK).

FIG. 7A through FIG. 7C illustrate intracellular glucose sensing in HeLa cells. FIG. 7A shows HeLa cells without Pdot-GOx incubation as a control group, and FIG. 7B shows cells incubated with Pdot-GOx nanoparticles for 24 hours in a sugar-free medium. As shown in FIG. 7, fluorescence imaging indicated apparent internalization of the Pdot-GOx nanoparticles by the cells. Glucose was then supplemented into the media of the cultured cells. FIG. 7C shows cells incubated with Pdot-GOx for 24 hours and supplemented with glucose for 4 hours. As compared with the cells which did not receive glucose, the intracellular luminescence was greatly enhanced, indicating successful detection of intracellular glucose by the Pdot-GOx sensor.

Example 6

Biocompatibility in an In Vivo Murine Model

In this example, experiments are described confirming the biocompatibility of the nanoparticle transducers described herein for use in vivo for continuous analyte monitoring, using murine subjects. All animal experiments involved 8-week-old BALB/c male mice (Vital River Laboratories (VRL), Beijing China), weighing around 25 g. Experimental group size includes three animals per treatment, balancing sufficient replication of results with a reduction in animal number. All animals imaged were included in the analyses. Animals were fasted for 8 h before imaging for in vivo glucose monitoring. Each mouse was anesthetized with intraperitoneal injection of 100 µL chloral hydrate (10 wt %). Thereafter, 200 µL of Pdot-GOx (50 µg/mL) was injected subcutaneously into the dorsal side of the mouse for continuous in vivo glucose monitoring.

Because of the extraordinary brightness, the Pdot transducer in the microgram range was transdermally detectable; three implantation sites with different concentrations were clearly distinguished with a small-animal imaging system. Fluorescence animal imaging was acquired with a custom built small-animal imaging system equipped with an Andor iKon-M frame transfer CCD (Andor iKon-M 934, UK) and xenon light source (Asahi Spectra MAX-303, Japan). Twenty five minutes after the anesthesia administration, fluorescence imaging was performed by using an exposure time of 5 s, with an excitation of 543 nm and emission at 655 nm. Right after the imaging, a blood sample was collected from the tail of the mice using a scalpel quickly remove up to 1 cm of the tail, and blood glucose concentration was measured by using a standard glucose meter (Accu-Chek, Roche Diagnostics). Afterwards, the mice were treated intraperitoneally with 200 µL of sterilized glucose solution (1 M) to increase blood glucose concentrations. After fifteen minutes, 100 µL of sterilized solutions of insulin in saline (0.5 U/mL, Wanbang Biopharmaceuticals, Xuzhou China) was injected intraperitoneally to decrease blood glucose concentration. During the process, we captured fluorescence images and measured the blood glucose concentrations every 5 minutes, until the blood glucose concentration was back into the normal range. For animals in the control group, mice were injected the same dose of sterilized saline instead of glucose and insulin at the same time. Fluorescence imaging was performed following the same procedure. Animals were euthanized through injection of overdose anesthetics after the glucose monitoring experiment.

Figure 9:
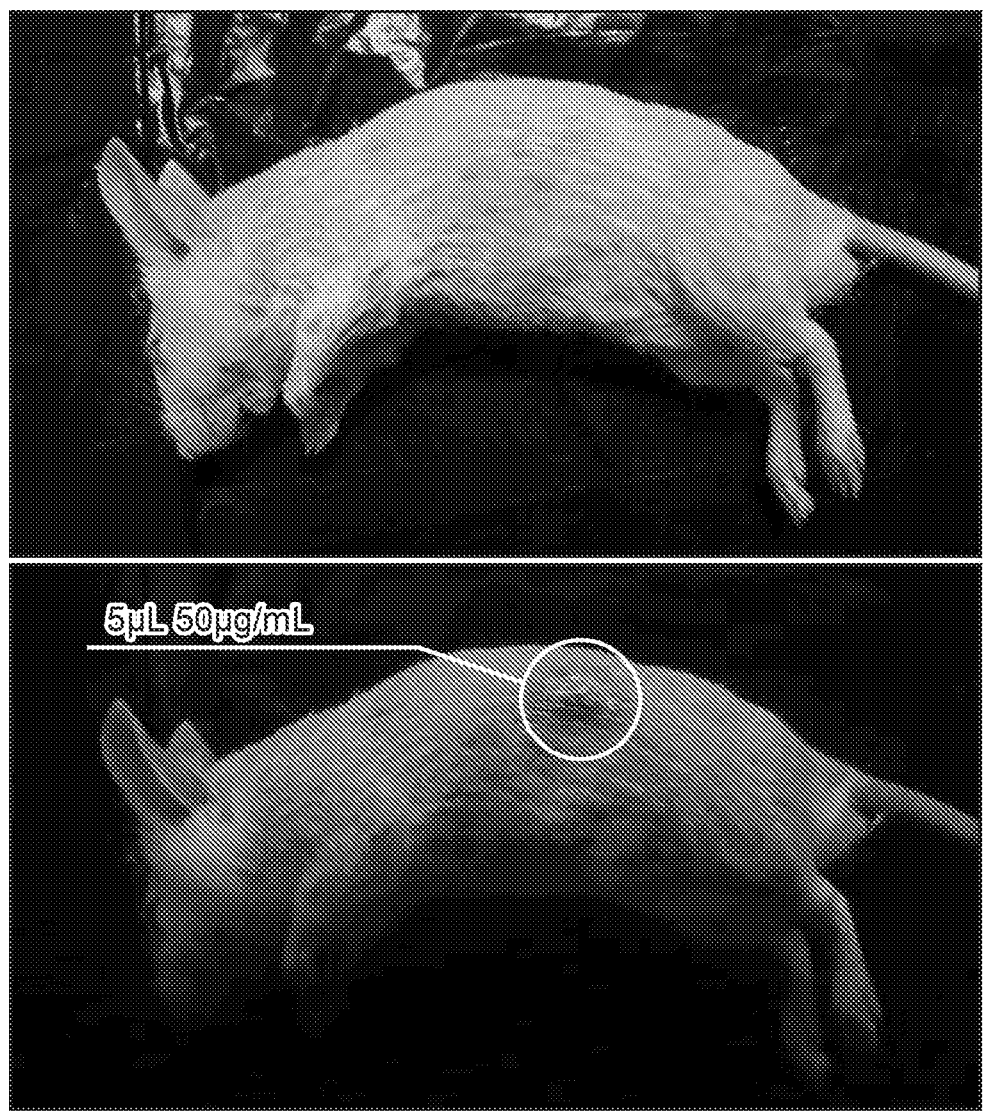
FIG. 9 shows images of a mouse subcutaneously injected with nanoparticle transducers under room light (top) and UV (bottom).

FIG. 8A and FIG. 8B illustrate fluorescent imaging of a mouse injected subcutaneously with Pdot-GOx transducers. FIG. 8A illustrates fluorescent imaging of the with three injection sites of Pdot-GOx transducers at different concentrations, and FIG. 8B shows fluorescent intensity of the three different sites injected with Pdot-GOx. In fact, 0.25 µg (5 µL of 50 µg/mL) of Pdot-GOx was even visible to the naked eye with UV lamp excitation through the skin layer and hair. FIG. 9 shows images of a mouse subcutaneously injected with nanoparticle transducers under room light (top) and UV (bottom), in which the fluorescence of the nanoparticle transducers is clearly visible. Being able to use a minute amount of material for implantation helps to reduce inflammation at the implantation site and meet the biocompatibility requirement of implantable sensors.

The in vivo response of the Pdot-GOx assembly to blood glucose fluctuations in live mice was demonstrated by whole-animal biophotonic imaging. The blood glucose levels of the mice were elevated to ~20 mM, which is within the hyperglycemic range, by intraperitoneal injection of glucose. The blood glucose levels were then decreased to ~10 mM, which is within the euglycemic range, with an insulin injection. For comparison, blood glucose concentrations were measured every 5 minutes with a commercial glucose meter using blood samples from snipped tails. As a starting point, a fluorescence image of the implanted Pdot-GOx sensor in live mice was captured at the 25th minute after the anesthesia administration. Afterwards, the mice were treated intraperitoneally with 200 µL of sterilized glucose solution (1 M) to increase the blood glucose level. After 15 minutes, 100 μL of sterilized insulin in saline (0.5 U/mL) was administered intraperitoneally to decrease the blood glucose level.

Figure 10A:
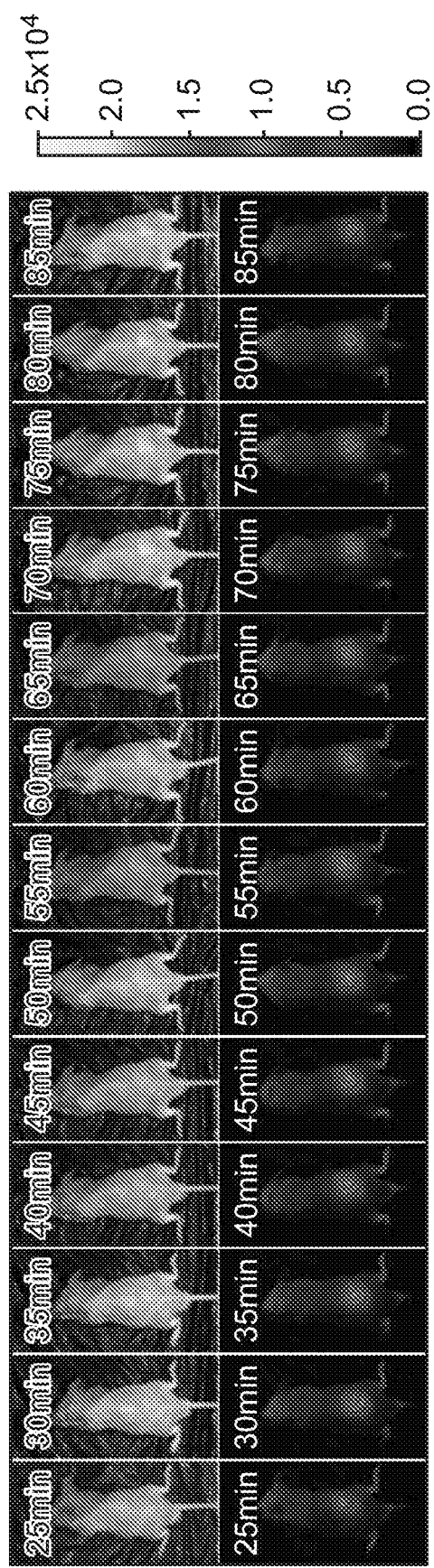
FIG. 10A through FIG. 10D illustrate in vivo continuous glucose monitoring in live mice.
Figure 10B:
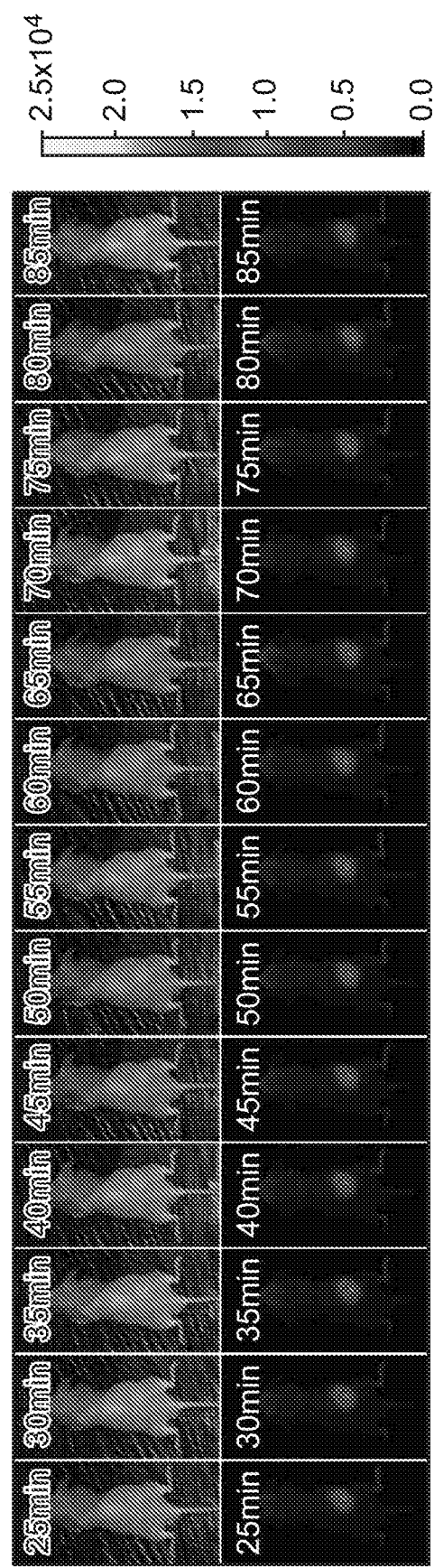
Figure 10D:
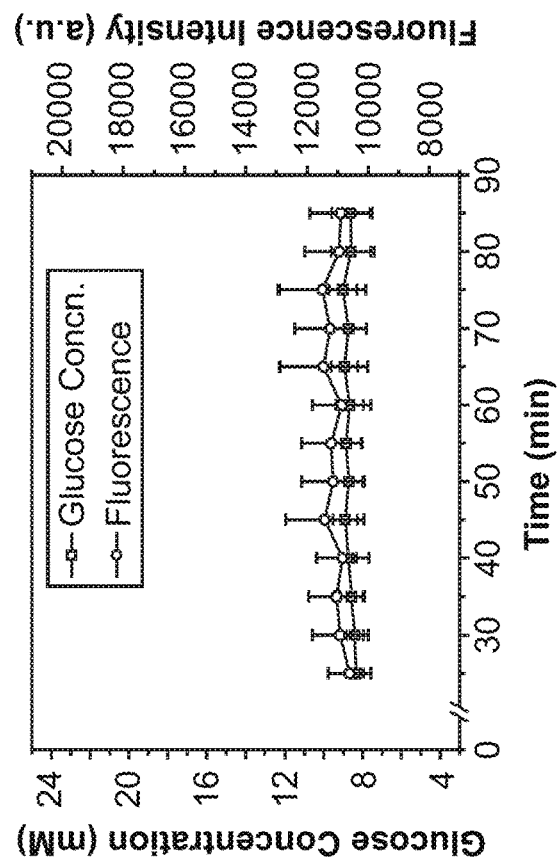
Figure 10C:
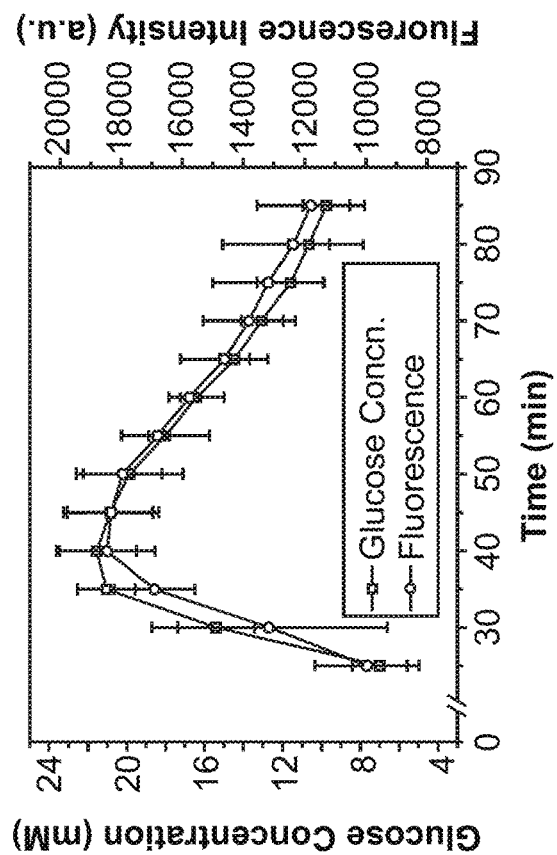

During the entire process, fluorescence images were captured every 5 minutes to monitor the changes in blood glucose concentration. FIG. 10A and FIG. 10B show the fluorescence images of the mice with and without glucose/insulin treatment, respectively. As indicated by imaging results, the fluorescence signal increased right after glucose administration and decreased to the original level after the injection of insulin. In contrast, the fluorescence from the mouse without glucose/insulin remains unchanged. FIG. 10C shows the averaged luminescence intensities and standard deviations of the Pdot-GOx sensor as a function of the blood glucose concentration in three mice with glucose and insulin administrations. As clearly indicated in the figure, the luminescence intensity (circles) closely correlated with the blood glucose level (squares) and constantly tracked the concentration change with the blood glucose fluctuations. For the mice not receiving a glucose injection, both the luminescence intensity and glucose concentration remained relatively constant, as shown in FIG. 10D. These observations unambiguously confirmed the excellent in vivo response of the Pdot-GOx sensor, which provided sufficient signal and sensitivity to transdermally monitor the change of blood glucose concentrations.

Example 7

Pharmacokinetics and Stability of Nanoparticle Transducers

The pharmacokinetics and in vivo distribution of the Pdot-GOx nanoparticles after subcutaneous injection were evaluated. FIG. 11 illustrates long-term glucose monitoring and in vivo distribution. The mice were sacrificed 30 days after the sensor implantation. For biodistribution studies, the mice after the glucose monitoring experiments were euthanized by overdose anesthetics. The organs and tissues (heart, liver, spleen, lungs, kidneys, thigh muscle, and skin tissue near the implantation site) were resected for fluorescence imaging analysis. At last, the excised organs and tissues were placed in formalin for histology and fluorescence analysis.

The resected organs and tissues were fixed in 10% buffered formalin overnight. Tissue is dehydrated through a series of graded ethanol baths, cleared using xylene, and then infiltrated with wax. The infiltrated tissues are then embedded into wax blocks. The tissues are then cut into 5 μm sections using a microtome, and stained with hematoxylin and eosin (H&E). The histological sections were observed under an optical microscope. To access the sensor distribution in the main organs and tissues following subcutaneous administration, fluorescence imaging was also employed for analyzing. Fluorescence images of the tissue sections without H&E staining were captured on a fluorescence microscope with a UV excitation filter (375 nm) and red emission filter (655 nm). Subcutaneous tissue and various organs were resected for biophotonic imaging.

FIG. 11A shows fluorescence images of excised organs and skin tissue of the mice subcutaneously injected with Pdot-GOx transducers (bottom) or sterilized, phosphate-buffered saline (top). As shown by the images, a strong fluorescence was only observed from the subcutis, indicating the Pdot-GOx remained at the implantation site for as long as a month. At this time point, no significant differences were observed in various organs, including the liver, spleen, lung, kidney, heart, and muscle, compared with the control animals, as shown in FIG. 11B.

Figure 12:
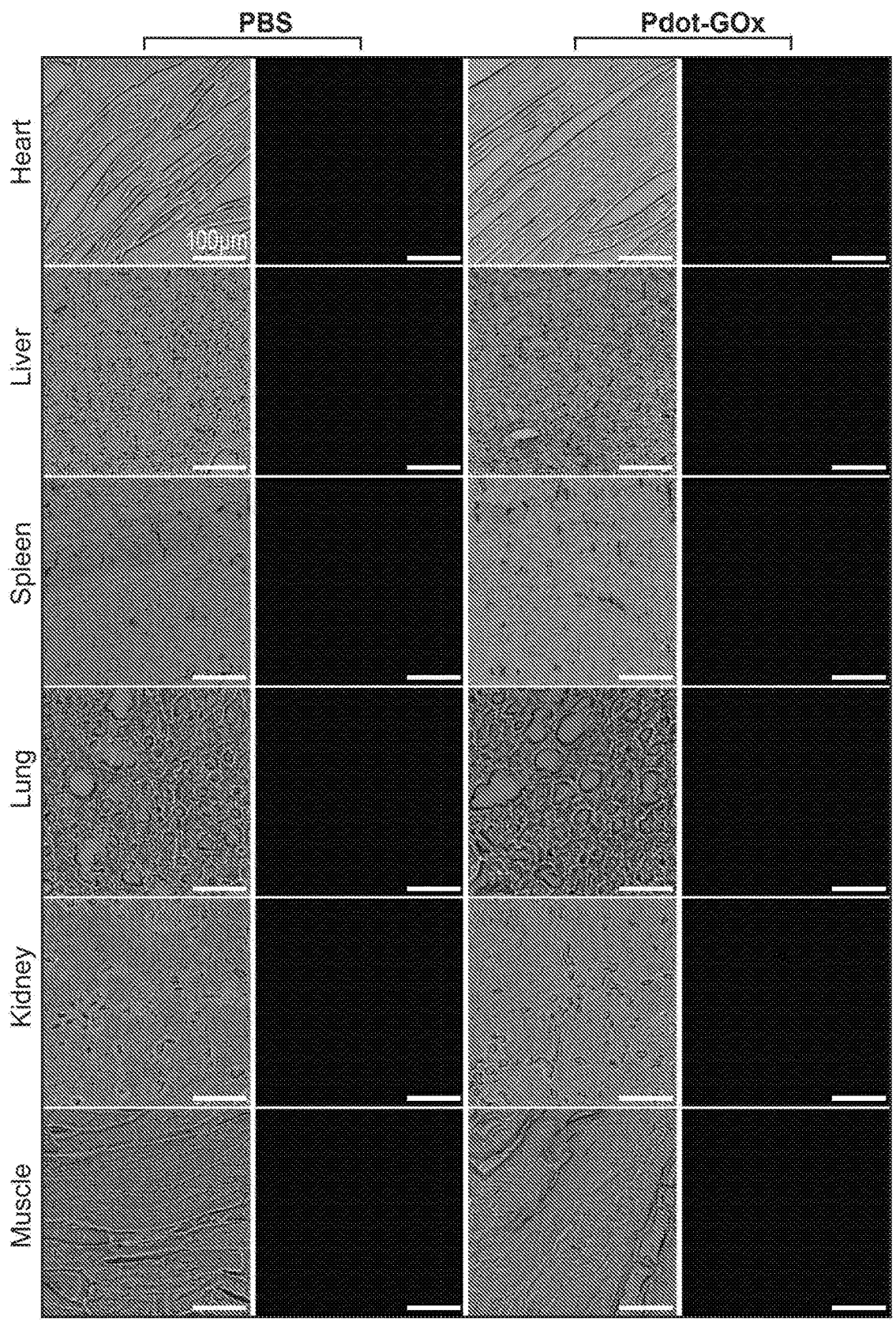
FIG. 12 shows a histochemical analysis on tissue sections of the mouse 30 days after the nanoparticle transducer injection.

Further microscopic examinations on the tissue sections showed no detectable luminescence from these organs, consistent with the biophotonic imaging results. FIG. 12 shows a histochemical analysis on tissue sections of the mouse 30 days after the nanoparticle transducer injection. The in vivo distribution study indicated the Pdot-GOx nanoparticles were predominantly trapped in the subcutaneous implantation site and did not enter the peripheral blood. The water molecules in the injected solution can be rapidly absorbed by peripheral tissue, resulting in stable nanoparticle assemblies with little diffusion. This observation is consistent with the conclusion that Pdot aggregates on substrates have low solubility, even in organic solvent.

The Pdot-GOx assembly at the implantation site showed sensitive glucose detection for long periods of time, which has been a major goal in development of continuous glucose monitors. Biophotonic imaging was performed at designated time intervals: 7, 15, and 30 days post injection of the Pdot-GOx sensor. FIG. 13A through FIG. 13C show fluorescence imaging of a live mouse at 7 days (FIG. 13A), 15 days (FIG. 13B), and 30 days (FIG. 13C) after injection with nanoparticle transducers.

The implanted Pdot-GOx assembly exhibited great response without noticeable sign of degradation for 7 and 15 days, as shown in FIG. 11C and FIG. 11D, respectively, with fluorescence (circles) closely tracking glucose (squares). After 30 days, the luminescence intensity of the sensor still closely correlated with the blood glucose level and constantly tracked the concentration change, with only a small decrease in sensitivity from the relatively small intensity change versus glucose variation in the up-and-down cycle, as shown in FIG. 11E. This minor degradation is likely due to decreased catalytic activity of the enzyme on the Pdot surface. FIG. 11F illustrates hematoxylin and eosin staining of organ sections excised from the mouse with the Pdot-GOx injection (right) and the control group with PBS injection (left). Neither noticeable organ damage nor inflammation was observed as compared to the control group. The histological analysis revealed no toxicity effects in the main organs and tissues, indicating biocompatibility with the Pdot materials.

Example 8

Figure 14A:
FIG. 14A shows in vivo glucose measurement with a miniaturized fluorometer.
Figure 14B:
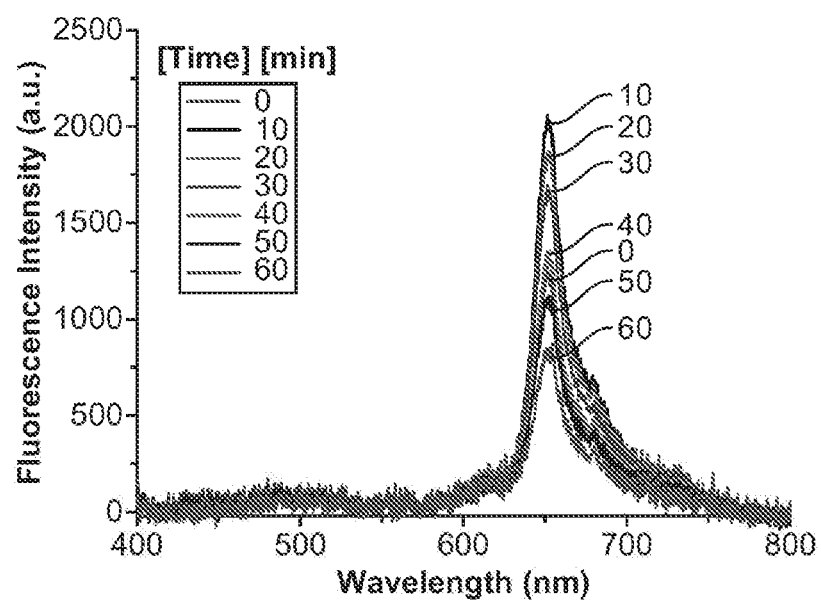
FIG. 14B illustrates the kinetic change of fluorescence emission spectra of implanted Pdot-GOx transducer in a live mouse, under excitation at 385 nm.
Figure 14C:
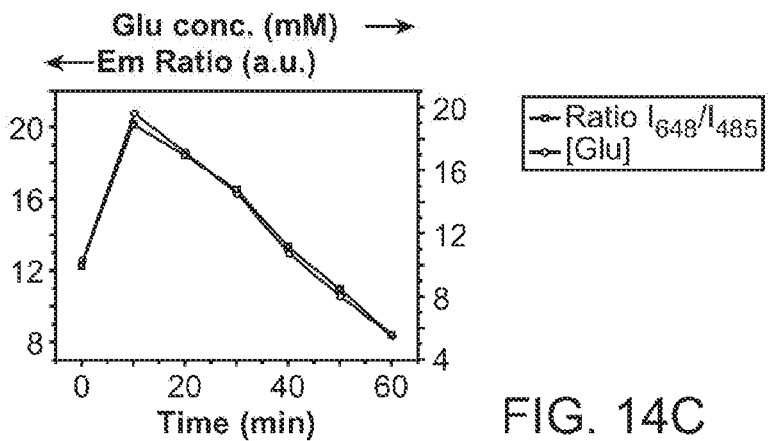
FIG. 14C shows the intensity ratio change (650 nm relative to 480 nm) of the implanted Pdot-GOx transducer in live mouse after glucose and insulin injection.

Nanoparticle Transducers for Glucose Concentration Monitoring with a Portable Device Nanoparticle transducers allow quantitative measurement of in vivo glucose concentration, even without sophisticated imaging instrumentation, as illustrated in this example. A portable optical-fiber-based microspectrometer was used to detect the glucose response of subcutaneously implanted Pdot-GOx assembly. FIG. 14A shows pictures of a mouse subcutaneously injected with Pdot-GOx under UV light (385 nm). Under the same protocol as used for in vivo imaging, the emission spectra of the implanted Pdot-GOx sensors were measured by collecting the transdermal fluorescence signal. FIG. 14B illustrates the kinetic change of fluorescence emission spectra of implanted Pdot-GOx transducer in a live mouse, under excitation at 385 nm, along with an inset showing the intensity ratio change (650 nm relative to 480 nm) of the implanted Pdot-GOx transducer in live mouse after glucose and insulin injection. As shown in FIG. 14B, the emission intensity at 650 nm clearly reflected the fluctuations of glucose level due to the effects of glucose and insulin. The highest peak is at 10 minutes, with each 10 minute interval dropping smoothly thereafter as glucose levels are decreased by the insulin (with the exception of the 0 minute measurement). The spectra and glucose levels at 0 and 40 minutes are approximately equal, and the lowest intensity curve corresponds to the 60 minute measurement. The blue emission at 480 nm remained constant and can be used as an internal reference for ratiometric measurement. FIG. 14C shows the intensity ratio change (650 nm relative to 480 nm) of the implanted Pdot-GOx sensor in live mouse after glucose and insulin injection. The results also closely follow the rise and decrease of the blood glucose as measured by a glucose meter using blood samples from the snipped tail. The rapid and quantitative measurement with a compact and portable micro-spectrometer is particularly desirable for system integration with smartphones or development of wearable devices.

Example 9

Further Chromophore and Enzyme Examples for Nanoparticle Transducers

This example illustrates several additional nanoparticle transducers using alternative chromophore arrangement. The examples described are not exhaustive, but merely illustrate a broad range of structures that can be formed using the techniques described herein. Although GOx is provided as an exemplary enzyme for the detection of glucose, alternative enzymes can be provided for monitoring of other analytes; for example, the glucose sensitivity described herein can be replaced with an alternative analyte by swapping the GOx enzyme with an enzyme that oxidizes the alternative analyte, thereby consuming oxygen and causing a change in fluorescence of the associated chromophore. In this manner, any oxygen-sensitive chromophore can be used to provide a transducer fluorescence signal when combined with an oxygen-consuming enzyme for the detection of an arbitrary analyte, where the enzyme catalyzes an oxygen-consuming reaction with the analyte.

Figure 15B:
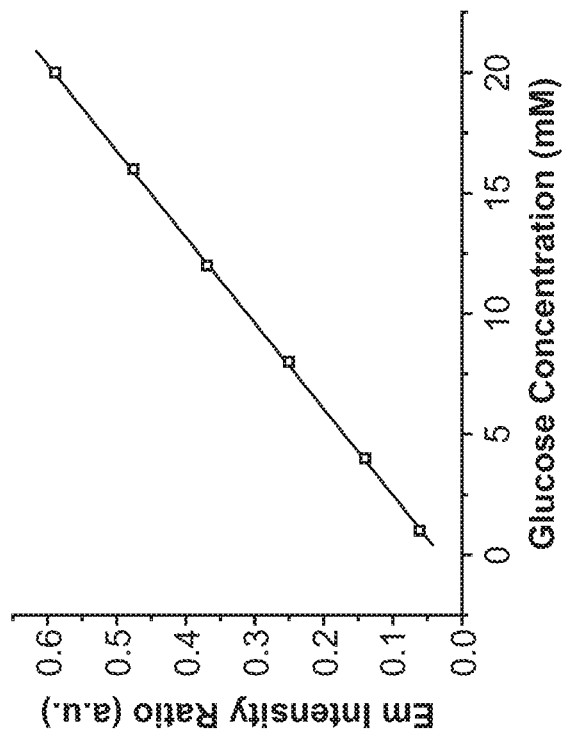
FIG. 15A and FIG. 15B show fluorescence emission from nanoparticle transducers with chromophores comprising do-PFO, 10% PdOEP, and 10% PSMA in a Pdot-GOx transducer for the detection of glucose.
Figure 15A:
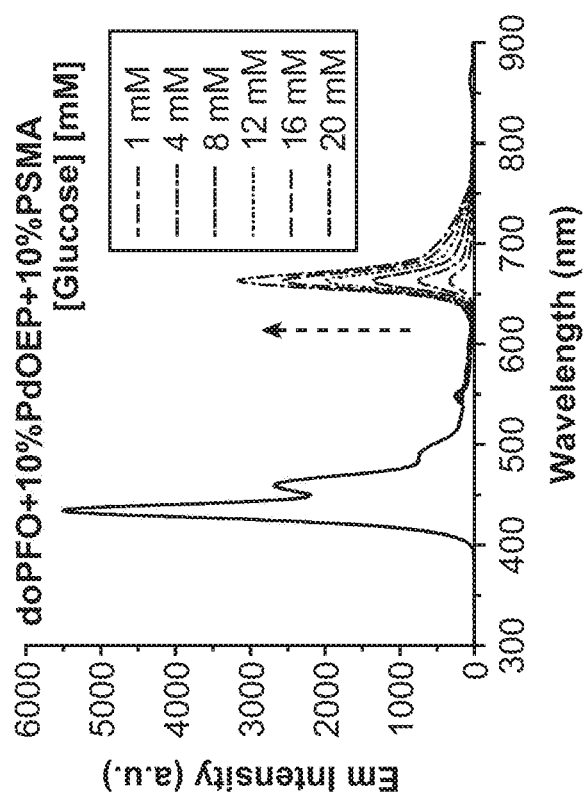
Figure 15C:
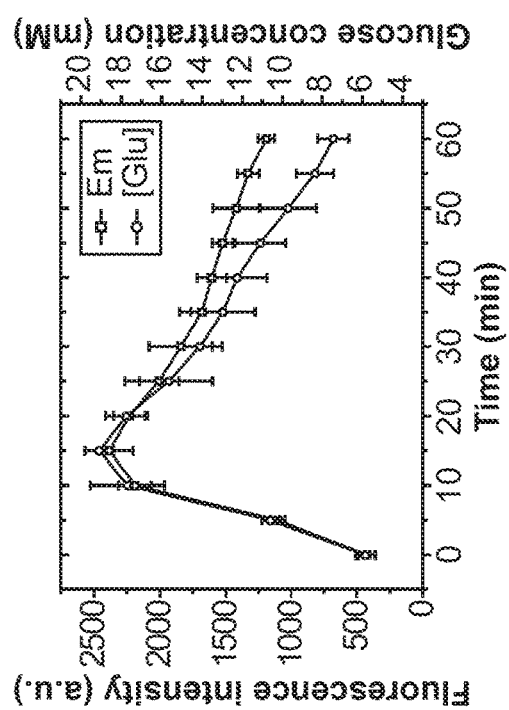
FIG. 15C shows in vivo murine response data showing an emission curve substantially tracking measured glucose concentration.
Figure 15D:
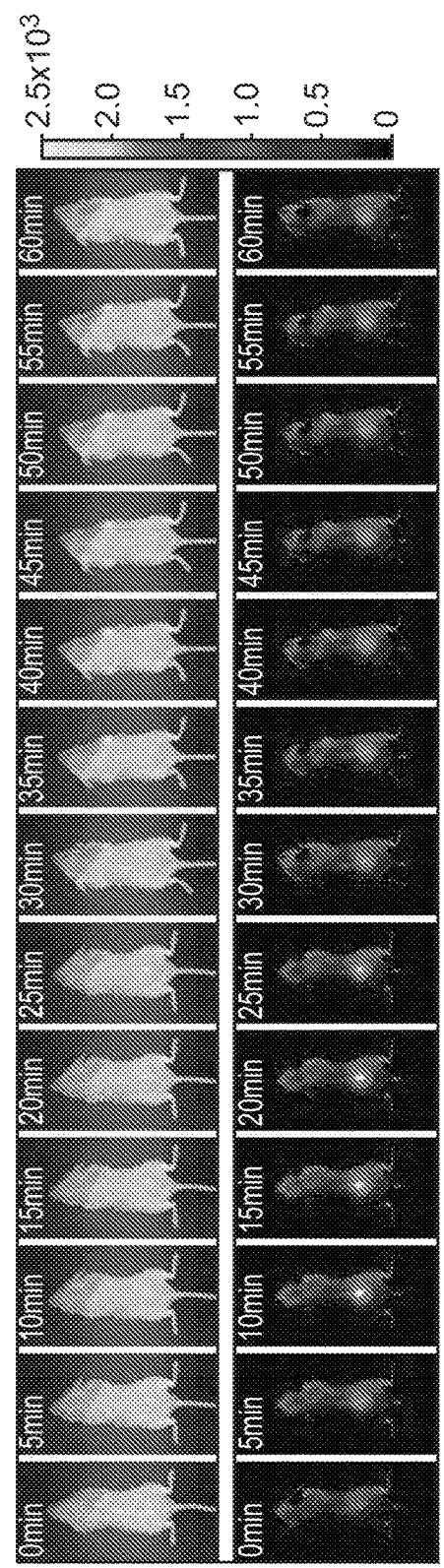
FIG. 15D shows images with time data for mice receiving glucose (top images) and a control group not receiving glucose (bottom images).

FIG. 15A through FIG. 15D show fluorescence emission from nanoparticle transducers with chromophores comprising do-PFO, 10% PdOEP, and 10% PSMA in a Pdot-GOx transducer for the detection of glucose. FIG. 15A shows emission spectra for a plurality of glucose concentrations. FIG. 15B shows a calibration plot of said transducers detecting glucose over a range of concentrations from 0 mM to about 20 mM, showing a ratiometric response curve throughout the range. FIG. 15C shows in vivo murine response data showing an emission curve substantially tracking measured glucose concentration. FIG. 15D shows images with time data for mice receiving glucose (top images) and a control group not receiving glucose (bottom images).

Figure 16B:
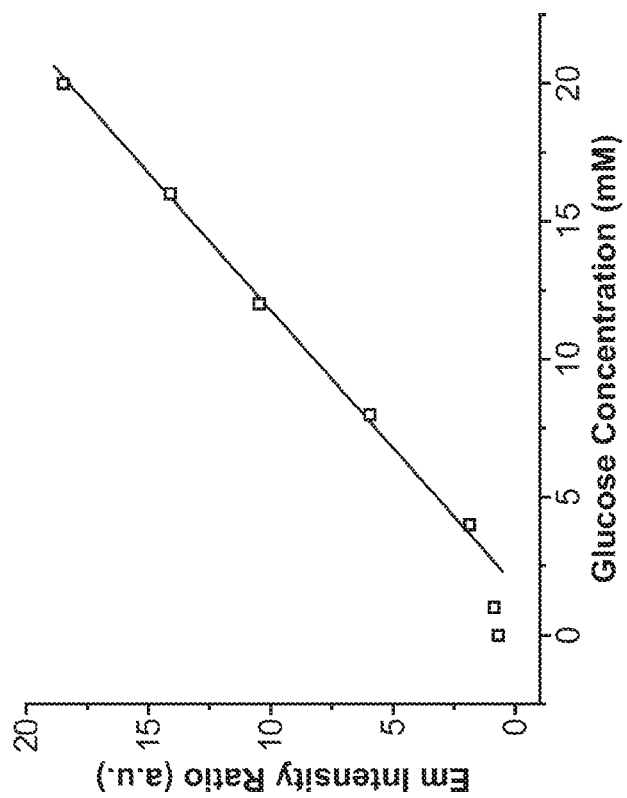
FIG. 16A and FIG. 16B show fluorescence emission from nanoparticle transducers with chromophores comprising PSMA, 1% PdOEP, and 0.1% Coumarin 1 in a Pdot-GOx transducer for the detection of glucose.
Figure 16A:
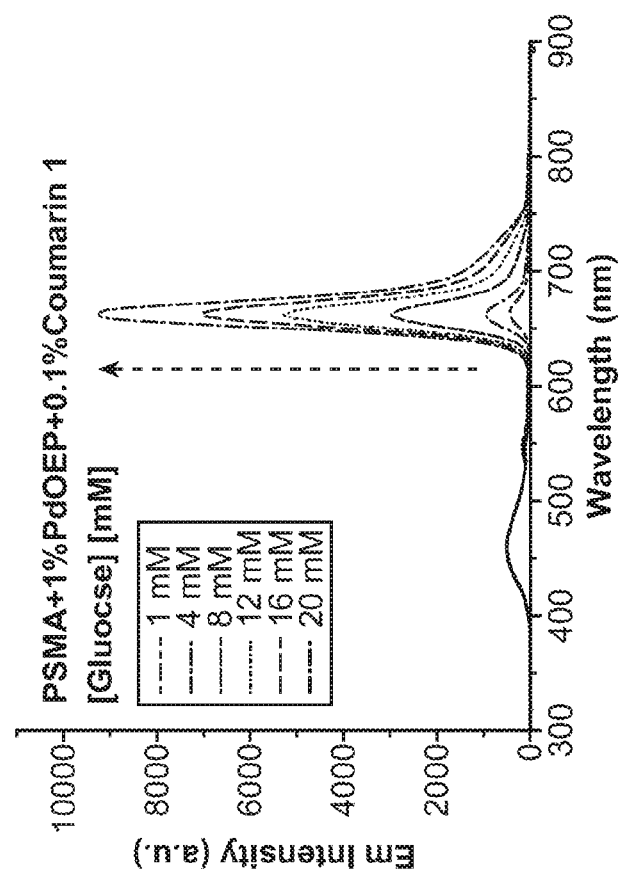

FIG. 16A and FIG. 16B show fluorescence emission from nanoparticle transducers with chromophores comprising PSMA, 1% PdOEP, and 0.1% Coumarin 1 in a Pdot-GOx transducer for the detection of glucose. FIG. 16A shows emission spectra for a plurality of glucose concentrations. FIG. 16B shows a calibration plot of said transducers detecting glucose over a range of concentrations from 0 mM to about 20 mM, showing a ratiometric response curve.

Figure 17B:
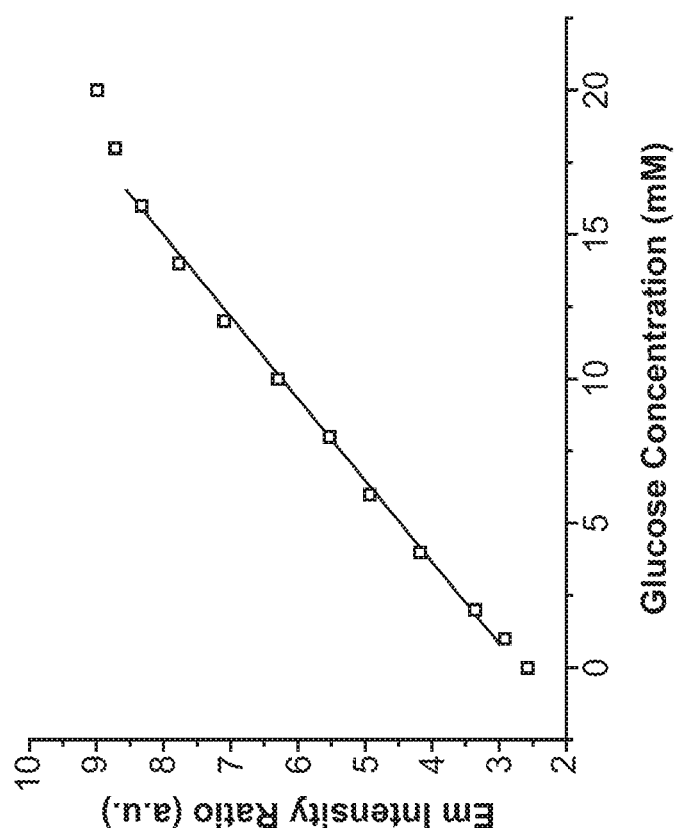
FIG. 17A and FIG. 17B show fluorescence emission from nanoparticle transducers with chromophores comprising PSMA, 1% PtOEPK, and 0.1% NileRed in a Pdot-GOx transducer for the detection of glucose.
Figure 17A:
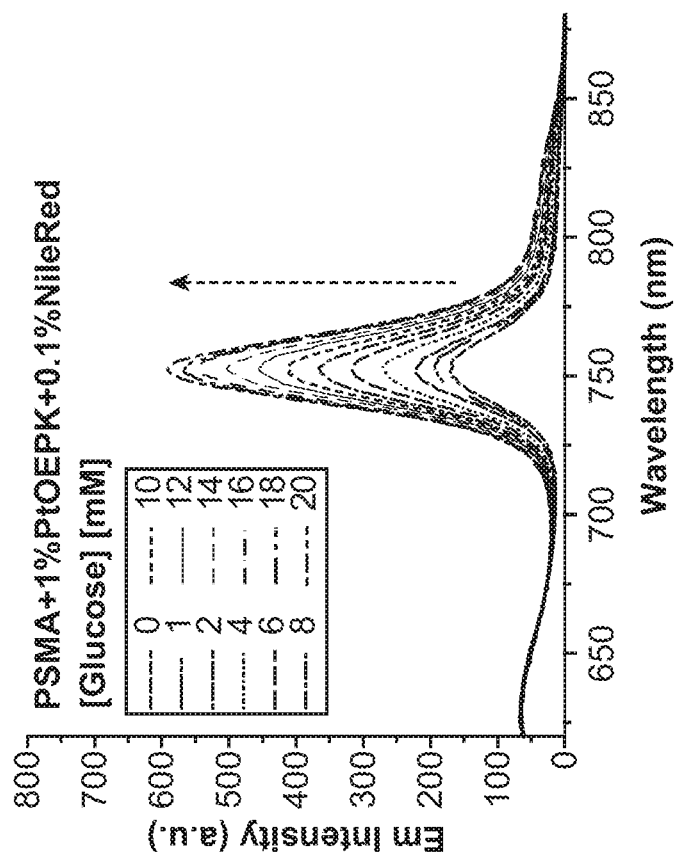

FIG. 17A and FIG. 17B show fluorescence emission from nanoparticle transducers with chromophores comprising PSMA, 1% PtOEPK, and 0.1% NileRed in a Pdot-GOx transducer for the detection of glucose. FIG. 17A shows emission spectra for a plurality of glucose concentrations. FIG. 17B shows a calibration plot of said transducers detecting glucose over a range of concentrations from 0 mM to about 20 mM, showing a ratiometric response curve.

Example 10

Nanoparticle Sensors for Detection of Reactive Analytes

In a further aspect of the disclosure, nanoparticle sensors are provided that enable the detection of reactive analytes without requiring catalytic enzymes. Nanoparticle sensors can be employed to detect ascorbic acid, for example, by providing a nanoparticle such as a Pdot comprising an oxygen-sensitive chromophore. As ascorbic acid is a reducing agent, it spontaneously reacts to consume oxygen. Accordingly, said sensors can be used to detect the presence of ascorbic acid; for example, when the ascorbic acid is present in pharmaceutical quantities.

Figures 18A, 18B:
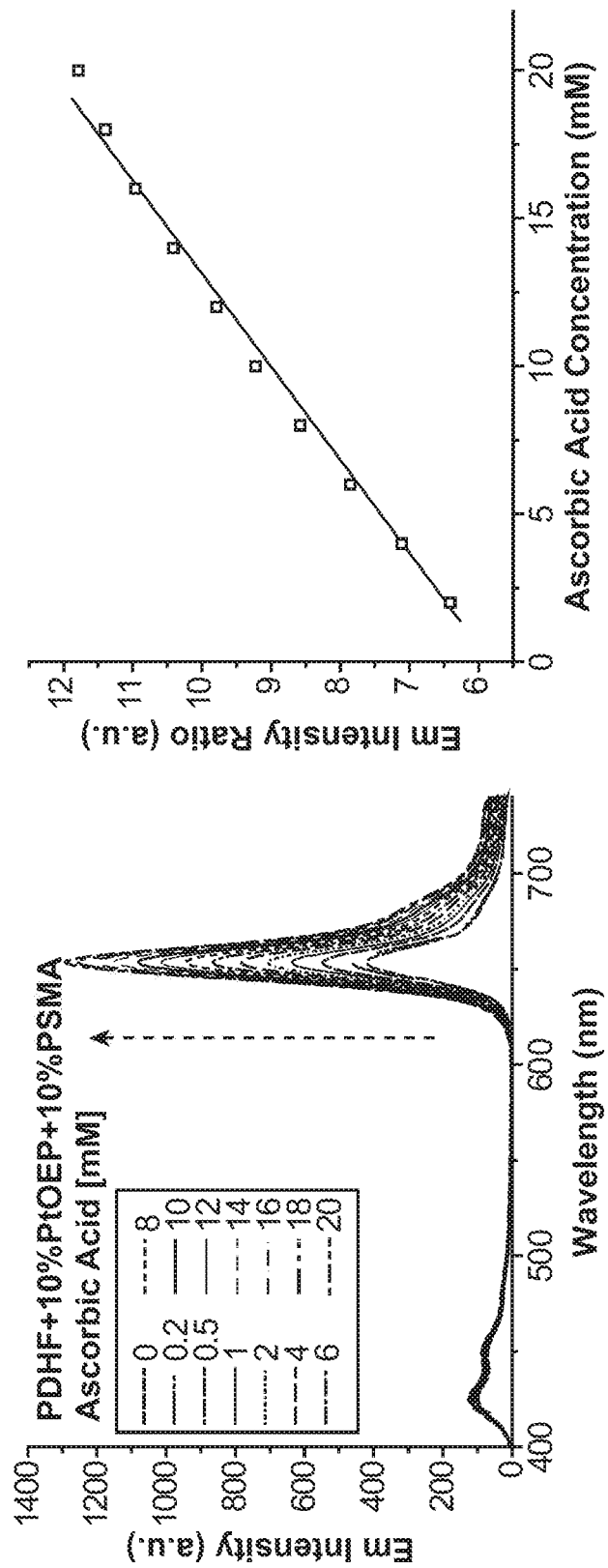
FIG. 18A and FIG. 18B show fluorescence emission from nanoparticle transducers with chromophores comprising PDHF, 10% PtOEP, and 10% PSMA in a nanoparticle sensor for the detection of ascorbic acid.

FIG. 18A and FIG. 18B show fluorescence emission from exemplary nanoparticle sensors with chromophores comprising PDHF, 10% PtOEP, and 10% PSMA in a Pdot nanoparticle sensor for the detection of ascorbic acid. FIG. 18A shows emission spectra for a plurality of ascorbic acid concentrations. FIG. 18B shows a calibration plot of said sensors detecting ascorbic acid over a range of concentrations from about 2 mM to about 20 mM, showing a ratiometric response curve throughout the range.

Figure 19A:
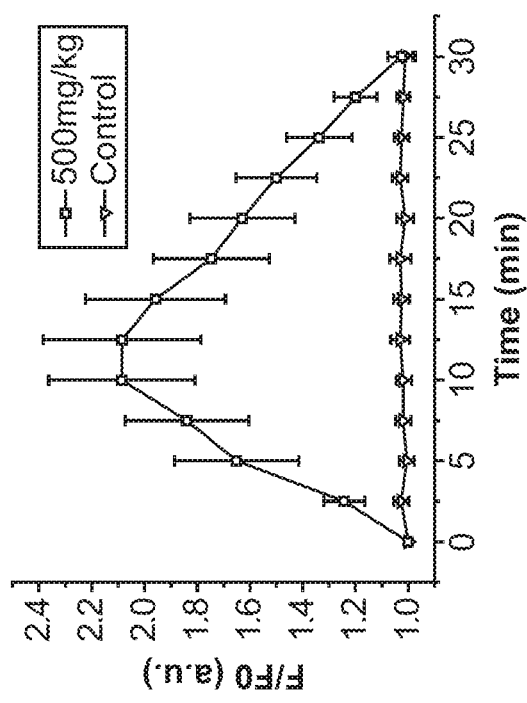
FIG. 19A and FIG. 19B illustrate in vivo continuous ascorbic acid monitoring in live mice using nanoparticle sensors.
Figure 19B:
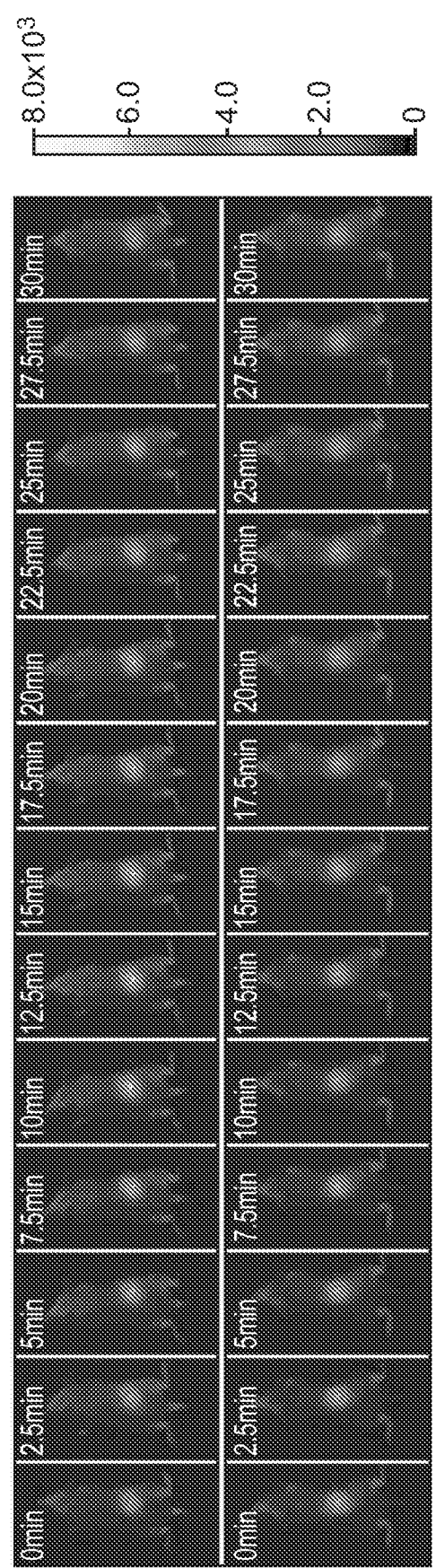

FIG. 19A and FIG. 19B illustrate in vivo continuous ascorbic acid monitoring in live mice using nanoparticle sensors. FIG. 19A illustrates fluorescence intensities of the injected nanoparticle sensors in live mice with the administration of different concentrations of ascorbic acid. FIG. 19B shows in vivo fluorescence imaging of varying ascorbic acid concentrations in a live mouse with injected Pdot sensors.

Figure 20B:
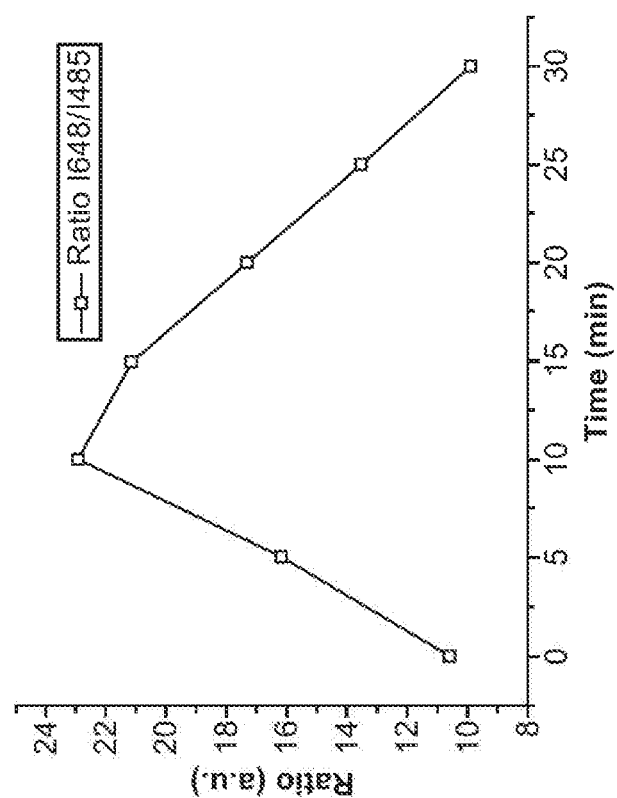
FIG. 20A and FIG. 20B illustrate ascorbic acid blood concentration monitoring by a miniaturized optical detection system.
Figure 20A:
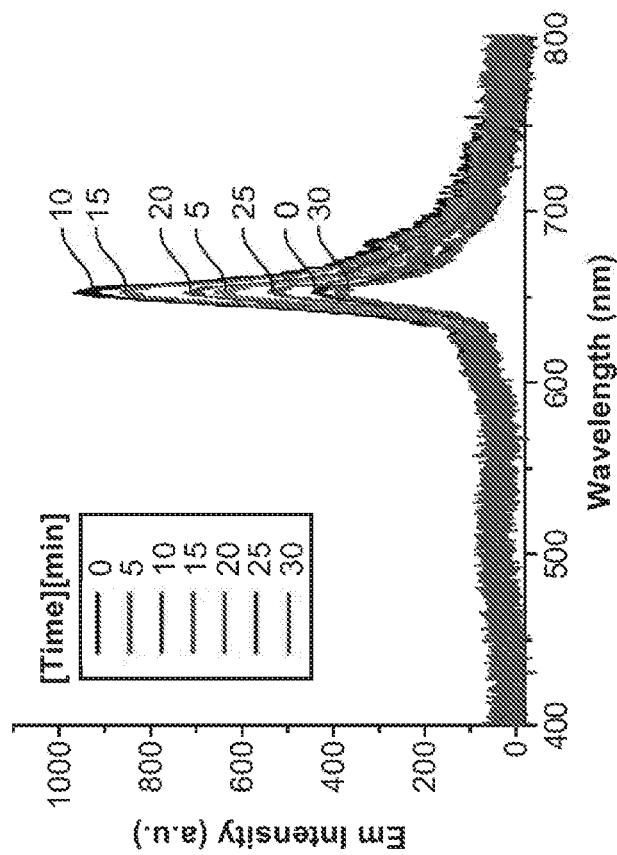

FIG. 20A and FIG. 20B illustrate ascorbic acid blood concentration monitoring by a miniaturized optical detection system. FIG. 20A shows the kinetic change of fluorescence emission spectra of injected Pdots in a live mouse to blood concentration of ascorbic acid, under excitation at 385 nm. FIG. 20B shows fluorescence intensity response as a function of time to blood concentration of ascorbic acid after intravenous administration thereof. Accordingly, in vivo detection of ascorbic acid with nanoparticle sensors comprising oxygen-sensitive chromophores has been demonstrated.

Example 11

Wearable Device for Glucose Monitoring of a Subject Using Nanoparticle Transducers The long term stability, high reliability, and rapid, reversible response of the nanoparticle transducers described herein allow for the use of Pdot-GOx transducers for in vivo glucose monitoring. In this example, Pdot-GOx transducers are injected subdermally, allowing for continuous transdermal monitoring by a probe employing transdermal UV illumination and detecting emitted fluorescence to determine blood glucose levels continuously, as demonstrated in the in vivo tests described. A wearable device is provided comprising an optical sensor sensitive to the fluorescence emission of the Pdot-GOx transducer, and an illumination source to provide light at a wavelength that provides energy for the fluorescence of the nanoparticles. The optical sensor is adapted to detect fluorescence transmitted through the skin of a subject to allow continuous transdermal monitoring of blood glucose. The optical sensor is coupled to a processor and memory disposed within the device. The memory comprises instructions that, when executed, cause the processor to use the optical sensor to measure fluorescence emitted by the plurality of Pdot-GOx transducers in response to the presence of glucose and illumination from the light source. The device further comprises a battery to provide electrical power.

Example 12

Nanoparticle Transducers as a Glucose Sensor for an Artificial Pancreas

In this example, Pdot-GOx transducers are employed in an artificial pancreas as a glucose sensor, providing a feedback loop to trigger dispensing of insulin at high measured glucose or stopping of insulin dispensation at low measured glucose. The device comprises an alarm function that is triggered in response to glucose exceeding or falling below predetermined thresholds. The artificial pancreas is an implantable device comprising a glucose-sensitive nanoparticle transducer, an illumination source providing UV light, and an optical detector adapted to detect fluorescence at the nanoparticle emission wavelengths. The device further comprises a processor to determine blood glucose levels from the measured fluorescence, using calibration curves similar to those described herein, and to regulate the dispensation of insulin from a storage chamber via an insulin pump to the patient. The storage chamber can be replenished as needed, from a source external to the patient. The detector, processor, and pump provide a feedback loop to maintain blood glucose levels within a predetermined range, and alarms can be triggered if glucose levels fall outside the predetermined range. The predetermined range is adjustable by the user to allow for tighter or looser glycemic control. The device also comprises memory to log glucose levels as a function of time for calibration purposes, as well as to provide a glucose level history for the user. The device further comprises a transmitter to allow for optional wireless communication with a mobile device and/or over a computer network.

Example 13

Contact Lens Comprising Nanoparticle Transducers

In this example, a contact lens is provided that comprises nanoparticle transducers for the detection of an analyte in lacrimal fluid of a subject wearing the lens on the subject's eye. When worn by the subject, the nanoparticle transducers come into contact with the tear fluid of the eye as the fluid permeates the lens. The lens includes nanoparticle transducers that comprise glucose oxidase and a chromophore, configured as described above for the detection of glucose. The transducers are embedded into a substantially transparent membrane of the contact lens, which is shaped to provide vision correction to the wearer. The subject is provided a scanner that can be placed over the eyes, and that provides illumination to induce fluorescence in the nanoparticle transducers, and which comprises a detector for detecting the induced fluorescence. The nanoparticle transducers emit light with an intensity that varies in response to the concentration of the analyte, thereby providing a measurement of analyte concentration in the subject's tear fluid. The concentration of analyte in the tear fluid correlates to the concentration of analyte in the blood; thus, this measurement provides a measurement of the analyte concentration in the blood. The scanner can also provide retinal scanning for the detection of conditions such as diabetic retinopathy.

Example 14

Device for Detection of Blood Glucose Levels from Measurements of Sweat

In this example, a device is provided for the measurement of blood glucose levels based on detection of glucose in the sweat of a subject. A device is provided comprising a wearable band, a plurality of nanoparticle transducers, an illumination source, and an optical sensor. The nanoparticle transducers comprise glucose oxidase and a chromophore, configured as described above for the detection of glucose. The nanoparticle transducers are disposed on the surface of the device such that, when worn by a subject, the nanoparticle transducers contact the subject's skin. As sweat is typically present on the skin, the nanoparticle transducers are thus able to contact the sweat of the subject. The sweat of the subject contains glucose that varies in proportion to the glucose in the blood; accordingly, measurement of the glucose concentration of sweat allows for the determination of blood glucose levels.

The illumination source of the device is positioned to provide illumination to the nanoparticle transducers contacting the skin of the subject, so as to induce fluorescence. The nanoparticle transducers produce fluorescence that varies based on the concentration of glucose in a sweat film on the contacted skin. The fluorescence is detected by an optical sensor, which is coupled to a processor. The processor determines a glucose concentration in the sweat based on the fluorescence detected by the optical sensor. The processor then determines a blood glucose concentration based on the glucose concentration in the sweat.

Example 15

Nanoparticle Transducers Based on the Detection of a Product Reaction Element ($H_2O_2$)

Figure 21:
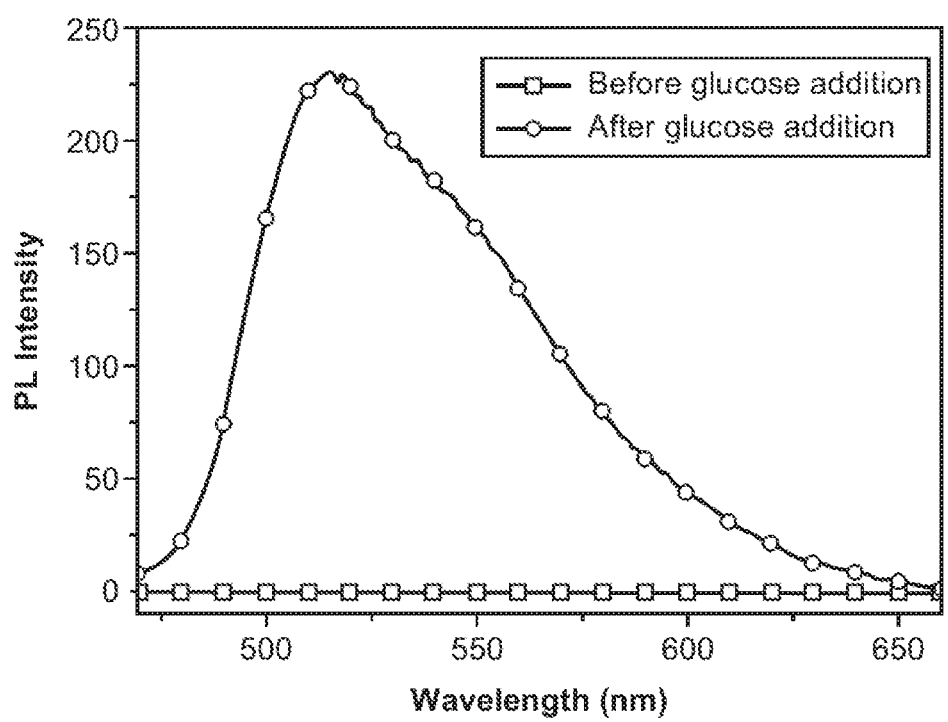
FIG. 21 shows the spectral response of a $H_2O_2$-based nanoparticle transducer comprising a nanoparticle-GOx assembly.

In this example, nanoparticle transducers for detecting a product reaction element were produced and characterized in an exemplary system for detection of fluid constituents. Aqueous dispersion of nanoparticle was formed using a reprecipitation method. In one preparation, the functional polymer PSMA and hydrogen peroxide sensitive dye were dissolved in anhydrous tetrahydrofuran (THF) by stirring overnight under inert atmosphere to make a 1 mg/mL stock solution, respectively. The solutions were diluted and mixed in THF to produce a solution mixture that was further added quickly to Milli-Q water in a bath sonicator while sonicating the mixture. The THF was removed by nitrogen stripping, and the solution concentrated to 5 mL on a 90° C. hotplate followed by filtration through a 0.2 micron filter. During nanoparticle formation, the maleic anhydride units of PSMA molecules were hydrolyzed in the aqueous environment, generating carboxyl groups on Pdots. The $H_2O_2$-sensitive dye molecules were encapsulated inside the nanoparticle or associated with the polymer. Hydrogen peroxide ($H_2O_2$) is a by-product of cell respiration and can be generated during many enzyme-catalyzed reactions. For example, the $H_2O_2$ concentration can be affected by glucose oxidase-catalyzed glucose oxidation reaction. The changes in hydrogen peroxide concentration induced by glucose can be transformed into an optical signal by using an H$_2$O$_2$ responsive Pdot transducer. FIG. 21 shows the spectral response of a H$_2$O$_2$-based nanoparticle transducer comprising a nanoparticle-GOx assembly. Upon addition of glucose, an apparent fluorescence increase was observed due to the presence of H$_2$O$_2$ generated by GOx-catalyzed glucose oxidation reaction. Thus, the nanoparticle-GOx assembly functions as a nanoparticle transducer for the detection of an analyte—glucose, in this example—based on fluorescence mediated by a product of a reaction of the analyte catalyzed by an enzyme coupled to the assembly.

Other nanoparticle or Pdot transducers, including ion or metal ion based Pdot transducers, pH-based Pdot transducers, and heat-based Pdot transducers, can be similarly prepared as described above. Metal ions play important roles in the biological function of many enzymes. Ions can serve as electron donors or acceptors, Lewis acids or structural regulators. The ions participate directly in the catalytic processes. For example, Carboxypeptidase A, liver alcohol dehydrogenase, aspartate transcarbamoylase, and alkaline phosphatase indicate the different roles of metal ions in metalloenzymes, while zinc ions play an essential role in the nucleotide polymerases for maintaining normal growth and development. Thus, ion sensitive Pdots can be used to construct nanoparticle transducers for detection of analytes by incorporating an enzyme that catalyzes a reaction that changes ion concentrations, thereby generating fluorescence that varies with the analyte concentration. Similarly, proton donors and acceptors—acids and bases, for example—may donate and accept protons in enzyme catalysis. For example, the initial step of the serine protease catalytic mechanism involves the histidine of the active site accepting a proton from the serine residue. Accordingly, pH sensitive Pdots can be used to construct nanoparticle transducers for detection of analytes by incorporating an enzyme that catalyzes a reaction that changes pH, thereby generating fluorescence that varies with the analyte concentration.

While preferred aspects of the present invention have been shown and described herein, it will be obvious to those skilled in the art that such aspects are provided by way of example only. Numerous variations, changes, and substitutions will now occur to those skilled in the art without departing from the invention. It should be understood that various alternatives to the aspects of the invention described herein can be employed in practicing the invention. It is intended that the following claims define the scope of the invention and that methods and structures within the scope of these claims and their equivalents be covered thereby.

What is claimed is:

1. A nanoparticle transducer for analyte concentration measurements, comprising:
    an enzyme configured to catalyze a reaction comprising a plurality of reaction elements comprising one or more reactants including the analyte and one or more products; and
    a nanoparticle coupled to the enzyme and comprising one or more chromophores configured to emit fluorescence at a signal fluorescence wavelength and a control fluorescence wavelength, wherein the nanoparticle is a Pdot,
    wherein the one or more chromophores is configured to emit an amount of the fluorescence at the signal wavelength and an amount of the fluorescence emitted at the control fluorescence wavelength defining a fluorescence ratio that varies ratiometrically with a concentration of a reaction element of the plurality of reaction elements,
    wherein the one or more chromophores comprise a first chromophore and a second chromophore,
    wherein the first chromophore is a semiconducting chromophore, and,
    wherein the first chromophore is chemically attached to the second chromophore.

2. The nanoparticle transducer of claim 1, wherein a reaction element of the plurality of reaction elements comprises oxygen and wherein the amount of fluorescence emitted from the one or more chromophores is determined by a concentration of the oxygen.

3. The nanoparticle transducer of claim 1, wherein the amount of the fluorescence emitted from the one or more chromophores is determined by a concentration of a reactant.

4. The nanoparticle transducer of claim 1, wherein the amount of the fluorescence emitted from the one or more chromophores is determined by a concentration of a product.

5. The nanoparticle transducer of claim 1, wherein the enzyme is covalently bonded to the nanoparticle.

6. The nanoparticle transducer of claim 1, wherein the one or more chromophores comprise comprises a dye and wherein the dye is contained within the nanoparticle.

7. The nanoparticle transducer of claim 1, wherein the one or more chromophores comprise a dye, and wherein the dye and the semiconducting polymer interact to produce enhanced fluorescence.

8. The nanoparticle transducer of claim 1, wherein the one or more chromophores comprise a blend of two or more semiconducting polymers.

9. The nanoparticle transducer of claim 1, wherein the one or more chromophores is configured to emit the fluorescence such that it varies ratiometrically with the concentration of the analyte within a range of analyte concentrations.

10. The nanoparticle transducer of claim 1, wherein:
    the nanoparticle comprises a third chromophore for fluorescent detection of a second analyte;
    a second enzyme is coupled to the nanoparticle and configured to catalyze a second reaction comprising a second plurality of reaction elements;
    the second plurality of reaction elements comprises a second one or more reactants including the second analyte and a second one or more products, and wherein an amount of fluorescence emitted from the second chromophore is determined by a concentration of a second reaction element of the second plurality of reaction elements; and
    the fluorescence of the third chromophore comprises a wavelength different from the fluorescence of the other chromophore.

11. The nanoparticle transducer of claim 1, further comprising:
    a second nanoparticle comprising a third chromophore; and
    a second enzyme coupled to the nanoparticle and configured to catalyze a second reaction comprising a second plurality of reaction elements,
    wherein the second plurality of reaction elements comprises a second one or more reactants including a second analyte and a second one or more products, and wherein an amount of fluorescence emitted from the third chromophore is determined by a concentration of a second reaction element of the second plurality of reaction elements.

12. The nanoparticle transducer of claim 1, wherein the enzyme is selected from the group consisting of ascorbate oxidase, glutamate oxidase, dopamine beta-hydroxylase, cholesterol oxidase, alcohol oxidase, amine oxidase, and cytochrome P450.

13. The nanoparticle transducer of claim 1, wherein the analyte is selected from the group consisting of an amino acid, a protein, a nucleic acid molecule, a transmitter molecule, a drug, a carbohydrate, a lipid, a metabolite, and a sugar.

14. The nanoparticle transducer of claim 1, wherein the analyte concentration is a blood concentration.

15. The nanoparticle transducer of claim 1, comprising a plurality of enzymes, wherein the plurality of enzymes catalyze a respective plurality of reactions each comprising a respective plurality of reaction elements, and wherein the analyte is a reactant of one of the plurality of reactions, and wherein the fluorescence emitted from the one or more chromophores is determined by a concentration of a reaction element of at least one of the reactions.

16. The nanoparticle transducer of claim 1, wherein:

the first chromophore is configured to emit fluorescence at the signal fluorescence wavelength at an intensity determined by the concentration of the reaction element of the plurality of reaction elements; and the second is chromophore configured to emit fluorescence at the control fluorescence wavelength that changes intensity in response to the concentration of the reaction element differently than the first chromophore.

17. The nanoparticle transducer of claim 1, wherein:

the first chromophore is configured to emit fluorescence at the signal fluorescence wavelength at an intensity determined by the concentration of the reaction element of the plurality of reaction elements; and the second chromophore is configured to emit fluorescence at the control fluorescence wavelength that does not change intensity in response to the reaction element.

* * * * *